(12) United States Patent
Smrzka et al.

(10) Patent No.: US 11,986,536 B2
(45) Date of Patent: *May 21, 2024

(54) COMPOUND FOR THE SEQUESTRATION OF UNDESIRABLE ANTIBODIES IN A PATIENT

(71) Applicant: ABLEVIA BIOTECH GMBH, Vienna (AT)

(72) Inventors: Oskar Smrzka, Vienna (AT); Bettina Wanko, Vienna (AT)

(73) Assignee: ABLEVIA BIOTECH GMBH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 17/393,626

(22) Filed: Aug. 4, 2021

(65) Prior Publication Data

US 2021/0369856 A1 Dec. 2, 2021

Related U.S. Application Data

(63) Continuation of application No. 17/424,791, filed as application No. PCT/EP2020/058024 on Mar. 23, 2020.

(30) Foreign Application Priority Data

Mar. 23, 2019 (EP) .................... 19164784

(51) Int. Cl.
| | | |
|---|---|---|
| A61K 47/68 | (2017.01) | |
| A61K 38/00 | (2006.01) | |
| A61K 47/64 | (2017.01) | |
| C07K 5/04 | (2006.01) | |
| C07K 7/06 | (2006.01) | |
| C07K 16/18 | (2006.01) | |

(52) U.S. Cl.
CPC ........ *A61K 47/6811* (2017.08); *A61K 47/643* (2017.08); *A61K 47/644* (2017.08); *C07K 5/04* (2013.01); *C07K 7/06* (2013.01); *A61K 38/00* (2013.01); *C07K 16/18* (2013.01)

(58) Field of Classification Search
None
See application file for complete search history.

(56) References Cited

U.S. PATENT DOCUMENTS

| | | | |
|---|---|---|---|
| 5,578,496 A | 11/1996 | Atassi et al. | |
| 5,637,454 A | 6/1997 | Harley | |
| 6,022,544 A | 2/2000 | Dintzis et al. | |
| 6,498,244 B1* | 12/2002 | Patel | A61P 43/00 |
| | | | 435/235.1 |
| 2004/0258683 A1 | 12/2004 | Innik et al. | |
| 2005/0220785 A1* | 10/2005 | Engle | A61P 7/00 |
| | | | 424/131.1 |
| 2006/0223114 A1 | 10/2006 | Stemmer et al. | |
| 2007/0026396 A1 | 2/2007 | Wallukat et al. | |
| 2008/0051376 A1* | 2/2008 | Sinn | A61P 37/06 |
| | | | 514/169 |
| 2011/0191867 A1* | 8/2011 | Natunen | A61P 31/12 |
| | | | 435/7.1 |
| 2013/0136736 A1 | 5/2013 | Silence | |
| 2013/0259885 A1 | 10/2013 | Saint-Remy | |
| 2016/0144050 A1 | 5/2016 | Kim et al. | |
| 2022/0062435 A1* | 3/2022 | Smrzka | A61K 47/6811 |

FOREIGN PATENT DOCUMENTS

| | | |
|---|---|---|
| EP | 0498658 A1 | 8/1992 |
| EP | 1697421 | 9/2006 |
| EP | 1832600 A1 | 9/2007 |
| EP | 2497828 A1 | 9/2012 |
| EP | 2698386 A1 | 2/2014 |
| EP | 3059244 A1 | 8/2016 |
| WO | 1992/014150 A1 | 8/1992 |
| WO | 1998/030586 A2 | 7/1998 |
| WO | WO0020041 A2 | 4/2000 |
| WO | 00/33887 A2 | 6/2000 |
| WO | WO0204484 A2 | 1/2002 |

(Continued)

OTHER PUBLICATIONS

Zapadka et al., Interface Focus 7: 1-18 (Year: 2017).*
Yu et al., Investigative Ophthalmology & Visual Science 49(2): 522-527 (Year: 2008).*
Raso et al., J Biol Chem 259:1143-1149 (Year: 1984).*
Mahlangu et al., Journal of Thrombosis and Haemostasis, 13: 1989-1998 (Year: 2015).*
Gurda et al., J Virology 86: 7739-7751 (Year: 2012).*
Lloyd et al., Protein Engineering, Design & Selection 22:159-168 (Year: 2009).*
Edwards et al., J Mol Biol. 334(1): 103-118 (Year: 2003).*
Casey et al., J Clinical Microbiology 44(3): 764-771 (Year: 2006).*

(Continued)

*Primary Examiner* — Phuong Huynh
(74) *Attorney, Agent, or Firm* — Greer, Burns & Crain, Ltd

(57) ABSTRACT

The present invention provides a compound for the sequestration of undesirable antibodies (e.g. related to an autoimmune disease) in a patient. The compound comprises an inert biopolymer scaffold and at least a first peptide n-mer of the general formula $P(-S-P)_{(n-1)}$ and a second peptide n-mer of the general formula $P(-S-P)_{(n-1)}$; wherein, independently for each occurrence, P is a peptide with a sequence length of 2-13 amino acids and S is a non-peptide spacer, wherein, independently for each of the peptide n-mers, n is an integer of at least 1, wherein each of the peptide n-mers is bound to the biopolymer scaffold. Also provided are pharmaceutical compositions comprising the compound, as well as a method of sequestering one or more antibodies present in an individual and a method of inhibiting an immune reaction to a treatment with an active agent.

15 Claims, 11 Drawing Sheets

Specification includes a Sequence Listing.

(56) References Cited

FOREIGN PATENT DOCUMENTS

| WO | WO 02/32941 A2 | 4/2002 |
|---|---|---|
| WO | WO 03/100419 A1 | 12/2003 |
| WO | WO2005023848 A2 | 3/2005 |
| WO | WO2009027063 A2 | 3/2009 |
| WO | WO 2011/039510 A2 | 4/2011 |
| WO | WO2011060371 A2 | 5/2011 |
| WO | 2011/130324 A1 | 10/2011 |
| WO | 2012/000889 A1 | 1/2012 |
| WO | WO2014072958 A2 | 5/2014 |
| WO | 2015/136027 A1 | 9/2015 |
| WO | 2015/181393 A1 | 12/2015 |
| WO | 2016/020377 A1 | 2/2016 |
| WO | 2017/046172 A1 | 3/2017 |
| WO | 2017/087589 A2 | 5/2017 |
| WO | 2017/220569 A1 | 12/2017 |
| WO | WO 2018049053 A2 | 3/2018 |
| WO | 2018/102668 A1 | 6/2018 |
| WO | WO2018113802 A1 | 6/2018 |
| WO | WO2018156617 A2 | 8/2018 |
| WO | 2018/167230 A1 | 9/2018 |
| WO | WO2019018439 A1 | 1/2019 |

OTHER PUBLICATIONS

Xie et al., Antimicrobial Agents and Chemotherapy 54(1): 191-196 (Year: 2010).*

Peters, B., et al., "A Community Resource Benchmarking Predictions of Peptide Binding to MHC-I Molecules," PLoS Computational Biology 2(6), e65, Jun. 2006, pp. 0574-0584.

Pien, G., et al., "Capsid antigen presentation flags human hepatocytes for destruction after transduction by adeno-associated viral vectors," The Journal of Clinical Investigation 119(6), Jun. 2009, pp. 1688-1695.

Pishesha, N., et al., "Engineered erythrocytes covalently linked to antigenic peptides can protect against autoimmune disease," PNAS 114(12), Mar. 21, 2017, pp. 3157-3162.

Qi, Y., et al., "Protein-Polymer Conjugation—Moving Beyond PEGylation," Curr Opin Chem Biol 28, Oct. 2015, p. 181-193.

Rey, E., et al., "Characterization of Human Anti-acetylcholine Receptor Monoclonal Autoantibodies from the Peripheral Blood of a Myasthenia Gravis Patient Using Combinatorial Libraries," Clinical Immunology, vol. 96, No. 3, Sep. 2000, pp. 269-279.

Rodríguez-Fernández, C., "What Happens when the Immune System Attacks Life-Saving Drugs?," retrieved from https://www.labiotech.eu/in-depth/immunogenicity-anti-drug-antibodies, May 24, 2017, 3 pages.

Ruff, R., et al., "Nature and Action of Antibodies in Myasthenia Gravis," Neurol Clin 36, 2018, pp. 275-291.

Rummler, S., et al., "Current techniques for AB0-incompatible living donor liver transplantation," World J Transplant 6(3), Sep. 24, 2016, pp. 548-555.

Runcie, K., et al., "Bi-specific and tri-specific antibodies- the next big thing in solid tumor therapeutics," Molecular Medicine 24:50, 2018, pp. 1-15.

Ryan, R., et al., "Oxidative post-translational modifications and their involvement in the pathogenesis of autoimmune diseases," Redox Biology 2, 2014, pp. 715-724.

Sabatos-Peyton, C., et al., "Antigen-specific immunotherapy of autoimmune and allergic diseases," Curr Opin Immunol. 22(5), Oct. 2010, pp. 609-615.

Salmikangas, P., et al., "Chimeric Antigen Receptor T-Cells (CAR T-Cells) for Cancer Immunotherapy—Moving Target for Industry?" Pharm Res 35(152), 2018, pp. 1-8.

Shanmugam, A., et al., "Identification of PSA peptide mimotopes using phage display peptide library," Peptides 32, 2011, pp. 1097-1102.

Simhadri, V., et al., "Prevalence of Pre-existing Antibodies to CRISPR-Associated Nuclease Cas9 in the USA Population" Molecular Therapy: Methods & Clinical Development, vol. 10, Sep. 2018, pp. 105-112.

Sørensen, K., et al., "Liver Sinusoidal Endothelial Cells," Comprehensive Physiology 5, Oct. 2015, pp. 1751-1774.

Spiess, C., et al., "Alternative molecular formats and therapeutic applications for bispecific antibodies," Molecular Immunology 67, 2015, pp. 95-106.

Swiercz, R., et al., "Use of Fc-Engineered Antibodies as Clearing Agents to Increase Contrast During PET," J Nucl Med. 55(7), Jul. 2014, pp. 1204-1207.

Taddeo, A., et al., "Selection and depletion of plasma cells based on the specificity of the secreted antibody," Eur. J. Immunol. 45, 2015, pp. 317-319.

Teschner, S., et al., "ABO-Incompatible Kidney Transplantation Using Regenerative Selective Immunoglobulin Adsorption," Journal of Clinical Apheresis 27, 2012, pp. 51-60.

Tetala, K., et al., "Selective Depletion of Neuropathy-Related Antibodies from Human Serum by Monolithic Affinity Columns Containing Ganglioside Mimics," J. Med. Chem. 54, 2011, pp. 3500-3505.

Tse, L., et al., "Strategies to circumvent humoral immunity to adeno-associated viral vectors," Expert Opin Biol Ther 15 (6), Jun. 2015, pp. 845-855.

Tse, L., et al., "Structure-guided evolution of antigenically distinct adeno-associated virus variants for immune evasion" PNAS, May 30, 2017, pp. E4812-E4821.

Velazquez, V., et al., "Effective Depletion of Pre-existing Anti-AAV Antibodies Requires Broad Immune Targeting," Molecular Therapy: Methods & Clinical Development, vol. 4, Mar. 2017, pp. 159-168.

Vigl, B., et al., "Quantitative in vitro and in vivo models to assess human IgE B cell receptor crosslinking by IgE and EMPD IgE targeting antibodies," Journal of Immunological Methods 449, 2017, pp. 28-36.

Vincent, A., et al., "Serological and experimental studies in different forms of myasthenia gravis," Ann. N.Y. Acad. Sci., 2018, pp. 1-11.

Wallukat, G., et al., "Patients with preeclampsia develop agonistic autoantibodies against the angiotensin AT1 receptor," The Journal of Clinical Investigation 103(7), Apr. 1999, pp. 945-952.

Wang, D., et al., "AAgAtlas 1.0: a human autoantigen database," Nucleic Acids Research, 2017, vol. 45, Database Issue, pp. D769-D776.

Williams, B., et al., "Creating Protein Affinity Reagents by Combining Peptide Ligands on Synthetic DNA Scaffolds," I Am Chem Soc 131(47), Dec. 2, 2009, pp. 17233-17241.

Wolchok, J., "Altered Self: The Not-so-neo-antigens," Nature Reviews Immunology, Research Highlights, 2018, 1 page.

Yu, X., et al., "Beyond Antibodies as Binding Partners: The Role of Antibody Mimetics in Bioanalysis," Annu Rev Anal Chem 10(1), Jun. 12, 2017, pp. 293-320.

Zhang, P., et al., "Anti-PEG antibodies in the clinic: current issues and beyond PEGylation," J Control Release 244(Pt B), Dec. 28, 2016, pp. 184-193.

Zhou, C., et al., "Angiotensin receptor agonistic autoantibodies induce preeclampsia in pregnant mice," Nat Med. 14 (8), Aug. 2008, pp. 855-862.

International Preliminary Report on Patentability for PCT/EP2020/058024, dated Apr. 12, 2021.

International Search Report and Written Opinion received for PCT/EP2020/058024, dated Aug. 12, 2020.

Extended European Search Report received in EP 19164784.1, dated Nov. 6, 2019.

Bansal, R., et al., "Peptide-Modified Albumin Carrier Explored as a Novel Strategy for a Cell-Specific Delivery of Interferon Gamma To Treat Liver Fibrosis", Molecular Pharmaceutics, Oct. 3, 2011, pp. 1899-1909, vol. 8, No. 5.

Gotti, C., et al., "The binding site for a-bungarotoxin resides in the sequence 188-201 of the a-subunit of acetylcholine receptor: structure, conformation and binding characteristics of peptide [Lys] 188-201", Neurosciene Letters, Apr. 15, 1987, pp. 113-119, vol. 82.

Neumann, D., et al., "Analysis of ligand binding to the synthetic dodecapeptide 185-196 of the acetylcholine receptor a subunit", Proc. Natl. Acad. Sci., Dec. 1986, pp. 9250-9253, vol. 83.

Bernatowicz, M., et al., "Preparation of Peptide-Protein Immunogens Using N-Succinimidyl Bromoacetate as a Heterobifunctional Crosslinking Reagent", Analytical Biochemistry, 1986, pp. 95-102, vol. 155.

(56) References Cited

OTHER PUBLICATIONS

Fu, M., et al., "Functional Epitope Analysis of the Second Extracellular Loop of the Human Heart Muscarinic Acetylcholine Receptor", J. Mol Cell Cardiol, 1995, pp. 427-436, vol. 27.

European Office Action dated Jan. 13, 2022 For European Application No. 21187621.4-1118.

Roberts, D., et al., "Hexon-chimaeric adenovirus serotype 5 vectors circumvent pre-existing anti-vector immunity", Nature, May 11, 2006, pp. 239-243, vol. 44.

Ruzieh, M., et al., The role of autoantibodies in the syndromes of orthostatic intolerance: a systematic review, Scandinavian Cardiovascular Journal, Jul. 10, 2017, pp. 1-5.

Salganik, M., et al., "Adeno-associated Virus as a Mammalian DNA Vector", Microbiology Spectrum, Jul. 2, 2015, pp. 1-21.

Scheibenbogen, C., et al., "Immunoadsorption to remove ß2 adrenergic receptor antibodies in Chronic Fatigue Syndrome CFS/ME", PLOS ONE, Mar. 15, 2018, pp. 1-15.

Schimke, I., et al., "Reduced Oxidative Stress in Parallel to Improved Cardiac Performance One Year After Selective Removal of Anti-Beta 1-Adrenoreceptor Autoantibodies in Patients With Idiopathic Dilated Cardiomyopathy: Data of a Preliminary Study", Journal of Clinical Apheresis, 2005, pp. 137-142, vol. 20.

Shoenfeld, Y., et al., "Complex syndromes of chronic pain, fatigue and cognitive impairment linked to autoimmune dysautonomia and small fiber neuropathy", Clinical Immunology, Mar. 10, 2020, 11 pages.

Siman, D., "The use of epitope arrays in immunodiagnosis of infectious disease: Hepatitis C virus a case study", Analytical Biochemistry, 2013, pp. 63-70, vol. 432.

Sonntag, F., et al., "The Assembly-Activating Protein Promotes Capsid Assembly of Different Adeno-Associated Virus Serotypes", Journal of Virology, Dec. 2011, p. 12686-12697, vol. 85, No. 23.

Sotzny, F., et al., "Myalgic Encephalomyelitis/Chronic Fatigue Syndrome—Evidence for an autoimmune disease", Autoimmunity Reviews, 2018, pp. 601-609, vol. 17.

Thornton, K., MD, et al., "Autonomic dysfunction: A guide for FPs", The Journal of Family Practice, Sep. 2017, pp. 539-543, vol. 66, No. 9.

Tian, X., et al., "Broadly neutralizing monoclonal antibodies against human adenovirus types 55, 14p, 7, and 11 generated with recombinant type 11 fiber knob", Emerging Microbes & Infections, Dec. 8, 2018, vol. 7, No. 206.

Trinh, V., et al., "Design, synthesis, and characterization of a 39 amino acid peptide minic of the main immunogenic region of the Torpedo acetylcholine receptor", Modular Immunology, Jan. 4, 2014, pp. 79-90, vol. 59.

Tsartos, S.J., et al., "The Main Immunogenic Region (MIR) of the Nicotinic Acetylcholine Receptor and the Anti-MIR Antibodies", Molecular Neurobiology, 1991, pp. 1-29, vol. 5.

Tseng, Y.S., et al., "Mapping the AAV capsid host antibody response toward the development of second generation gene delivery vectors", Frontiers in Immunology, Jan. 30, 2014, pp. 1-11, vol. 5, No. 9.

Tzartos, S., et al., "Demonstration of a main immunogenic region on acetylcholine receptors from human muscle using monoclonal antibodies to human receptor", Federation of European Biochemical Societies, Jul. 1983, pp. 116-118, vol. 158, No. 1.

Varghese, R., et al., Postentry Neutralization of Adenovirus Type 5 by an Antihexon Antibody, Journal of Virology, Nov. 2004, pp. 12320-12332, vol. 78, No. 22.

Villard, S., S., et al., "Peptide decoys selected by phage display block in vitro and in vivo activity of a human anti-FVIII inhibotor", Hemostasis, Thrombosis, and Vascular Biology, Aug. 2004, pp. 949-952, vol. 102, No. 3.

Wallenius, M., et al., "Autoantibodies in Pandemrix®-induced narcolepsy: Nine candidate autoantigens fail the conformational autoantibody test", Autoimmunity, Jul. 22, 2019, pp. 1-8.

Wallukat, G., et al., "Agonistic autoantibodies directed against G-protein-coupled receptors and their relationship to cardiovascular diseases", Semin Immunopathol, Apr. 24, 2014, pp. 351-363, vol. 36.

Wallukat, G., Ph.D., et al., "Specific Removal of b1-Adrenergic Autoantibodies from Patients with Idiopathic Dilated Cardiomyopathy", The New England Journal of Medicine, Nov. 28, 2002, pp. 1806, vol. 347, No. 22.

Wang, C., et al., "Molecular Grafting onto a Stable Framework Yields Novel Cyclic Peptides for the Treatment of Multiple Sclerosis", 2014, pp. 156-163.

Wang, R., et al., "A Murine Monoclonal Antibody With Potent Neutralization Ability Against Human Adenovirus 7", Frontiers in Cellular and Infection Microbiology, Dec. 4, 2019, pp. 1-8, vol. 9, No. 417.

Yoshikawa, H., et al., "FK506 Prevents Induction of Rat Experimental Autoimmune Myasthenia Gravis", Journal of Autoimmunity, 1997, pp. 11-16, vol. 10.

Zong, S., et al., "Neuronal Surface Autoantibodies in Neuropsychiatric Disorders: Are There Implications for Depression?", Frontiers in Immunology, Jul. 5, 2017, pp. 1-12, vol. 8, No. 752.

Ananyeva, N. et al., "Inhibitors in Hemaphilia A: mechanisms of inhibition, management and perspectives", Blood Coagulation and Fibrinolysis, 2004, pp. 1-16 , vol. 15, No. 2.

Balakrishan, B., et al., "Biopolymers augment viral vectors based gene delivery", J. Biosci, 2019, pp. 2-8, vol. 44, No. 84.

Bennett, A., et al., "Structure comparison of the chimeric AAV2.7m8 vector with parental AAV2", J. Struct Biol., Feb. 1, 2020, pp. 1-30, vol. 209, No. 2.

Bertin, B., et al., "Capsid-specific removal of circulating antibodies to adeno-associated virus vectors", Scientific Reports, 2020, pp. 1-11, vol. 10, No. 684.

Bornholz B. et al., Diagnostic and therapeutic aspects of B1-adrenergic receptor autoantibodies in human heart disease, Autoimmunity Reviews, 2014, pp. 954-962, vol. 13.

Cearley, C., et al., "Expanded Repertoire of AAV Vector Serotypes Mediate Unique Patterns of Transduction in Mouse Brain", The American Society of Gene Therapy, Oct. 2008, pp. 1710-1718, vol. 16, No. 10.

Colella, P., et al., "Emerging Issues in AAV-Mediated In Vivo Gene Therapy", Molecular Therapy: Methods & Clinical Development, Mar. 2018, pp. 87-104, vol. 87-104, vol. 8.

Cortes Rivera, M., et al., "Myalgic Encephalomyelitis/Chronic Fatigue Syndrome: A Comprehensive Review", Diagnostics, 2019, pp. 1-34, vol. 9, No. 91.

Costa Verda, H., et al., "AAV Vector Immunogenicity in Humans: A Long Journey to Successful Gene Transfer", Molecular Therapy, Mar. 2020, pp. 723-746, vol. 28, No. 3.

Domenger, C., Next-generation AAV vectors—do not judge a virus (only) by its cover Human Molecular Genetics, 2019, pp. 1-12, vol. 28, No. R.1.

Dungen, H., MD, et al., "β-Adrenoreceptor Autoantibodies in Heart Failure", Circulation: Heart Failure, Jan. 2020, pp. 1-9.

Fausther-Bovendo H., et al., "Pre-existing immunity against Ad vectors", Human Vaccines & Immunotherapeutics, Oct. 2014, pp. 2875-2884, vol. 10, No. 10.

Franchini, M. et al., "Acquired hemophilia A: a review of recent data and new therapeutic options", Hematology, 2017, pp. 514-520, vol. 22, No. 9.

Galli, J., et al. Paraneoplastic Diseases of the Central Nervous System [version 1; peer review: 2 approved], F1000Research, Mar. 6, 2020, pp. 1-11, vol. 9.

Giangrande P.L.P., et al., "European principles of inhibitor management in patients with haemophilia", Orphanet Journal of Rare Diseases, 2018, pp. 1-6, vol. 13, No. 66.

Giannoccaro, M., et al., "Antibody-mediated central nervous system diseases", Brain and Neuroscience Advances, pp. 1-10, vol. 2.

Giannoccaro M., et al., "In vivo Mechanisms of Antibody-Mediated Neurological Disorders: Animal Models and Potential Implications", Frontiers in Neurology, Feb. 5, 2020, pp. 1-18, vol. 10.

(56) References Cited

OTHER PUBLICATIONS

Golden, E., et al., "Autoimmune autonomic neuropathies and ganglionopathies: epidemiology, pathophysiology, and therapeutic advances", Clinical Autonomic Research, 2019, pp. 277-288, vol. 29.
Gunning, T., et al., "Postural Orthostatic Tachycardia Syndrome Is Associated With Elevated G-Protein Coupled Receptor Autoantibodies", American Heart Association, 2019, pp. 1-10.
Huang K., et al., "Autoimmune Channelopathies at Neuromuscular Junction", Frontiers in Neurology, May 17, 2019, pp. 1-16, vol. 10, No. 516.
Imamura, M., et al., "Ganglionic Acetylcholine Receptor Antibodies and Autonomic Dysfunction in Autoimmune Rheumatic Diseases", International Journal of Molecular Sciences, 2020, pp. 1-15, vol. 21.
Jacob, G., et al., "Vagal and Sympathetic Function in Neuropathic Postural Tachycardia Syndrome", Nervous System, Hypertension, 2020, pp. 1087-1096.
Joubert, B., et al., "Autoimmune channelopathies in paraneoplastic neurological syndromes", Biochimica et Biophysica Acta, 2015, pp. 2665-23676.
Kadonosono, T., et al., "Design Strategy to Create Antibody Mimetics Harbourning Immobilised Complementary Determining Region Peptides for Practical Use", Scientific Reports, 2020, pp. 1-11, vol. 10, No. 891.
Kim, J., et al., "Channelopathies" Korean J. Pediatr., 2014, pp. 1-18, vol. 57, No. 1.
Kim, D., et al., "Systematic review of randomized controlled trials for chronic fatigue syndrome/myalgic encephalomyelitis (CFS/ME)", Journal of Translational Medicine, 2020, pp. 1-12, vol. 18, No. 7.
Konkle, B., et al., "Hemophilia A Synonym: Factor VIII Deficiency", U.S. National Library of Medicine, Gene Reviews, Jun. 22, 2017, pp. 1-24.
Krasnykh, V., et al., "Characterization of an Adenovirus Vector Containing a Heterologous Peptide Epitope in the HI Loop of the Fiber Knob", Journal of Virology, Mar. 1998, pp. 1844-1852, vol. 72, No. 3.
Kruzik, A., et al., "Prevalence of Anti-Adeno-Associated Virus Immune Responses in International Cohorts of Healthy Donors", Molecular Therapy, Method & Clinical Development, Sep. 2019, pp. 126-133, vol. 14.
Labovsky, V., et al., "Anti-b1-adrenergic receptor autoantibodies in patients with chronic Chagas heart disease", British Society for Immunology, Clinical and Experimental Immunology, 2007, pp. 440-449, vol. 148.
Lacroix-Desmazes, S., et al., Tolerating Factor VIII: Recent Progress, Frontiers in Immunology, Jan. 2020, pp. 1-20, vol. 10, No. 2991.
Lavigne-Lissalde, G., et al., "Anti-factor VIII antibodies", Jun. 22, 2005, pp. 760-769, vol. 94.
Azaridis, K., et al., "Specific removal of autoantibodies by extracorporeal immunoadsorption ameliorates experimental autoimmune myasthenia gravis", Journal of Neuroimmunology, 2017, pp. 1-7.
Li., C., et al., "Engineering adeno-associated virus vectors for gene therapy", Nature Reviews, 2020, pp. 1-18.
Ljung, R., et al., "Intracranial haemorrhage in haemophilia A and B", British Journal of Haematology, 2007, pp. 378-384, vol. 140.
Magnusson, Y., et al., "Antigenic analysis of the second extracellular loop of the human beta-adrenergic receptors", Clin. exp. Immunol., 1989, pp. 42-49, vol. 78.
Mamalaki, A., et al., "Bacterial expression of a single-chain Fv fragment which efficiently protects the acetylcholine receptor against antigenic modulation causes by myasthenic anitbodies", Eur. J. Immunol., 1993, pp. 1839-1845, vol. 23.
Manno, C., et al., "Successful transduction of liver in hemophilia by AAV-Factor IX and limitations imposed by the host immune response", Nature Medicine, Mar. 2006, pp. 346-347, vol. 12.

Matsui, S., et al., "Peptides Derived from Cardiovascular G-protein-coupled Receptors Induce Morphological Cardiomyopathie Changes in Immunized Rabbits", J. Mol Cell Cardiol., 1997, pp. 641-655, vol. 29.
McKeon A., et al., "Autoimmune autonomic disorders", Handbook of Clinical Neurology, 2006, pp. 405-416, vol. 133.
Meyer, C., et al., "Antibodies against GPCR", Frontiers in Bioscience, Jun. 1, 2018, pp. 2177-2194, vol. 23.
Mietsch M., et al., "OneBac: Platform for Scalable and High-Titer Production of Adeno-Associated Virus Serotype 1- 12 Vectors for Gene Therapy", Human Gene Therapy, Mar. 2014, pp. 212-222, vol. 25.
Mimuro, J., et al., "Minimizing the Inhibitory Effect of Neutralizing Antibody for Efficient Gene Expression in the Liver With Adeno-associated Virus 8 Vectors", The American Society of Gene & Cell Therapy, Feb. 2013, pp. 318-323, vol. 21 No. 2.
Moody, P., et al., "Receptor Crosslinking: A General Method to Trigger Internalization and Lysosomal Targeting of Therapeutic Receptor:Ligand Complexes", Journal of the American Society of Gene & Cell Therapy, Dec. 2015, op. 1888-1898, vol. 23 No. 12.
Muller, J., et al., "Immunoglobulin Adsorption in Patients With Idiopathic Dilated Cardiomyopathy", American Heart Association, Inc., 2000, pp. 385-391.
Nagatomo, Y., MD., et al., "Autoantibodies and Cardiovascular Dysfunction: Cause or Consequence?", Curr Heart Fail Rep., Dec. 2014, pp. 500-508, vol. 11, No. 4.
Nakane, S., et al., "Autoimmune autonomic ganglionopathy: an update on diagnosis and treatment", Expert Review of Neurotherapeutics, 2018, pp. 953-965, vol. 18, No. 12.
Ogris, M., et al., "Receptor Crosslinking in Drug Delivery: Detour to the Lysosome?", American Society of Gene & Cell Therapy, Dec. 2015, pp. 1802-1804, vol. 23, No. 12.
Peters, R., et al., "Advances and innovations in haemophilia treatment", Nature Reviews, Jun. 8, 2018, pp. 1-16.
Rice, et al., "EMBOSS: The European Molecular Biology Open Software Suite", Jun. 2000, pp. 1-2, vol. 16, No. 6.
Brune, K., et al., "New Routes and Opportunities for Modular Construction of Particulate vaccines: Stick, Click, and Glue," Frontiers in Immunology 9, Article 1432, Jun. 2018, 15 pages.
Bruno, J., "Potential Inherent Stimulation of the Innate Immune System by Nucleic Acid Aptamers and Possible Corrective Approaches," Pharmaceuticals 11, 2018, pp. 1-7.
Carter, J., et al., "B Cell Epitope Mapping Using Synthetic Peptides," Current Protocols in Immunology, 2004, pp. 9.4.1-9.4.23.
Colella, P., et al., "Emerging Issues in AAV-Mediated In Vivo Gene Therapy," Molecular Therapy: Methods & Clinical Development 8, Mar. 2018, pp. 87-104.
Delignat, S., et al., "Inhibitor Formation in Congenital Hemophilia A: an Immunological Perspective," Seminars in Thrombosis & Hemostasis, 2018, 14 pages.
Devanaboyina, S., et al., "Engineered clearing agents for the selective depletion of antigen-specific antibodies," Nature Communications 8, 2017, pp. 1-6.
Dunbar, C., et al., "Gene therapy comes of age," Science 359, Review Summary, Jan. 12, 2018, 12 pages.
Elliot, S., et al., "A pre-eclampsia-associated Epstein-Barr virus antibody cross-reacts with placental GPR50," Clinical Immunology 168, 2016, pp. 64-71.
Erlandsson, A., et al., "In vivo clearing of idiotypic antibodies with antiidiotypic antibodies and their derivatives," Molecular Immunology 43, 2006, pp. 599-606.
Fitzpatrick, Z., et al., "Influence of Pre-existing Anti-capsid Neutralizing and Binding Antibodies on AAV Vector Transduction," Molecular Therapy: Methods & Clinical Development, vol. 9, Jun. 2018, pp. 119-129.
Garces, J., et al., "Antibody-Mediated Rejection: A Review," Ochsner Journal 17, 2017, pp. 46-55.
Gazarian, K., et al., "Mimotope peptides selected from phage display combinatorial library by serum antibodies of bigs experimentally infected with Taenia solium as leads to developing diagnostic antigens for human neurocysticercosis," Peptides 38, 2012, pp. 381-388.

(56) References Cited

OTHER PUBLICATIONS

Gfeller, D., et al., "Current tools for predicting cancer-specific T cell immunity," Oncoimmunology, vol. 5, No. 7, 2016, e1177691, 9 pages.

Ginn, S., et al., "Gene therapy clinical trials worldwide to 2017: An update," J Gene Med 20, 2018, pp. 1-16.

Gurda, B., et al., "Mapping a Neutralizing Epitope onto the Capsid of Adeno-Associated Virus Serotype 8," Journal of Virology 86(15), Aug. 2012, pp. 7739-7751.

Haberland, A., et al., "AptamerBC007—A broad spectrumneutralizer of pathogenic autoantibodies against G-protein-coupled receptors," European Journal of Pharmacology 789, 2016, pp. 37-45.

Hansen, L., et al., "Identification and Mapping of Linear Antibody Epitopes in Human Serum Albumin Using High-Density Peptide Arrays," Plos One, vol. 8, No. 7, Jul. 2013, e68902, 10 pages.

Homma, M., et al., "A Novel Fusion Protein, AChR-Fc, Ameliorates Myasthenia Gravis by Neutralizing Antiacetylcholine Receptor Antibodies and Suppressing Acetylcholine Receptor-Reactive B Cells," Neurotherapeutics 14, 2017, pp. 191-198.

Howard, J., "Myasthenia gravis: the role of complement at the neuromuscular junction," Ann. N.Y. Acad. Sci., Myasthenia Gravis and Related Disorders, 2017, pp. 1-16.

Janssen, B., et al., "Reversible blocking of antibodies using bivalent peptide—DNA conjugates allows protease- activatable targeting," Chem. Sci. 4, 2013, pp. 1442-1450.

Jansson, L., et al., "Immunotherapy With Apitopes Blocks the Immune Response to TSH Receptor in HLA-DR Transgenic Mice," Endocrinology 159(9), Sep. 2018, pp. 3446-3457.

Jensen, K., et al., "Improved methods for predicting peptide binding affinity to MHC class II molecules," Immunology 154, 2018, pp. 394-406.

Jurtz, V., et al., "NetMHCpan 4.0: Improved peptide-MHC class I interaction predictions integrating eluted ligand and peptide binding affinity data1," J Immunol. 199(9), Nov. 2017, pp. 3360-3368.

Kishnani, P., et al., "Immune response to enzyme replacement therapies in lysosomal storage diseases and the role of immune tolerance induction," Molecular Genetics and Metabolism, 2016, pp. 1-18.

Koşaloğlu-Yalçin, Z., et al., "Predicting T cell recognition of MHC class I restricted neoepitopes," Oncoimmunology vol. 7, No. 11, 2018, e1492508, 15 pages.

Krishna, M., et al., "Immunogenicity to Biotherapeutics—The Role of Anti-drug Immune Complexes," Frontiers in Immunology 7(21), Feb. 2, 2016, pp. 1-13.

Krishnamurthy, V, et al., "Multivalency in Ligand Design," Fragment-based Approaches in Drug Discovery, 2006, op. 11-53.

Lazaridis, K., et al., "Specific removal of autoantibodies by extracorporeal immunoadsorption ameliorates experimental autoimmune myasthenia gravis," Journal of Neuroimmunology 312, 2017, pp. 1-7.

Leung, N., et al., "Screening and identification of mimotopes of the major shrimp allergen tropomyosin using one-bead-one-compound peptide libraries," Cellular & Molecular Immunology 14, 2017, pp. 308-318.

Lim, S., et al., "Bioconjugation of therapeutic proteins and enzymes using the expanded set of genetically encoded amino acids," Crit Rev Biotechnol, Early Online Edition, 2015, pp. 1-13.

Lim, H., et al., "A pilot study on using rapamycin-carrying synthetic vaccine particles (SVP) in conjunction with enzyme replacement therapy to induce immune tolerance in Pompe disease," Molecular Genetics and Metabolism Reports 13, 2017, pp. 18-22.

Lin, C., et al., "Identification of a major epitope by anti-interferon-y autoantibodies in patients with mycobacterial disease," Nature Medicine, Advance Online Publication, 2016, pp. 1-10.

Lorentz, K., et al., "Engineered binding to erythrocytes induces immunological tolerance to E. coli asparaginase," Sci. Adv., Jul. 17, 2015, e1500112, 10 pages.

Lundstrom, K., "Viral Vectors in Gene Therapy," Diseases 6, 42, 2018, pp. 1-20.

Luo, J., et al., "Main immunogenic region structure promotes binding of conformation-dependent myasthenia gravis autoantibodies, nicotinic acetylcholine receptor conformation maturation, and agonist sensitivity," J Neurosci. 29(44), Nov. 4, 2009, pp. 13898-13908.

Luo, J., et al., "AChR-specific immunosuppressive therapy of myasthenia gravis," Biochemical Pharmacology 97(4), 2015, pp. 609-619.

Majowicz, A., "Seroprevalence of Pre-Existing Nabs Against AAV1, 2, 5, 6 and 8 in South African Hemophilia B Patient Population," Blood Journal, Gene Therapy and Transfer, Nov. 13, 2019, 5 pages.

Mazor, R., et al., "Tolerogenic nanoparticles restore the antitumor activity of recombinant immunotoxins by mitigating Immunogenicity," PNAS, Jan. 8, 2018, pp. E733-E742.

Meister, D., et al., "Unnatural amino acids improve affinity and modulate immunogenicity: Developing peptides to treat MHC type II autoimmune disorders," Peptide Science, 2018, pp. 1-21.

Miao, C., "Advances in Overcoming Immune Responses following Hemophilia Gene Therapy," J Genet Syndr Gene Ther, Dec. 23, 2011; pp. 1-17.

Mingozzi, F., et al., "Immune responses to AAV vectors: overcoming barriers to successful gene therapy," Blood 122 (1), Jul. 4, 2013, pp. 23-36.

Mingozzi, F., et al., "Overcoming Preexisting Humoral Immunity to AAV Using Capsid Decoys," Sci Transl Med. 5 (194), Jul. 17, 2013, pp. 1-20.

Mingozzi, F., et al., "Overcoming the Host Immune Response to Adeno-Associated Virus Gene Delivery Vectors: The Race Between Clearance, Tolerance, Neutralization, and Escape," Annu. Rev. Virol. 4, 2017, pp. 511-534.

Mohan, R., et al., "Virtual Screening of Chemical Compounds for Discovery of Complement C3 Ligands," ACS Omega 3, 2018, pp. 6427-6438.

Morimoto, J., et al., "Dextran as a Generally Applicable Multivalent Scaffold for Improving Immunoglobulin-Binding Affinities of Peptide and Peptidomimetic Ligands," Bioconjugate Chem. 25, 2014, pp. 1479-1491.

Moussa, E., et al., "Immunogenicity of Therapeutic Protein Aggregates," Journal of Pharmaceutical Sciences 105, 2016, pp. 417-430.

Müller, M., "Post-Translational Modifications of Protein Backbones: Unique Functions, Mechanisms, and Challenges," Biochemistry 57, 2018, pp. 177-185.

Nayak, S., et al., "Progress and Prospects: Immune Responses to Viral Vectors," Gene Ther 17(3), Mar. 2010, pp. 295-304.

Omidfar, K., et al., "Advances in phage display technology for drug discovery," Expert Opin. Drug Discov, 2015, pp. 1-19.

Ong, Y., et al. "Recent advances in synthesis and identification of cyclic peptides for bioapplications," Current Topics In Medicinal Chemistry 17, 2017, pp. 2302-2318.

Akbarzadehlaleh, P., et al., "PEGylated Human Serum Albumin: Review of PEGylation, Purification and Characterization Methods", Advanced Pharmaceutical Bulletin, 2016, pp. 309-317, vol. 6, No. 3.

Barry, M., et al., "Retargeting adenoviruses for therapeutic applications and vaccines", FEBS Letters, Feb. 3, 2020, pp. 1918-1946, vol. 594.

Beljaars, L., et al., "Successful Targeting to Rat Hepatic Stellate Cells Using Albumin Modified with Cyclic Peptides That Recognize the Collagen Type VI Receptor", The Journal of Biological Chemistry, Apr. 28, 2000, p. 12743-12751, vol. 275, No. 17.

Dijkstra, C. D., et al., "The heterogeneity of mononuclear phagocytes in lymphoid organs: distinct macrophage subpopulations in the rat recognized by monoclonal antibodies EDI, ED2 and ED3", Immunology, 1985, pp. 589-599, vol. 54.

Etzerodt, A., et al., "Efficient intracellular drug-targeting of macrophages using stealth liposomes directed to the hemoglobin scavenger receptor CD163", Journal of Controlled Release, Jan. 22, 2012, pp. 72-80, vol. 160.

Fabriek, B., et al., "The macrophage scavenger receptor CD163 functions as an innate immune sensor for bacteria", Phagocytes, Granulocytes, and Myelopoiesis, Blood, Jan. 22, 2009, pp. 887-892, vol. 113, No. 4.

(56) References Cited

OTHER PUBLICATIONS

Gaspar, M., "Targeted Delivery of Transferrin-Conjugated Liposomes to an Orthotopic Model of Lung Cancer in Nude Rats", Journal of Aerosol Medicine and Pulmonary Drug Delivery, 2012, pp. 1-9, vol. 25. No. 0.

Granfeldt, A., MD, PHd et al. "Targeting Dexamethasone to Macrophages in a Porcine Endotoxemic Model", Nov. 2013, Online Laboratory Investigations, pp. e308-e319, vol. 41, No. 11.

Graus, Y., et al., "Anti-acetylcholine receptor Fab fragments isolated fromthymus-derived phage display libraries from myasthenia gravis patients reflect predominant specificities in serum and block the action of pathogenic serum antibodies", Immunology Letters, 1997, pp. 59-62, vol. 57.

Graversen, J. et al., "Targeting the Hemoglobin Scavenger receptor CD163 in Macrophages Highly Increases the Anti-inflammatory Potency of Dexamethasone", The American Society of Gene & Cell Therapy, Aug. 2012, pp. 1550-1558, vol. 20, No. 8.

Kang, T., et al., "Structural Aspects of Therapeutic Enzymes to Treat Metabolic Disorders", Human Mutation, Sep. 29, 2009, pp. 1591-1610, vol. 30, No. 12.

Kim, T., "PEG-transferrin conjugated TRAIL (TNF-related apoptosis-inducing ligand) for therapeutic tumor targeting", Sep. 10, 2012, National Institutes of Health, pp. 422-428, vol. 162, No. 2.

Koniev, O., et al., "Developments and recent advancements in the field of endogenous amino acid selective bond forming reactions for bioconjugation" Chem. Soc. Rev., Jan. 19, 2015, pp. 5495-5551, vol. 44.

Madsen, M., et al., "Molecular Characterization of the HaptoglobinHemoglobin Receptor CD163", The Journal of Biological Chemistry, Dec. 3, 2004, p. 51561-51567, vol. 279, No. 49.

Solomon M., et al., "Lysosomal Enzyme Replacement Therapies: Historical Development, Clinical Outcomes, and Future Perspectives Melani Solomon1 and Silvia Muro1,2", Adv Drug Deliv Rev, Sep. 1, 2017, pp. 109-134, vol. 118.

Verdera, H., et al., "AAV Vector Immunogenicity in Humans: A Long Journey to Successful Gene Transfer", Molecular Therapy, Mar. 2020, pp. 723-746, vol. 28, No. 3.

* cited by examiner

A

B
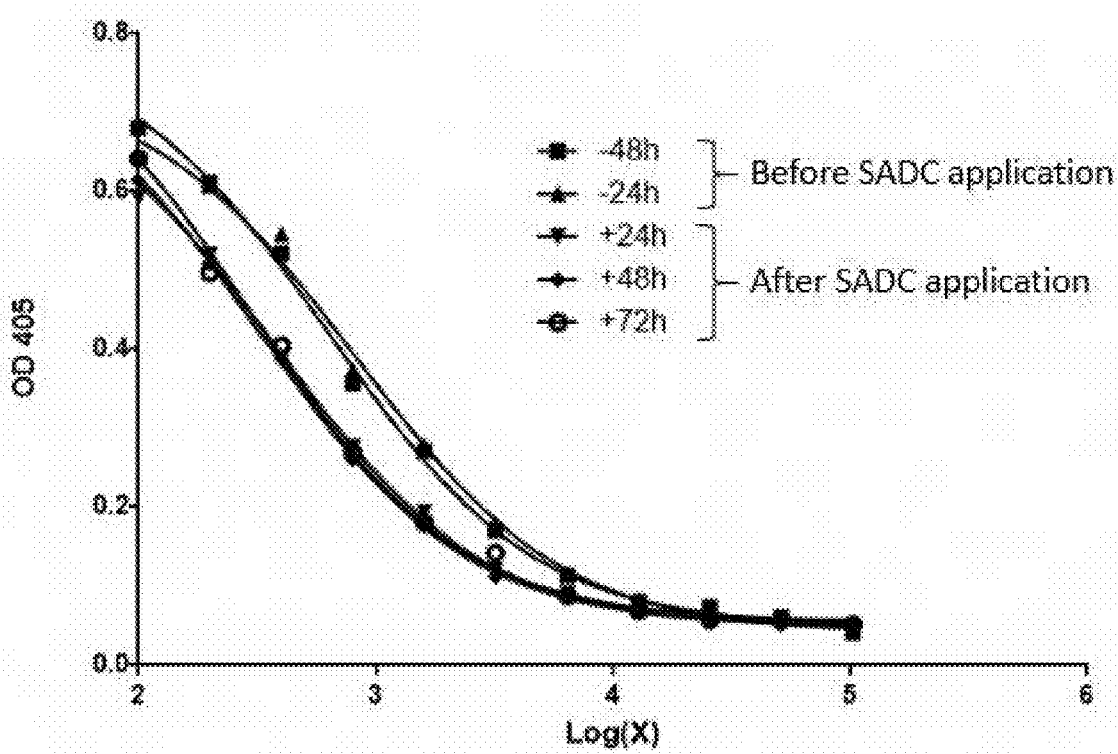
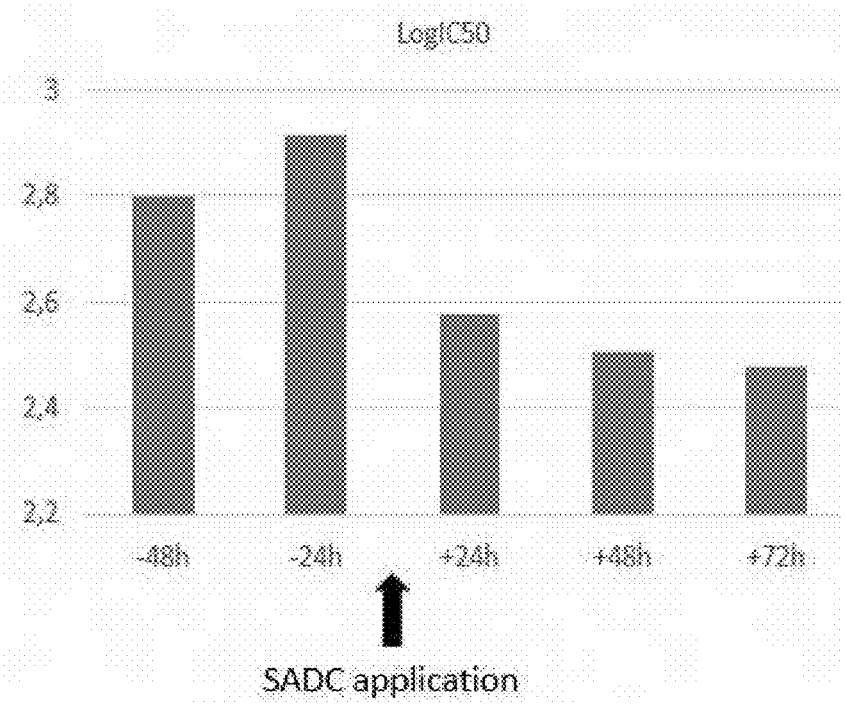
Cont. Fig. 1

C
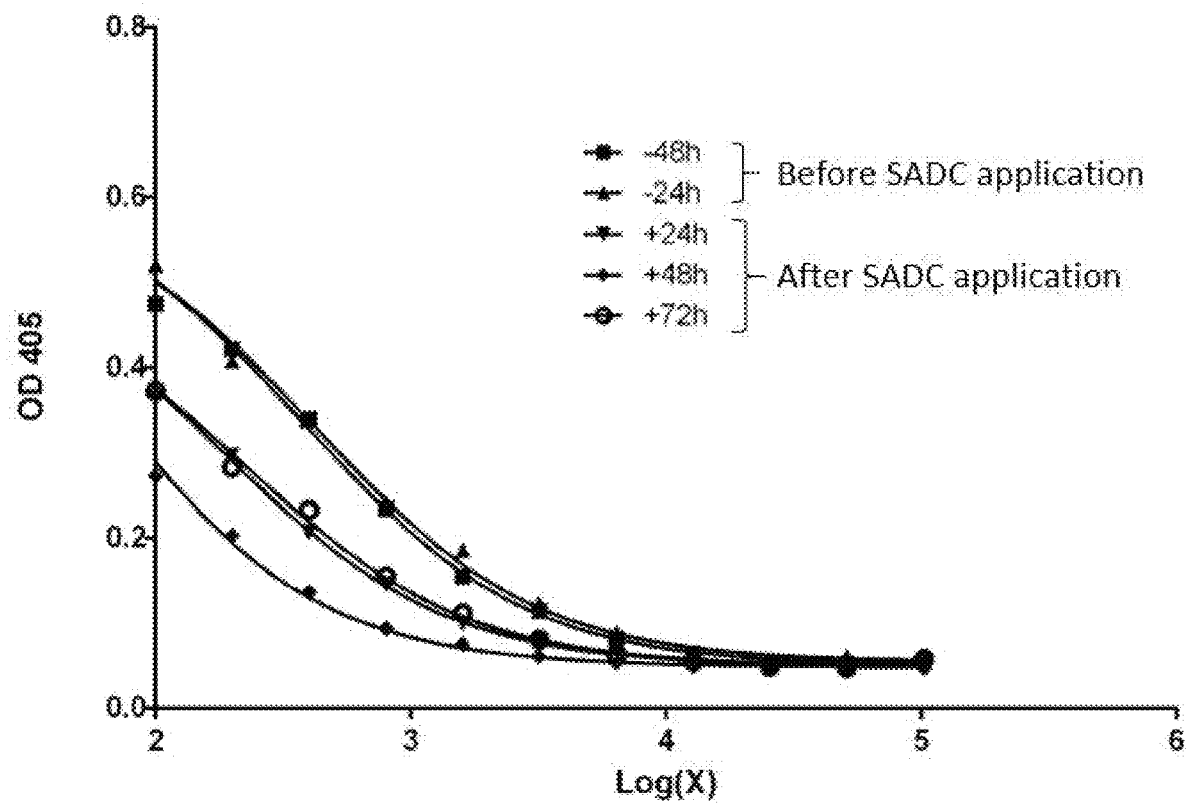
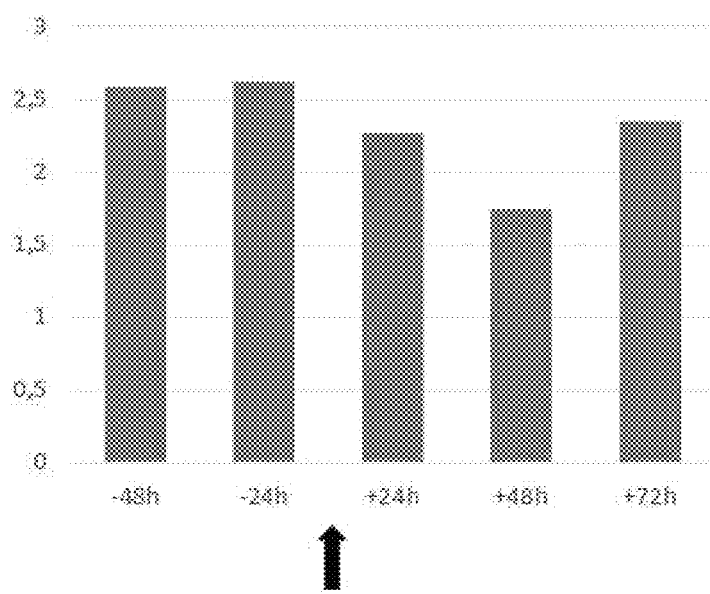
Cont. Fig. 1

D
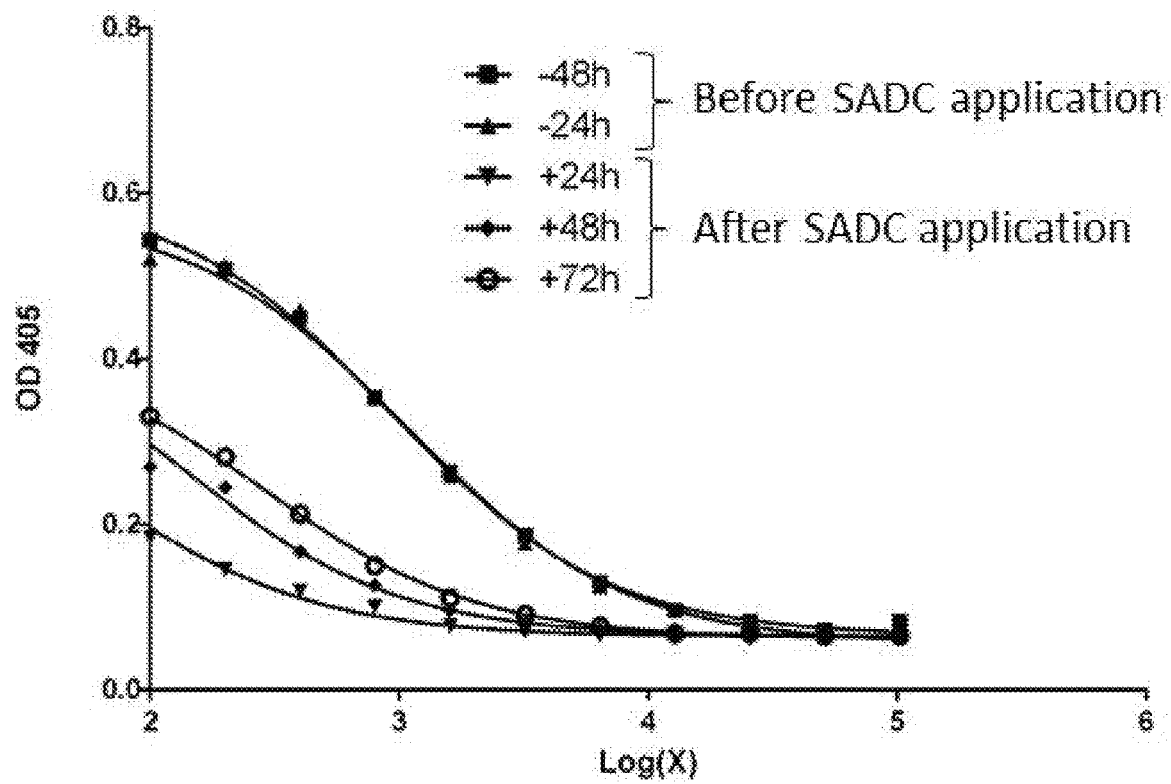
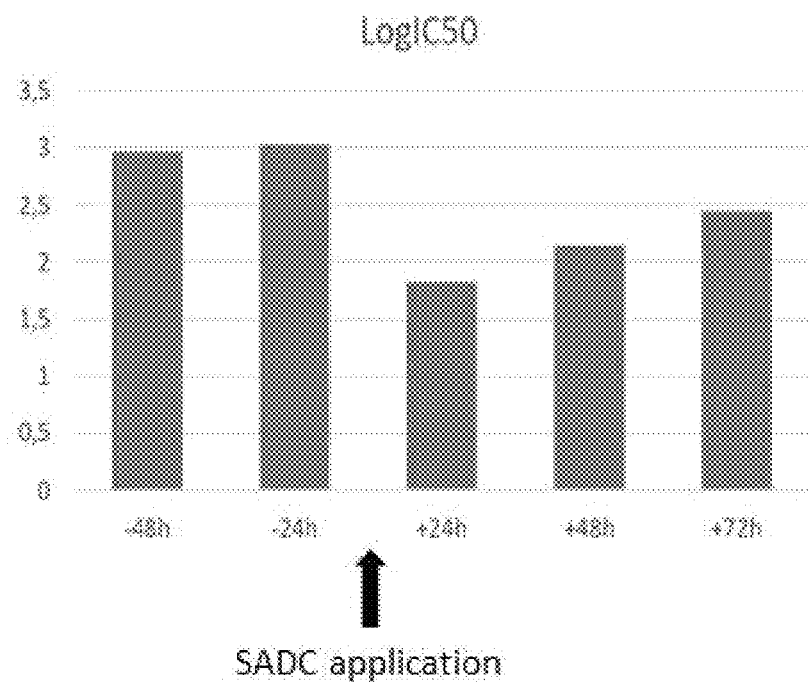
Cont. Fig. 1

E
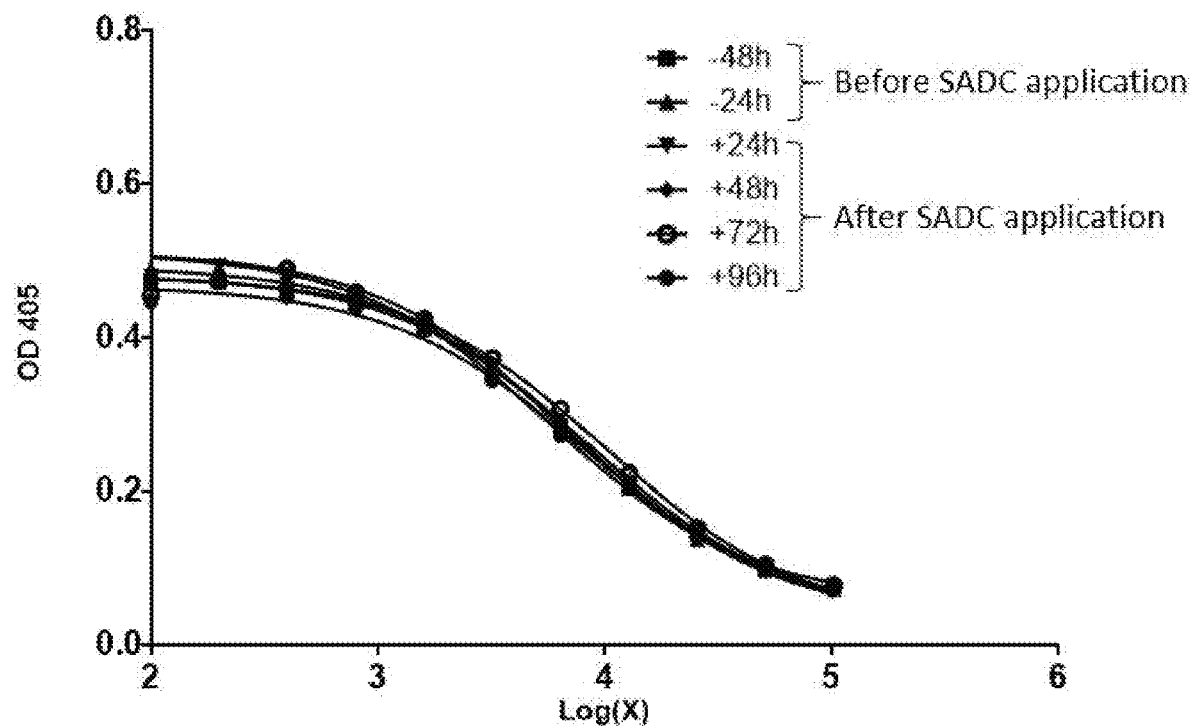
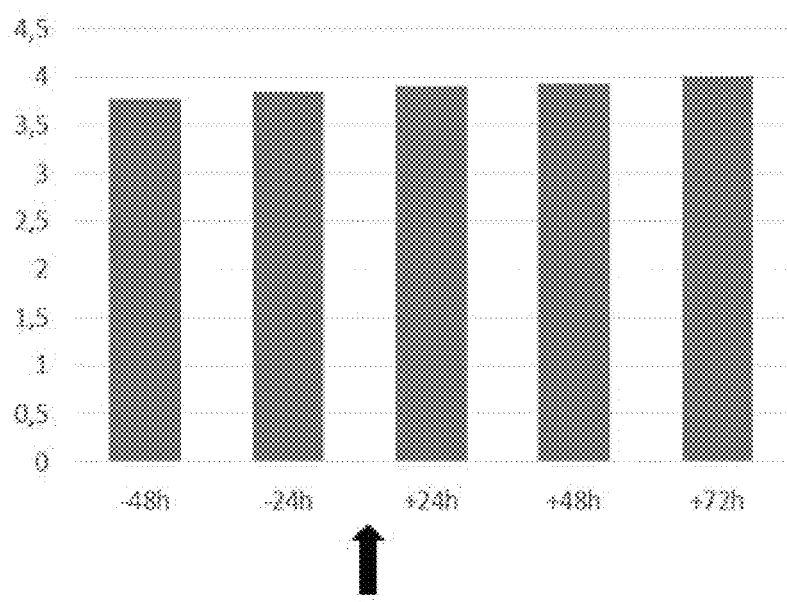
Cont. Fig. 1

COMPOUND FOR THE SEQUESTRATION OF UNDESIRABLE ANTIBODIES IN A PATIENT

CROSS-REFERENCE TO RELATED APPLICATIONS

This application is a continuation application of U.S. patent application Ser. No. 17/424,791, filed Jul. 21, 2021 and which is a U.S. National Stage Application of PCT/EP2020/058024 assigned international filing date of Mar. 23, 2020 and claiming foreign priority to EP patent application 19164784.1 filed Mar. 23, 2019, the disclosure of all these applications is herein incorporated by reference.

INCORPORATION BY REFERENCE OF THE SEQUENCE LISTING

The content of the ASCII text file of the sequence listing named 18Z0488.TXT, 6 kb in size, created on Aug. 3, 2021, is incorporated herein by reference in its entirety.

TECHNICAL FIELD

The field of present invention relates to compounds for the sequestration of undesirable antibodies in an individual, such as antibodies related to autoimmune diseases.

BACKGROUND

In general, antibodies are essential components of the humoral immune system, offering protection from infections by foreign organisms including bacteria, viruses, fungi or parasites. However, under certain circumstances—including autoimmune diseases, organ transplantation, blood transfusion or upon administration of biomolecular drugs or gene delivery vectors—antibodies can target the patient's own body (or the foreign tissue or cells or the biomolecular drug or vector just administered), thereby turning into harmful or disease-causing entities. Certain antibodies can also interfere with probes for diagnostic imaging. In the following, such antibodies are generally referred to as "undesired antibodies" or "undesirable antibodies".

With few exceptions, selective removal of undesired antibodies has not reached clinical practice. It is presently restricted to very few indications: One of the known techniques for selective antibody removal (although not widely established) is immunoapheresis. In contrast to Immunoapheresis (which removes Immunoglobulin), selective immunoapheresis involves the filtration of plasma through an extracorporeal, selective antibody-adsorber cartridge that will deplete the undesired antibody based on selective binding to its antigen binding site. Selective immunoapheresis has for instance been used for removing anti-A or anti-B antibodies from the blood prior to AB0-incompatible transplantation or with respect to indications in transfusion medicine (Teschner et al). Selective apheresis was also experimentally applied in other indications, such as neuroimmunological indications (Tetala et al) or myasthenia gravis (Lazaridis et al), but is not yet established in the clinical routine. One reason that selective immunoapheresis is only hesitantly applied is the fact that it is a cost intensive and cumbersome intervention procedure that requires specialized medical care. Moreover it is not known in the prior art how to deplete undesired antibodies rapidly and efficiently.

Unrelated to apheresis, Morimoto et al. discloses dextran as a generally applicable multivalent scaffold for improving immunoglobulin-binding affinities of peptide and peptidomimetic ligands such as the FLAG peptide. WO 2011/130324 A1 relates to compounds for prevention of cell injury. EP 3059244 A1 relates to a C-met protein agonist.

As mentioned, apheresis is applied extracorporeally. By contrast, also several approaches to deplete undesirable antibodies intracorporeally were proposed in the prior art, mostly in connection with certain autoimmune diseases involving autoantibodies or anti-drug antibodies:

Lorentz et al discloses a technique whereby erythrocytes are charged in situ with a tolerogenic payload driving the deletion of antigen-specific T cells. This is supposed to ultimately lead to reduction of the undesired humoral response against a model antigen. A similar approach is proposed in Pishesha et al. In this approach, erythrocytes are loaded ex vivo with a peptide-antigen construct that is covalently bound to the surface and reinjected into the animal model for general immunotolerance induction.

WO 92/13558 A1 relates to conjugates of stable nonimmunogenic polymers and analogs of immunogens that possess the specific B cell binding ability of the immunogen and which, when introduced into individuals, induce humoral anergy to the immunogen. Accordingly, these conjugates are disclosed to be useful for treating antibody-mediated pathologies that are caused by foreign- or self-immunogens. In this connection, see also EP 0498658 A2.

Taddeo et al discloses selectively depleting antibody producing plasma cells using anti-CD138 antibody derivatives fused to an ovalbumin model antigen thereby inducing receptor crosslinking and cell suicide in vitro selectively in those cells that express the antibody against the model antigen.

Apitope International NV (Belgium) is presently developing soluble tolerogenic T-cell epitope peptides which may lead to expression of low levels of co-stimulatory molecules from antigen presenting cells inducing tolerance, thereby suppressing antibody response (see e.g. Jansson et al). These products are currently under preclinical and early clinical evaluation, e.g. in multiple sclerosis, Grave's disease, intermediate uveitis, and other autoimmune conditions as well as Factor VIII intolerance.

Similarly, Selecta Biosciences, Inc. (USA) is currently pursuing strategies of tolerance induction by so-called Synthetic Vaccine Particles (SVPs). SVP-Rapamycin is supposed to induce tolerance by preventing undesired antibody production via selectively inducing regulatory T cells (see Mazor et al).

Mingozzi et al discloses decoy adeno-associated virus (AAV) capsids that adsorb antibodies but cannot enter a target cell.

WO 2015/136027 A1 discloses carbohydrate ligands presenting the minimal Human Natural Killer-1 (HNK-1) epitope that bind to anti-MAG (myelin-associated glycoprotein) IgM antibodies, and their use in diagnosis as well as for the treatment of anti-MAG neuropathy. WO 2017/046172 A1 discloses further carbohydrate ligands and moieties, respectively, mimicking glycoepitopes comprised by glycosphingolipids of the nervous system which are bound by anti-glycan antibodies associated with neurological diseases. The document further relates to the use of these carbohydrate ligands/moieties in diagnosis as well as for the treatment of neurological diseases associated with anti-glycan antibodies.

US 2004/0258683 A1 discloses methods for treating systemic lupus erythematosus (SLE) including renal SLE and methods of reducing risk of renal flare in individuals with SLE, and methods of monitoring such treatment. One disclosed method of treating SLE including renal SLE and reducing risk of renal flare in an individual with SLE involves the administration of an effective amount of an agent for reducing the level of anti-double-stranded DNA (dsDNA) antibody, such as a dsDNA epitope as in the form of an epitope-presenting carrier or an epitope-presenting valency platform molecule, to the individual.

U.S. Pat. No. 5,637,454 relates to assays and treatments of autoimmune diseases. Agents used for treatment might include peptides homologous to the identified antigenic, molecular mimicry sequences. It is disclosed that these peptides could be delivered to a patient in order to decrease the amount of circulating antibody with a particular specificity.

US 2007/0026396 A1 relates to peptides directed against antibodies, which cause cold-intolerance, and the use thereof. It is taught that by using the disclosed peptides, in vivo or ex vivo neutralization of undesired autoantibodies is possible. A comparable approach is disclosed in WO 1992/014150 A1 or in WO 1998/030586 A2.

WO 2018/102668 A1 discloses a fusion protein for selective degradation of disease-causing or otherwise undesired antibodies. The fusion protein (termed "Seldeg") includes a targeting component that specifically binds to a cell surface receptor or other cell surface molecule at near-neutral pH, and an antigen component fused directly or indirectly to the targeting component. Also disclosed is a method of depleting a target antigen-specific antibody from a patient by administering to the patient a Seldeg having an antigen component configured to specifically bind the target antigen-specific antibody.

WO 2015/181393 A1 concerns peptides grafted into sunflower-trypsin-inhibitor-(SFTI-) and cyclotide-based scaffolds. These peptides are disclosed to be effective in autoimmune disease, for instance citrullinated fibrinogen sequences that are grafted into the SFTI scaffold have been shown to block autoantibodies in rheumatoid arthritis and inhibit inflammation and pain. These scaffolds are disclosed to be non-immunogenic.

Erlandsson et al discloses in vivo clearing of idiotypic antibodies with anti-idiotypic antibodies and their derivatives.

Berlin Cures Holding AG (Germany) has proposed an intravenous broad spectrum neutralizer DNA aptamer (see e.g. WO 2016/020377 A1 and WO 2012/000889 A1) for the treatment of dilated cardiomyopathy and other GPCR-autoantibody related diseases that in high dosage is supposed to block autoantibodies by competitive binding to the antigen binding regions of autoantibodies. In general, aptamers did not yet achieve a breakthrough and are still in a preliminary stage of clinical development. The major concerns are still biostability and bioavailability, constraints such as nuclease sensitivity, toxicity, small size and renal clearance. A particular problem with respect to their use as selective antibody antagonists are their propensity to stimulate the innate immune response.

WO 00/33887 A2 discloses methods for reducing circulating levels of antibodies, particularly disease-associated antibodies. The methods entail administering effective amounts of epitope-presenting carriers to an individual. In addition, ex vivo methods for reducing circulating levels of antibodies are disclosed which employ epitope-presenting carriers.

U.S. Pat. No. 6,022,544 A relates to a method for reducing an undesired antibody response in a mammal by administering to the mammal a non-immunogenic construct which is free of high molecular weight immunostimulatory molecules. The construct is disclosed to contain at least two copies of a B cell membrane immunoglobulin receptor epitope bound to a pharmaceutically acceptable non-immunogenic carrier.

However, the approaches to deplete undesirable antibodies intracorporeally disclosed in the prior art have many shortcomings. In particular, neither of them has been approved for regular clinical use.

SUMMARY

It is thus an object of the present invention to provide improved compounds and methods for intracorporeal depletion (or sequestration) of undesired antibodies (such as antibodies related to autoimmune disease) in an individual, in particular for use in treatment or prevention of a disease or condition related to the undesired antibody (e.g. of autoimmune disease).

The present invention provides a compound comprising
a biopolymer scaffold and at least
a first peptide n-mer of the general formula:

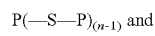 and a second peptide n-mer of the general formula:

Independently for each occurrence, P is a peptide with a sequence length of 2-13 amino acids, preferably 3-11 amino acids, more preferably 4-9 amino acids, especially 5-8 amino acids, and S is a non-peptide spacer. Independently for each of the peptide n-mers, n is an integer of at least 1, preferably of at least 2, more preferably of at least 3, even more preferably of at least 4, especially of at least 5. Each of the peptide n-mers is bound to the biopolymer scaffold, preferably via a linker each.

Preferably, at least one occurrence of P is $P_a$ and/or at least one occurrence of P is $P_b$. $P_a$ is a defined peptide (i.e. a peptide of defined sequence) with a sequence length of 2-13 amino acids, preferably 3-11 amino acids, more preferably 4-9 amino acids, especially 5-8 amino acids. $P_b$ is a defined peptide (i.e. a peptide of defined sequence) with a sequence length of 2-13 amino acids, preferably 3-11 amino acids, more preferably 4-9 amino acids, especially 5-8 amino acids.

The present invention also provides a compound comprising
a biopolymer scaffold and at least
a first peptide n-mer which is a peptide dimer of the formula $P_a$—S—$P_a$ or $P_a$—S—$P_b$, wherein $P_a$ is a defined peptide (i.e. a peptide of defined sequence) with a sequence length of 2-13 amino acids, preferably 3-11 amino acids, more preferably 4-9 amino acids, especially 5-8 amino acids, $P_b$ is a defined peptide (i.e. a peptide of defined sequence) with a sequence length of 2-13 amino acids, preferably 3-11 amino acids, more preferably 4-9 amino acids, especially 5-8 amino acids, and S is a non-peptide spacer, wherein the first peptide n-mer is bound to the biopolymer scaffold, preferably via a linker.

This compound preferably comprises a second peptide n-mer which is a peptide dimer of the formula $P_b$—S—$P_b$ or $P_a$—S—$P_b$, wherein the second peptide n-mer is bound to the biopolymer scaffold, preferably via a linker.

The present invention further provides a compound, preferably for the sequestration (or depletion) of anti human muscle nicotinic acetylcholine receptor (AChR) antibodies, anti human muscle-specific receptor tyrosine kinase antibodies and/or anti human low-density lipoprotein receptor related protein 4 antibodies present in a human individual, the compound comprising a biopolymer scaffold and at least two peptides with a sequence length of 7-13 amino acids, wherein each of the peptides independently comprises a 7-13 amino-acid sequence fragment of the AChR subunit alpha sequence identified by UniProt accession code P02708 (optionally wherein the sequence fragment comprises at most five, preferably at most four, more preferably at most three, even more preferably at most two, especially at most one amino acid substitutions (e.g. such that a mimotope is formed)) or of the muscle-specific receptor tyrosine kinase sequence identified by UniProt accession code O15146 or of the low-density lipoprotein receptor related protein 4 sequence identified by UniProt accession code O75096 (optionally wherein the sequence fragment comprises at most five, preferably at most four, more preferably at most three, even more preferably at most two, especially at most one amino acid substitutions (e.g. such that a mimotope is formed)), wherein the peptides are covalently bound to the biopolymer scaffold, preferably via a linker, wherein the biopolymer scaffold is selected from the group consisting of human globulins and human albumin.

The present invention also provides a compound, preferably for the sequestration (or depletion) of anti-Epstein-Barr virus nuclear antigen 1 (EBNA-1) antibodies, anti human melatonin-related receptor (GPR50) antibodies and/or anti human type-1 angiotensin II receptor (AT1AR) antibodies present in a human individual, the compound comprising a biopolymer scaffold and at least two peptides with a sequence length of 7-13 amino acids, wherein each of the peptides independently comprises a 7-13 amino-acid sequence fragment of the EBNA1 sequence identified by UniProt accession code Q1HVF7 or P03211 or of the GPR50 sequence identified by UniProt accession code Q13585 or of the type-1 angiotensin II receptor (AT1AR) sequence identified by UniProt accession code P30556, wherein the peptides are covalently bound to the biopolymer scaffold, preferably via a linker, wherein the biopolymer scaffold is selected from the group consisting of human globulins, preferably from the group consisting of human immunoglobulins and human haptoglobin, and human albumin.

Furthermore, the present invention provides a pharmaceutical composition comprising any one of the aforementioned compounds and at least one pharmaceutically acceptable excipient. Preferably, this pharmaceutical composition is for use in therapy, in particular of any one of the diseases or conditions mentioned herein.

In another aspect, the present invention provides a method of sequestering (or depleting) one or more antibodies present in an individual, comprising obtaining a pharmaceutical composition as defined herein, the composition being non-immunogenic in the individual, where the one or more antibodies present in the individual are specific for at least one occurrence of P, or for peptide $P_a$ and/or peptide $P_b$; and administering the pharmaceutical composition to the individual.

In yet another aspect, the present invention relates to a pharmaceutical composition, comprising the compound defined herein and further comprising an active agent and optionally at least one pharmaceutically acceptable excipient. The active agent comprises a peptide fragment with a sequence length of 2-13 amino acids, preferably 3-11 amino acids, more preferably 4-9 amino acids, especially 5-8 amino acids. The sequence of at least one occurrence of peptide P, or peptide $P_a$ and/or peptide $P_b$, of the compound is at least 70% identical, preferably at least 75% identical, more preferably at least 80% identical, yet more preferably at least 85% identical, even more preferably at least 90% identical, yet even more preferably at least 95% identical, especially completely identical to the sequence of said peptide fragment. Preferably, this pharmaceutical composition is for use in prevention or inhibition of an immune reaction against the active agent.

In even yet another aspect, the present invention provides a method of inhibiting an immune reaction to a treatment with an active agent in an individual in need of treatment with the active agent, comprising obtaining said pharmaceutical composition comprising the compound and the active agent; wherein the compound of the pharmaceutical composition is non-immunogenic in the individual, and administering the pharmaceutical composition to the individual.

In a further aspect, the present invention provides a method of providing the compound of the invention, comprising the steps of identifying at least one individual having an undesired antibody against an antigen, screening a peptide library to identify a peptide mimotope for which the undesired antibody is specific, and providing the compound, wherein at least one occurrence of P of the compound comprises the entire sequence of the peptide mimotope.

In the course of the present invention, it was surprisingly found that the compound of the present invention is particularly effective in reducing titres of undesired antibodies in an individual. In particular, the compound achieved especially good results with regard to selectivity, duration of titre reduction and/or level of titre reduction in an in vivo model (see experimental examples).

DETAILED DESCRIPTION

The detailed description given below relates to all of the above aspects of the invention unless explicitly excluded.

Intracorporeal depletion of undesired antibodies (as achieved by the present invention) is for example advantageous in autoimmune diseases, organ- and cell transplantation, blood transfusion, or with respect to antibodies that are directed against biotherapeutics, substitution therapeutics or viral gene delivery vectors (such as AAV) or even in diagnostic imaging or in emergency intervention following antibody treatment or active vaccination. In particular, with respect to autoimmune diseases, several hundreds of autoimmune conditions are connected to autoantibodies that bind to defined self-epitopes or neoepitopes present in the body. There appears to be practically no restriction with respect to organs or tissues that can be affected by disease-causing autoantibodies: Table 1 below lists some examples to illustrate the diversity of indication fields where it is beneficial to target undesired antibodies selectively.

TABLE 1

Exemplary list of applications of the present invention:

| AUTOIMMUNE DISEASES | ANTI-DRUG and NEUTRALIZING ANTIBODIES |
|---|---|
| CNS & Muscle | ADAs/nABs against coagulation factors |
| MOG seropositive neuromyelitis optica spectrum disorders | ADAs/nABs against enzymes |
| Neuromyelitis Optica | ADAs/nABs against growth factors and hormones |
| Autoimmune-Encephalitis | ADAs/nABs against fusion proteins and decoy receptor drugs |
| Multiple Sclerosis | TRANSPLANTATION and TRANSFUSION MEDICINE |
| Amyotrophic Lateral Sclerosis | |

TABLE 1-continued Exemplary list of applications of the present invention:

| | |
|---|---|
| SLE dementia | Alloantibodies |
| Myasthenia gravis | Blood group antibodies |
| Heart & Organs: | AB0-incompatible |
| Dilatative Cardiomyopathy, | organ Transplantation |
| pulmonary hypertension | EMERGENCY INTERVENTION |
| Chagas' Disease | Active vaccine intervention |
| other diseases with | (therapeutic vaccines) |
| β1-adrenergic receptors | Passive vaccine intervention |
| Primary biliary cholangitis | (therapeutic mABs) |
| Sjögren's Syndrome | Cytokine Release Syndrome |
| Caeliac Disease | (e.g. After CART treatment) |
| Graves Disease | VIRAL VECTORS |
| Goodpasture Disease | IN GENE THERAPY |
| Systemic conditions: | IN VIVO |
| Systemic Lupus | DIAGNOSTIC IMAGING |
| Erythematosus | |
| Sjögren's syndrome | |
| Systemic Sclerosis | |
| Behcet's Disease | |
| Hypertension | |
| type I Diabetes | |
| type II Diabetes | |
| Preeclampsia | |
| Blood: | |
| Immune | |
| Thrombocytopenic | |
| Purpura (ITP) | |
| Skin: | |
| pemphigus vulgaris | |
| bullous pemphigoid | |
| Epidermolysis bullosa | |
| acquista and bullous SLE | |

For instance, in transplantation medicine, undesired alloantibodies may occur. Alloantibodies are antibodies directed against foreign tissue antigens which can contribute to accelerated transplant rejection after transplantation (Garces et al, 2017). Upon tissue-, bone marrow- and stem cell transplantation, foreign tissue antigens are recognized by T-cells and B-cells producing antibodies against major and minor histocompatibility antigens. Inverse correlation between transplant survival and alloantibody levels confirms the pathogenic role of alloantibodies. Further, depletion of undesired blood group antibodies before and after AB0-incompatible transplantation of organs have been shown to be beneficial to transplant survival (Rummler et al, 2016).

Anti-drug Antibodies (ADAs), sometimes also referred to as neutralizing antibodies (nABs), are a category of undesired antibodies having emerged with the advent of biological drugs carrying epitopes that are recognized as "foreign" thereby inducing an anti-drug antibody response. This immune response can induce neutralizing antibodies (e.g. acting by depletion or blocking of the drug, or by forming immunocomplexes), a phenomenon that correlates with the amount of "foreign" sequences of the drug, inherent immunogenicity of the drug and, importantly, with the propensity to aggregate and to form complexes, once the drug is in the plasma (Moussa et al, 2016). Examples of drugs inducing ADAs include certain antibodies such as anti TNF-alpha antibodies, substitution therapeutics such as Hemophilia Factor VIII or enzymes used in enzyme replacement therapies such as Fabry Disease or such as uricase for the treatment of refractory gout and other classes of biological therapeutics such as e.g. erythropoietin or interferon.

Similar to the situation with ADAs, pre-existing or induced undesired antibodies against gene therapy vectors are an emerging problem in the field of gene therapy (see e.g. Mingozzi & High, 2017): Gene therapy is rapidly progressing and Adeno Associated Viruses (AAV) but also other viral vector gene delivery vectors show promising preclinical and clinical results. This is particularly important for hematologic diseases such as hemophilia, or in Gaucher disease, porphyria or hemochromatosis or several other genetic diseases with enzyme defects. Much effort has been invested into optimization of AAV vectors, however the problem of pre-existing antibodies or newly induced antibodies against the vector, but also their T-cell immunogenicity is not yet solved. Several strategies to overcome B-cell and T-cell immunity were proposed including serological pre-selection of the target patients eligible for AAV treatment, high vector dosing, capsid decoys that pre-adsorb or deplete pre-existing or newly induced anti AAV antibodies, co-administration of decoy T-cell receptors or less selective approaches such as concomitant immunosuppression. The more pragmatic approaches were AAV serotype switching, plasma exchange therapies, selective immunoapheresis or local application of AAV vectors. Essentially, the immunological strategies boiled down to immunosuppression or tolerance induction. However, none of these strategies could solve the problem of pre-existing neutralizing anti AAV antibodies satisfactorily (see e.g. Majowicz et al.). The main disadvantage of the capsid decoy strategy was that empty capsids were processed by target cells similar to intact AAV particles, thereby facilitating antigen presentation by MHC I and stimulation of T-cells ultimately providing an immunostimulatory effect.

More than 2000 clinical trials for gene therapy (mostly clinical phase I or II trials) were undertaken during the last years. Monogenetic diseases still constitute a significant portion of the typical indications for gene-based therapies. They include a great diversity of indication fields, such as primary immunodeficiencies, inherited neurological disorders, cystic fibrosis, ocular disorders, hemoglobinopathies, hemophilias, alpha-1-antitrypsin deficiencies, lipoprotein lipase deficiency, enzyme defects, and many others. Other formats of gene therapy-based strategies such as Chimeric Antigen Receptor T-Cells (CAR T-Cells) evolve rapidly but still carry the risk for humoral responses against functional components of the system, such as switches, suicide gene products or other non-self and modified protein components, or against the viral gene delivery components or neo-antigens emerging by uncontrolled gene insertions into protein coding sequences. Mechanistically, gene therapy includes gene repair strategies, genome editing technologies and stable or transient gene expression strategies. As mentioned above, a common challenge remains that patients carry pre-existing neutralizing antibodies against viral gene therapy vectors that reduce the efficacy. Importantly, viral gene therapy vectors are often capable of inducing T-cell responses and neutralizing antibodies against viral proteins and their products. In addition, antibody- or T-cell responses can be introduced against the gene product itself or against the introduced DNA editing machinery such as components of the CRISPR/Cas9 containing natural or artificially modified endonucleases (such as prototype Cas9) that can be applied for therapeutic genome editing. Therefore, neutralizing antibodies that affect gene therapy efficacy remain a major challenge in the field of viral gene therapy vector development, in particular when using AAVs, lentiviruses or retroviruses.

Finally, in the context of safety intervention in active immunization trials (i.e. therapeutic vaccination) or passive treatments with antibodies or antibody-like compounds, interventional drugs for rapid selective antibody removal of e.g. therapeutic antibodies or antibody-like biotherapeutic compounds that cause complications under emergency conditions are needed. For these situations, there is especially a lack of rapid and effective selective antibody lowering strategies.

In response to the lack of satisfactory therapeutic strategies that can rapidly and safely remove undesired antibodies such as e.g. myasthenia gravis during a myasthenic crisis, before administration of a substitution therapeutic, before applying a gene targeting vector or in case of an adverse event induced by a therapeutic antibody or any antibody-like biological compound, the present invention provides a particularly suitable solution. The present invention represents a platform for flexible, optionally personalized, biotherapeutics that can be adapted to any type of undesired or harmful polyclonal or monoclonal antibody. In particular, these biotherapeutics can remove undesired antibodies rapidly, making them suitable for urgent interventions.

The biopolymer scaffold used in the present invention may be a mammalian biopolymer such as a human biopolymer, a non-human primate biopolymer, a sheep biopolymer, a pig biopolymer, a dog biopolymer or a rodent biopolymer. In particular the biopolymer scaffold is a protein, especially a (non-modified or non-modified with respect to its amino-acid sequence) plasma protein. Preferably, the biopolymer scaffold is a mammalian protein such as a human protein, a non-human primate protein, a sheep protein, a pig protein, a dog protein or a rodent protein. Typically, the biopolymer scaffold is a non-immunogenic and/or non-toxic protein that preferably circulates in the plasma of healthy (human) individuals and can e.g. be efficiently scavenged or recycled by scavenging receptors, such as e.g. present on myeloid cells or on liver sinusoidal endothelial cells (reviewed by Sorensen et al 2015).

According to a particular preference, the biopolymer scaffold is a (preferably human) globulin, preferably selected from the group consisting of immunoglobulins, alpha1-globulins, alpha2-globulins and beta-globulins, in particular immunoglobulin G, haptoglobin and transferrin. Haptoglobin in particular has several advantageous properties, as shown in Examples 5-9, especially an advantageous safety profile.

The biopolymer scaffold may also be (preferably human) albumin, hemopexin, alpha-1-antitrypsin, C1 esterase inhibitor, lactoferrin or non-immunogenic (i.e. non-immunogenic in the individual to be treated) fragments of all of the aforementioned proteins, including the globulins.

The peptides (or peptide n-mers) are preferably covalently conjugated (or covalently bound) to the biopolymer scaffold via a (non-immunogenic) linker known in the art such as for example amine-to-sulfhydryl linkers and bifunctional NHS-PEG-maleimide linkers or other linkers known in the art. Alternatively, the peptides (or peptide n-mers) can be bound to the epitope carrier scaffold e.g. by formation of a disulfide bond between the protein and the peptide (which is also referred to as "linker" herein), or using non-covalent assembly techniques, spontaneous isopeptide bond formation or unnatural amino acids for bio-orthogonal chemistry via genetic code expansion techniques (reviewed by Howarth et al 2018 and Lim et al 2016).

The compound of the present invention may comprise e.g. at least two, preferably between 3 and 40 copies of one or several different peptides (which may be present in different forms of peptide n-mers as disclosed herein). The compound may comprise one type of epitopic peptide (in other words: antibody-binding peptide or paratope-binding peptide), however the diversity of epitopic peptides bound to one biopolymer scaffold molecule can be a mixture of e.g. up to 8 different epitopic peptides.

Typically, since the peptides present in the inventive compound specifically bind to selected undesired antibodies, their sequence is usually selected and optimized such that they provide specific binding in order to guarantee selectivity of undesired antibody depletion from the blood. For this purpose, the peptide sequence of the peptides typically corresponds to the entire epitope sequence or portions of the undesired antibody epitope. The peptides used in the present invention can be further optimized by exchanging one, two or up to four amino-acid positions, allowing e.g. for modulating the binding affinity to the undesired antibody that needs to be depleted. Such single or multiple amino-acid substitution strategies that can provide "mimotopes" with increased binding affinity and are known in the field and were previously developed using phage display strategies or peptide microarrays (see e.g. Application Note, "T PEPper-MAP® Full Substitution Scan of HA and M13 Epitopes", by PEPperPRINT GmbH, Heidelberg, Germany). In other words, the peptides used in the present invention do not have to be completely identical to the native epitope sequences of the undesired antibodies.

Typically, the peptides used in the compound of the present invention (e.g. peptide P or $P_a$ or $P_b$ or $P_1$ or $P_2$) are composed of one or more of the 20 amino acids commonly present in mammalian proteins. In addition, the amino acid repertoire used in the peptides may be expanded to post-translationally modified amino acids e.g. affecting antigenicity of proteins such as post translational modifications, in particular oxidative post translational modifications (see e.g. Ryan 2014) or modifications to the peptide backbone (see e.g. Müller 2018), or to non-natural amino acids (see e.g. Meister et al 2018). These modifications may also be used in the peptides e.g. to adapt the binding interaction and specificity between the peptide and the variable region of an undesired antibody. In particular, epitopes (and therefore the peptides used in the compound of the present invention) can also contain citrulline as for example in autoimmune diseases. Furthermore, by introducing modifications into the peptide sequence the propensity of binding to an HLA molecule may be reduced, the stability and the physicochemical characteristics may be improved or the affinity to the undesired antibody may be increased.

In many cases, the undesired antibody that is to be depleted is oligo- or polyclonal (e.g. autoantibodies, ADAs or alloantibodies are typically poly- or oligoclonal), implying that undesired (polyclonal) antibody epitope covers a larger epitopic region of a target molecule. To adapt to this situation, the compound of the present invention may comprise a mixture of two or several epitopic peptides (in other words: antibody-binding peptides or paratope-binding peptides), thereby allowing to adapt to the polyclonality or oligoclonality of an undesired antibody.

Such poly-epitopic compounds of the present invention can effectively deplete undesired antibodies and are more often effective than mono-epitopic compounds in case the epitope of the undesired antibody extends to larger amino acid sequence stretches.

It is advantageous if the peptides used for the inventive compound are designed such that they will be specifically recognized by the variable region of the undesired antibodies to be depleted. The sequences of peptides used in the present invention may e.g. be selected by applying fine epitope mapping techniques (i.e. epitope walks, peptide deletion mapping, amino acid substitution scanning using peptide arrays such as described in Carter et al 2004, and Hansen et al 2013) on the undesired antibodies.

Preferably, the peptide used for the inventive compound (e.g. peptide P or $P_a$ or $P_b$) comprises an epitope or epitope part (e.g. at least two, preferably at least three, more preferably at least four, even more preferably at least five, yet even more preferably at least six, especially at least seven or even at least eight amino acids) of one of the following antigens (involved in autoimmune diseases) identified by their UniProt accession code:

P01023, A8K2U0, P49588, Q5JTZ9, O95477, Q8IZY2, P08183, P33527, O15438, Q961U4, P00519, P42684, Q9BYF1, P22303, Q99798, P68133, P60709, P63261, P12814, O43707, P61158, Q13705, P37023, O75077, Q9UKQ2, Q76LX8, Q6ZMM2, P35611, P07327, P00325, P35348, P25100, P08588, P07550, P25098, P35626, P30566, P43652, P02771, Q5U5Z8, Q15109, P35573, Q9UL18, Q9UKV8, O00468, P01019, P30556, Q09666, P02765, O43918, Q9Y6K8, Q02952, P14550, P15121, O95154, P02768, P00352, P49189, Q9UM73, P09923, P05187, P03971, P49418, P03950, Q9BY76, Q15327, P15144, P04083, P50995, P07355, Q3ZCQ2, P12429, P09525, P08758, P08133, O76027, Q13367, P27695, Q9BZZ5, P02647, P04114, P02749, P05067, P29972, P55087, Q8N726, P05089, Q9UNA1, P52566, Q99819, Q15052, P07306, P04424, P08243, Q9BXN1, P15336, P13637, P05026, P98194, P20648, P51164, P06576, P48047, P54252, Q8WXX7, P01185, P25311, Q9H6S1, P61769, Q13072, O75531, Q99728, P10415, P41182, P11274, O14503, Q93088, O00499, O15392, P35226, P12643, P18075, Q8N8U9, Q13873, P17213, Q9NP55, Q96DR5, Q8TDL5, P15056, Q7Z569, P38398, P51587, Q58F21, Q8IWQ3, Q8NE79, Q9Y224, Q13901, P02745, P01024, P00915, P00918, P07451, O00555, Q00975, Q9NY47, Q9Y698, Q8TC20, Q05682, P27482, P27797, P27824, P04632, P52907, P42574, Q14790, P31415, P41180, P20810, O15446, P04040, Q9NTU7, Q5M9NO, Q3V6T2, P10147, P13501, P20248, P14635, P24385, Q8ND76, P51681, P49368, P48643, P50990, Q9NZQ7, P28906, P16671, P04234, P15529, P08174, P13987, P01732, P21926, P30305, P12830, P55291, P22223, P55283, P06493, P42771, P51861, Q01850, Q9H211, P13688, P06731, Q9UNI1, P49450, P07199, Q03188, Q02224, P49454, Q9H3R5, Q92674, Q6IPU0, Q7L2Z9, A8MT69, Q5JTW2, P00751, P08603, Q03591, P36980, Q02985, Q9P2M7, O95992, Q14839, P10645, P36222, Q15782, Q9UKJ5, Q9Y259, P11229, P08172, P20309, P08173, P08912, P02708, Q9UGM1, P11230, Q8NCH0, Q99828, O75339, Q14011, Q07065, P12277, Q96MX0, P06732, A8K714, O95832, O75508, P30622, Q96KN2, Q12860, Q02246, Q8IWV2, O94779, Q9UQ52, P78357, Q9UHC6, Q7Z7A1, P38432, Q5TAT6, Q9UMD9, P02452, Q01955, P29400, Q14031, P12111, Q02388, Q9Y215, P49747, Q14019, P00450, P16870, Q8TCG5, P17927, Q9NS37, Q9UJA2, P02741, P02511, P53674, O95825, O75390, Q9Y600, P04141, P09919, P0DML2, Q14406, Q6UVK1, Q01459, Q9GZU7, P16410, P35222, P53634, P07339, P08311, Q14247, O60494, Q14999, Q86UP6, P61073, P05108, P05093, P04798, P05177, P08686, P11509, P20813, P33261, P11712, P10635, P05181, P08684, Q8N907, P09172, P43146, P07585, P20711, Q16832, Q9NR30, O00571, Q86XP3, Q9NY93, O75398, P35659, P17661, Q96SL1, O94907, P10515, P09622, P36957, P24855, Q8NFT8, O00429, Q8N608, P27487, P42658, Q14195, Q9BPU6, P21728, P14416, Q08554, Q02487, Q14574, Q02413, Q14126, P32926, Q86SJ6, P15924, Q03001, Q9NRD8, Q05923, O75923, O95905, Q9NTX5, Q16610, O43854, P25101, Q15075, P68104, O00418, O95967, P01133, P00533, P20042, P38919, Q04637, P08246, Q12926, Q14576, P26378, P15502, P19622, P06733, P09104, P22413, O43768, P11171, P16422, P07099, P34913, P01588, P11678, P58107, P04626, Q96RT1, Q8IUD2, Q14264, P10768, P03372, Q9Y603, Q92817, Q9Y3B2, Q01780, Q13868, Q9NQT5, Q9NPD3, Q9NQT4, Q5RKV6, Q15024, Q96B26, Q06265, P15311, P00488, P08709, P00451, P00740, P15090, Q14320, P48023, P49327, Q8TES7, P22087, P35555, Q75N90, P09467, P12319, O75015, O75636, Q7L513, P02675, P11362, P62942, Q9UIM3, P20930, Q14315, O75955, Q14254, O43155, P35916, P02751, Q04609, P01225, Q12841, O95954, P02794, P02792, P09958, P35637, P51114, Q9UM11, P35575, O95166, P60520, Q9UBS5, O75899, Q99259, Q05329, Q13065, P22466, Q14376, P04406, P41250, P01350, P15976, P50440, P02774, P01275, Q8N6F7, P23434, P55107, P50395, P56159, Q9UJY5, P01241, P01286, Q9UBU3, P09681, O14908, P29033, Q9NS71, Q6ZMI3, P23415, P15104, Q61B77, P49915, Q13823, P01148, P30968, Q92805, Q08379, Q08378, Q13439, A6NI86, A8MQT2, Q14789, P07359, P55259, P40197, Q9HCN6, P14770, Q9NQX3, P06744, Q13098, P24298, P18283, P42261, P42262, P42263, P48058, O43424, P39086, Q13002, Q16478, Q05586, Q12879, Q13224, Q4V328, Q13255, P41594, P28799, P07492, P08263, P21266, P78417, P09211, Q00403, P35269, P25092, P08236, P02724, P07305, P16104, O75367, P84243, P12081, Q96D42, P68871, Q13547, Q92769, O15379, P56524, Q9UQL6, P19113, Q9UBI9, P51858, Q00341, Q9NRV9, O00291, O75146, P54198, P16402, P58876, P62805, P19367, P09429, P26583, P04035, Q01581, P54868, P05114, P05204, Q14541, P09651, P22626, Q99729, Q14103, P52597, P31943, P31942, P61978, P14866, Q8WVV9, Q9NSC5, Q99714, Q7Z5P4, P14060, P08238, P14625, P0DMV8, P0DMV9, P34932, P11021, P11142, P04792, Q12988, P10809, Q92598, P08908, Q13639, Q9Y4L1, P10997, Q05084, Q9UMF0, O75874, Q5TF58, Q16666, Q9BYX4, P01563, P01574, P01579, Q9NWB7, P05019, P08069, P01344, Q9NZI8, Q9Y6M1, O00425, P11717, P18065, P17936, P01876, P01877, P01854, P01857, P01859, P01860, P01861, A6NGN9, Q8N6C5, P22301, Q13651, Q08334, Q14005, Q16552, Q96PD4, Q14116, P01583, P01584, P14778, P60568, Q9GZX6, P08700, P05112, P05231, P40189, Q96LU5, Q9NV31, P29218, O14732, P12268, Q9NQS7, P01308, Q96T92, P06213, P46940, Q14653, Q13568, P35568, P17301, P08514, P23229, P20701, P11215, P05107, P05106, P16144, Q14643, Q9Y6Y0, O60674, P17275, Q15046, P16389, P22459, Q9UK17, Q9NZI2, Q9NS61, P78508, P48050, P51787, O43525, Q8N513, Q6PI47, P35968, Q9Y4F3, Q96Q89, P43626, P43628, Q5JT82, Q53G59, Q8IXQ5, Q9UKR3, P03952, P26715, P26717, Q13241, P13645, P02533, P19012, P08779, Q04695, P05783, P08727, P12035, Q8N1N4, P05787, Q9NSB2, O15230, P11047, P13473, Q14739, P31025, P13796, P07195, P01130, Q9Y2U8, P09382, P05162, P17931, Q08380, Q3ZCW2, O95970, Q5TDP6, P22888, P49917, P07098, P02545, P20700, Q03252, P61968, P29536, P08519, Q07954, P98164, O75096, Q8TF66, Q32MZ4, Q8ND56, Q9Y4ZO, P02788, Q17RY6, P20645, Q8NHW3, P20916, P43358, O15479, O60732, Q9H0U3, P46821, P11137, Q16584, O43318, P45984, Q16644, P21941, O00339, P56270, P02144, Q9UIS9, P11226, P02686, Q01726, P32245, Q8IVS2, Q99705, Q969V1, Q8TDD5, Q8NE86, P40925, Q00987, O00255, P50579, P46013, Q16655, P03956, P45452, P08253, P09237, P14780, Q13201, Q13875, Q16653, Q13724, Q14149, Q9UBU8, O00566, Q99547, P40238,

P05164, Q00013, Q9NZW5, P25189, P22897, Q9Y605, P82909, P43246, P52701, Q13421, P26038, Q9UJ68, P26927, Q13043, Q04912, Q9NZJ7, Q86UE4, P15941, Q8WX17, O15146, Q9UIF7, P10242, P01106, Q99417, P12524, Q8N699, P12882, P35580, P35749, Q9UKX3, Q7Z406, Q9Y2K3, Q9UKX2, P11055, Q9Y623, P13533, P12883, A7E2Y1, P13535, P35579, B0I1T2, P54296, Q14CX7, E9PAV3, Q13765, Q8WY41, Q96159, Q9UBB6, Q9UHB4, Q00604, P28331, P20929, P07196, P07197, Q8NG66, Q8TD19, O60524, O94856, P01138, Q8N4C6, P30414, P59047, Q8N427, Q13253, Q15155, P29475, P51513, Q9UNW9, P55786, O60500, P06748, P01160, P17342, P01303, Q9Y5X4, Q8IXM6, Q9ULB1, Q9HDB5, Q9Y4CO, Q9NXX6, P04629, Q16620, Q16288, Q02818, P80303, Q14980, P49790, Q8TEM1, O15504, Q14990, Q5BJF6, Q9ULJ1, Q6UX06, P78380, P41143, P35372, Q9P0S3, Q92791, Q9UQ80, Q13310, Q9UM07, Q7Z2X7, Q5JRK9, Q96GU1, Q13177, Q99497, P09874, P40424, Q15154, P12004, P29120, Q8WUM4, O95263, O76083, P16234, P09619, O00330, P30101, Q8N165, O00151, Q5T2W1, P16284, P02776, P10720, P35080, P18669, P00558, O95394, P35232, Q99623, Q9BVI0, Q92576, O43175, P11309, O75364, Q9Y446, P04054, Q13018, P16885, Q15149, Q9H7P9, P40967, P29590, Q01453, Q9NR77, P54277, P16233, P54317, Q8ND90, Q9UL42, P00491, Q9H9Y6, O14802, Q99575, P16435, Q15063, Q01851, Q12837, Q15181, P62937, O60437, P35813, P01298, Q9HAZ2, P32119, Q13162, P30041, P13727, Q92954, P17612, P17252, P01236, P04553, P04554, O60678, P04070, Q9UNN8, P54821, Q99811, P07477, P24158, Q9BXM0, O43653, O75475, P20618, P40306, P49721, P28074, P28062, P28065, P61289, Q6PGN9, P26599, Q8WV60, P01270, P06454, Q06124, Q9Y2R2, P08575, Q12913, Q16849, Q92932, Q86Y79, Q9UHX1, P20472, Q9BRP8, P51153, Q9UI14, Q15276, P63244, Q92878, Q06609, P04049, Q15311, Q9UKM9, Q14498, P38159, P10745, Q06330, P53805, O95199, Q9P258, P35243, P46063, P05451, Q8IX06, P57771, P08100, P12271, O60930, O00584, Q9ULK6, Q99942, Q9UBF6, P13489, O75116, Q01973, P15927, Q9Y2JO, Q9UNE2, Q02878, P05388, P05386, P05387, Q9BUL9, P78346, P78345, P62277, P60866, O75676, O43159, Q15404, O00442, Q92541, Q9NQC3, Q9Y265, Q9Y230, P48443, P21817, Q92736, P31151, P04271, P0DJI8, P0DJI9, P10523, P49591, O43290, Q99590, Q8WTV0, Q14108, P13521, P05408, Q14524, Q9BWW7, P34741, Q86SQ7, Q9UDX4, Q13228, P16109, P04279, Q9HC62, P49908, Q9HD40, P01009, P05543, P30740, P29508, P48594, P35237, P05121, P07093, P05155, Q9BYW2, Q7Z333, Q8N474, Q9BWM7, Q99961, O15266, O60902, Q9NYZ4, Q9Y336, Q9H0K1, Q14190, Q13239, Q14493, Q9H0C2, P12235, P05141, Q9H2B4, O43511, P11168, Q8IWU4, O00400, P08195, Q8IWA5, P48751, Q9Y6R1, Q9BRV3, Q92911, P37840, O76070, P08621, P09012, P14678, P09234, P62314, P62316, P62318, P62304, P62306, P62308, P63162, O14512, P00441, P04179, Q9BQB4, O00570, P56693, P35716, O15370, O60248, Q9UN79, O95416, Q9H6I2, P35713, P48431, Q9Y651, P41225, O94993, Q06945, P35711, P35712, Q9BT81, P57073, P48436, P08047, P23497, Q13342, Q9H930, Q15506, Q8N0X2, P00995, P16150, O43791, P10451, Q8TCT8, Q8TCT7, Q8TCT6, Q13813, Q13501, P10124, P61011, O76094, Q05066, P05455, O43805, P61278, Q13586, Q9P246, P31948, P49842, P16949, Q7Z7C7, Q13033, O75558, P61266, Q13190, Q8IWZ8, Q9Y2ZO, Q8IWU6, P63165, P61956, P17600, P08247, P21579, P37837, Q15633, Q13148, P26639, Q9NYW0, P20226, O60806, P24557, P17987, O60522, O14746, P02787, P05549, Q92734, P10646, P02786, P01266, P01137, P21980, Q08188, P49221, P07204, P40225, P10827, P10828, Q9UPZ6, P31483, P29401, Q9Y490, O60602, Q8TDI7, P17152, P42167, P42166, P01375, O00300, P43489, P19237, P48788, P19429, P13805, P45379, P45378, P09430, Q8NDV7, P11387, Q969P6, P11388, Q13472, O95985, P04637, Q9H3D4, O15350, P60174, P09493, P07202, P12270, P56180, O43280, Q92519, Q96RU7, P19474, O15164, Q9UPN9, Q6AZZ1, P10155, P48995, Q13507, Q7Z4N2, Q7Z2W7, Q9HBA0, Q9BZW7, P01222, P16473, Q9H2G4, Q14166, Q8WZ42, P02766, P07437, O00294, Q15672, Q9P2K2, Q86VQ3, Q6A555, P14679, Q9BZF9, Q13404, Q14139, O95155, P11441, Q9UMX0, P17480, P09936, P15374, Q9Y3C8, P19224, P16662, P07911, Q8TCY9, Q9Y6N9, Q13107, P63027, Q15836, P18206, P55072, P21796, P08670, P04275, O75083, Q14191, P98170, Q13426, P13010, P12956, P67809, Q9Y2T7, O43829, Q13105, Q15915, O95409, Q8N9L1, Q9UDV7, Q9Y3S2, Q9UL40, Q14966, Q9H0M5, Q9Y5V0, Q96C28, Q9H5H4.

In a further preference, the peptide used for the inventive compound (e.g. peptide P or $P_a$ or $P_b$) comprises an epitope or epitope part (e.g. at least two, preferably at least three, more preferably at least four, even more preferably at least five, yet even more preferably at least six, especially at least seven or even at least eight amino acids) of one of the following histocompatibility antigens identified by their UniProt accession code:

P04233, O15523, O14602, Q30201, P01891, P01892, P04439, P05534, P10314, P10316, P13746, P16188, P16189, P16190, P18462, P30443, P30447, P30450, P30453, P30455, P30456, P30457, P30459, P30512, Q09160, P01889, P03989, P10319, P18463, P18464, P18465, P30460, P30461, P30462, P30464, P30466, P30475, P30479, P30480, P30481, P30483, P30484, P30485, P30486, P30487, P30488, P30490, P30491, P30492, P30493, P30495, P30498, P30685, Q04826, Q29718, Q29836, Q29940, Q31610, Q31612, Q95365, P04222, P10321, P30499, P30501, P30504, P30505, P30508, P30510, Q07000, Q29865, Q29960, Q29963, Q95604, Q9TNN7, P28067, P28068, P06340, P13765, P20036, P04440, P01909, P01906, P01920, P05538, P01903, P01911, P01912, P04229, P13760, P13761, P20039, Q29974, Q30134, Q30167, Q5Y7A7, Q95IE3, Q9GIY3, Q9TQE0, P79483, P13762, Q30154, P13747, P30511, P17693, Q9BY66, Q29983, Q29980, P22090, Q03519, O14607, P08048.

In another preference, the peptide used for the inventive compound (e.g. peptide P or $P_a$ or $P_b$) comprises an epitope or epitope part (e.g. at least two, preferably at least three, more preferably at least four, even more preferably at least five, yet even more preferably at least six, especially at least seven or even at least eight amino acids) of an AAV-antigen (such as an AAV capsid protein, see e.g. Example 10), in particular wherein the AAV is one of AAV-8, AAV-9, AAV-6, AAV-2 or AAV-5, or of one of the following antigens of gene delivery vectors identified by their UniProt accession code:

A9RAI0, B5SUY7, O41855, O56137, O56139, P03135, P04133, P04882, P08362, P10269, P12538, P69353, Q5Y9B2, Q5Y9B4, Q65311, Q6JC40, Q6VGT5, Q8JQF8, Q8JQG0, Q98654, Q9WBP8, Q9YIJ1; preferably wherein the peptide comprises the AAV-8 capsid protein sequence LQQQNT (SEQ ID NO: 18), TTTGQNNNS (SEQ ID NO: 19) or GTANTQ (SEQ ID NO: 20).

In yet another preference, the peptide used for the inventive compound (e.g. peptide P or $P_a$ or $P_b$) comprises an epitope or epitope part (e.g. at least two, preferably at least three, more preferably at least four, even more preferably at least five, yet even more preferably at least six, especially at least seven or even at least eight amino acids) of an AAV-antigen (such as an AAV capsid protein, see e.g. Example 10), in particular wherein the AAV is one of AAV-8, AAV-9, AAV-6, AAV-2 or AAV-5, or of one of the following antigens of gene delivery vectors identified by their UniProt accession code:

A9RAI0, B5SUY7, O41855, O56137, O56139, P03135, P04133, P04882, P08362, P10269, P12538, P69353, Q5Y9B2, Q5Y9B4, Q65311, Q6JC40, Q6VGT5, Q8JQF8, Q8JQG0, Q98654, Q9WBP8, Q9YIJ1; preferably wherein the peptide comprises the AAV-8 capsid protein sequence LQQQNT (SEQ ID NO: 18), TTTGQNNNS (SEQ ID NO: 19) or GTANTQ (SEQ ID NO: 20).

In even yet another preference, the peptide used for the inventive compound (e.g. peptide P or $P_a$ or $P_b$) comprises an epitope or epitope part (e.g. at least two, preferably at least three, more preferably at least four, even more preferably at least five, yet even more preferably at least six, especially at least seven or even at least eight amino acids) of one of the following antigens of drugs/active agents identified in Table 2:

| Drug/Active agent | Sequence available in | Is an international non-proprietary name (INN)? | Exemplary prescription product |
|---|---|---|---|
| Abciximab | DrugBank | YES | |
| Adalimumab | DrugBank | YES | |
| Aflibercept | DrugBank | YES | |
| Agalsidase beta | DrugBank | YES | |
| Albiglutide | DrugBank | YES | |
| Albutrepenonacog alfa | DrugBank | YES | |
| Aldesleukin | DrugBank | YES | |
| Alglucosidase alfa | DrugBank | YES | |
| Anakinra | DrugBank | YES | |
| Asfotase Alfa | DrugBank | YES | |
| Atacicept | DrugBank | YES | |
| Atezolizumab | DrugBank | YES | |
| Becaplermin | DrugBank | YES | |
| Belatacept | DrugBank | YES | |
| Bevacizumab | DrugBank | YES | |
| Cerliponase alfa | DrugBank | YES | |
| Cetuximab | DrugBank | YES | |
| Choriogonadotropin alfa | DrugBank | YES | |
| Denileukin diftitox | DrugBank | YES | |
| Dulaglutide | DrugBank | YES | |
| Elapegademase | DrugBank | YES | |
| Elosulfase alfa | DrugBank | YES | |
| Emicizumab | DrugBank | YES | |
| Eptacog alfa | DrugBank | YES | |
| Erenumab | DrugBank | YES | |
| Etanercept | DrugBank | YES | |
| Filgrastim | DrugBank | YES | |
| Galsulfase | DrugBank | YES | |
| Ibritumomab tiuxetan | DrugBank | YES | |
| Idarucizumab | DrugBank | YES | |
| Idursulfase | DrugBank | YES | |
| interferon alfa-2b | DrugBank | YES | |
| interferon alfacon-1 | DrugBank | YES | |
| Ipilimumab | DrugBank | YES | |
| Ixekizumab | DrugBank | YES | |
| Laronidase | DrugBank | YES | |
| Lutropin alfa | DrugBank | YES | |
| Mecasermin | DrugBank | YES | |
| Metreleptin | DrugBank | YES | |
| Ofatumumab | DrugBank | YES | |
| Omalizumab | DrugBank | YES | |
| Oportuzumab monatox | DrugBank | YES | |
| Oprelvekin | DrugBank | YES | |
| Palifermin | DrugBank | YES | |
| Pegademase | DrugBank | YES | |
| Pegloticase | DrugBank | YES | |
| Rasburicase | DrugBank | YES | |
| Rilonacept | DrugBank | YES | |
| Rituximab | DrugBank | YES | |
| Romiplostim | DrugBank | YES | |
| Sebelipase alfa | DrugBank | YES | |
| Tagraxofusp | DrugBank | YES | |
| Tasonermin | DrugBank | YES | |
| Thyrotropin alfa | DrugBank | YES | |
| Trastuzumab | DrugBank | YES | |
| Turoctocog alfa | DrugBank | YES | |
| Alpha-1-proteinase inhibitor | DrugBank | | Aralast NP |
| Antihemophilic factor human | DrugBank | | Hemofil M |
| Drotrecogin alfa | DrugBank | | Xigris |
| Erythropoietin | DrugBank | | Abseamed |
| Follitropin | DrugBank | | Bemfola |
| Interferon alpha-1 | DrugBank | | MultiferonT |
| Interferon alpha-10 | DrugBank | | MultiferonT |
| Interferon alpha-14 | DrugBank | | MultiferonT |
| Interferon alpha-2 | DrugBank | | MultiferonT |
| Interferon alpha-21 | DrugBank | | MultiferonT |
| Interferon alpha-8 | DrugBank | | MultiferonT |
| Interferon beta-1a | DrugBank | | Avonex |
| interferon gamma-1b | DrugBank | | Actimmune |
| Somatotropin | DrugBank | | Gentropin |
| Corifollitropin alfa | KEGG | YES | |
| Efmoroctocog alfa | KEGG | YES | |
| Eftrenonacog alfa | KEGG | YES | |
| Evolocumab | KEGG | YES | |
| Natalizumab | KEGG | YES | |
| Taliglucerase alfa | KEGG | YES | |
| Teprotumumab | KEGG | YES | |
| Velmanase alpha | UniProt O00754 | YES | |
| Factor XIII (alpha and beta chain) | UniProt P00488 & P05160 | | Corifact |
| *E. coli* Asparaginase | UniProt P00805 | | Elspar |
| Antithrombin III | UniProt P01008 | YES | |
| Beta-nerve growth factor (NGF) | UniProt P01138 | | |
| Parathyroid hormone | UniProt P01270 | YES | |
| insulin | UniProt P01308 | YES | |
| Alglucerase | UniProt P04062 | YES | |
| Von Willebrand Factor Human | UniProt P04275 | | Humate-P |
| Plasma protease C1 inhibitor | UniProt P05155 | | Berinert |
| Fibroblast growth factor 2 (FGF2) | UniProt P09038 | | |
| Granulocyte colony-stimulating factor (G-CSF) | UniProt P09919 | | |
| Sphingomyelin phosphodiesterase | UniProt P17405 | | |
| Brain-derived neurotrophic factor (BDNF) | UniProt P23560 | | |
| Glial cell line-derived neurotrophic factor (GDNF) | UniProt P39905 | | |

DrugBank (https://www.drugbank.ca/);
KEGG: Kyoto Encyclopedia of Genes and Genomes (https://www.genome.jp/kegg/) .

The respective DrugBank and KEGG database accession numbers are listed below in Table 3 (DrugBank and KEGG database versions as of 20 Mar. 2019):

| ENZYMES | |
|---|---|
| DB00058 | Alpha-1-proteinase inhibitor |
| DB00088 | Ceredase/Alglucerase |
| DB00053 | Imiglucerase/Cerezyme |
| D09675 (KEGG) | Taliglucerase alfa |
| DB00061 | Pegademase Deaminase bovine |
| DB00103 | Agalsidase beta Fabry |
| DB01272 | Alglucosidase alfa Pompe |
| DB00090 | Laronidase a-L-Iduronidase Hurler, MPS I |
| DB01271 | Idursulfase Iduronate-2-Sulfatase M Hunter, MPS II |
| DB09051 | Elosulfase alfa N-Acetylgalactosamine-6 Sulfatase Morquio Snydr A, MPS IVA |
| DB01279 | Galsulfase N-Acetylgalactosamine-4 Sulfatase Maroteaux-Lamy, MPS VI |
| DB11563 | Sebelipase alfa Lysosomal Acid Lipase Wolman, LAL Deficiency |
| DB13173 | Cerliponase alfa Batten disease |
| DB11563 | Sebelipase alfa Lysosomal acid lipase deficiency (LAL-D) |
| DB09105 | Asfotase Alfa Perinatal/infantile- and juvenile-onset hypophosphatasia (HPP) |
| DB14712 | Elapegademase Severe combined immunodeficiency disease (SCID) |
| D10820 (KEGG) | Olipudase alpha Niemann Pick |
| D11024 | Velmanase alpha (alpha-Mannosidosis) |
| DB00049 | Rasburicase (Elitec) urate-oxidase |
| DB09208 | Pegloticase (procine-like uricase) |
| COAGULATION FACTORS | |
| DB09109 | Turoctocog alfa (modified FVIII) |
| DB00055 | Drotrecogin alfa activated human protein C |
| DB13923 | Emicizumab mimics FVIII |
| DB00036 | Coagulation factor VIIa |
| DB00025 | Antihemophilic factor |
| DB13133 | Von Willebrand Factor Human (Vovendi) |
| D10831 (KEGG) | Susoctocog alfa |
| DB00025 | hu rec FVIII |
| DB13152 | Coagulation Factor IX Human |
| CYTOKINES: | |
| DB00038 | Oprelvekin (rec IL11) |
| DB00041 | Aldesleukin (IL2) |
| DB06372 | Rilonacept (IL1-inhibitor) |
| DB00026 | Anakinra (IL1Ra) |
| DB00004 | Denileukin diftitox |
| DB00060 | Interferon beta 1a |
| DB05258 | Interferon alpha |
| DB00105 | Interferon alpha 2b |
| DB00069 | Interferon alphacon 1 |
| DB00033 | Interferon gamma-1b |
| DB00034 | Interferon Alfa-2a, Recombinant |
| >HORMONES: | |
| DB00024 | Thyrotropin alfa |
| DB00097 | Choriogonadotropin alfa |
| DB00066 | Follitropin |
| DB00044 | Lutropin alfa |
| DB00052 | Somatotropin |
| DB09043 | Albiglutide glucagon-like peptide-1 agonist (GLP-1) |
| DB09046 | Metreleptin (Leptin homologue) |
| D08895 (KEGG) | Corifollitropin alfa |
| GROWTH FACTORS: | |
| DB00099 | Filgrastim (G-CSF) |
| DB01277 | Mecasermin |
| DB00039 | Palifermin |
| DB00102 | Becaplermin (PDGF) |
| DB00039 | Palifermin (KGF) |
| DB11626 | Tasonermin (TGF alpha) |
| FUSION PROTEINS: | |
| DB08885 | Aflibercept (VEGF-R/ Fc fusion) |
| DB06372 | Rilonacept (IL-1R/Fc fusion) |
| DB05332 | Romiplostim (dimer Fc-pep fusion [peptibody], binding thrombopoietin rec) |
| DB14731 | Tag raxofusp (IL-3 conjugated truncated diphtheria toxin) |
| DB01281 | Abatacept (Fc hinge fusion to CTLA-4) |
| D10830 (KEGG) | Efmoroctocog alfa (FVIII-Fc fusion) |
| D10522 (KEGG) | Eftrenonacog alfa (human factor IX (FIX)-Fc fusion) |
| DB06372 | Rilonacept (IL-1R & IL-1R access prot Fc fusion) |
| DB14731 | Tag raxofusp (IL-3 conjugated truncated diphtheria toxin) |
| DB06681 | Belatacept (CTLA-4/Fc fusion) |
| DB06399 | Atacicept (extracellular ligand binding portion of TACI) |
| DB09043 | GLP-1 receptor agonist-albumin fusion |
| DB13884 | Albutrepenonacog alfa Recombinant factor IX albumin fusion (Idelvion) |
| DB08885 | Aflibercept VEGFR Fc-fusion (Zaltrap) |
| DB09045 | Dulaglutide Glucagon like pep 1 receptor agonist Fc-fusion (Trulicity) |
| DB06681 | Belatacept CTLA-4 Fc-fusion (Nulojix) |
| DB08885 | Aflibercept VEGFR Fc-fusion (Eylea) |
| DB00005 | Etanercept Fc fusion FR Fc-fusion |
| D10830 (KEGG) | Efmoroctocog alfa Rec F VIII Fc-fusion Elocta |
| D10522 (KEGG) | Eftrenonacog alfa Rec F IX Fc fusion (Alprolix) |
| DB09105 | Asfotase Alfa Fc fusion/enzyme asfotase-alfa [Strensiq] |
| THERAPEUTIC mABs: | |
| D06886 (KEGG) | Natalizumab |
| DB00073 | Rituximab |
| DB00051 | Adalimumab/Humira |
| DB06186 | Ipilimumab |
| DB00072 | Herceptin/Trastuzumab |
| DB00112 | Avastin/Bevacizumab |
| DB00005 | Etanercept (Enbrel) |
| D10557 (KEGG) | Evolocumab |
| DB11569 | Ixekizumab (huIgG4 anti interleukin-17A) |
| DB00043 | Omalizumab |
| D09680 (KEGG) | Teprotumumab |
| ANTIBODY-FRAGMENTS & DERIVATIVES: | |
| DB09264 | Idarucizumab (Fab) |
| DB00002 | Cetuximab (epidermal growth factor receptor binding FAB) |
| DB05319 | Oportuzumab monatox scFv-Toxin fusion |
| DB00078 | Ibritumomab (murine IgG1 kappa) tiuxetan |
| DB00054 | Abciximab (chimaeric human/mouse mAB) |
| DB00073 | Rituximab (hu IgG1 kappa) |
| DB06650 | Ofatumumab (hu IgG) |
| DB14039 | Erenumab (antag. calcitonin gene-rel pep. rec [CGRPR] migraine) |
| DB13923 | Emicizumab (mimics the function of the coagulation Factor VIII) |
| DB11595 | Atezolizumab (Fc-engineered, hum. mAB recognizing PD-L1) |
| DB09264 | Idarucizumab - Fab (inactivates anticoagulant dabigatran) |

Drugs/active agents on which the present invention can be applied (i.e. drugs/active agents leading to undesirable antibodies which can be depleted by the compound of present invention) are also disclosed e.g. in Spiess et al 2015 and Runcie et al 2018. They may also be a scFv, Fab2, Fab3, Bis-scFv, bivalent minibody, diabody, triabody or tetrabody. Further, such drugs/active agents may be an affibody molecule (Protein Data Bank: 1LP1), affimer (Protein Data Bank: 1NB5), affitin molecule (Protein Data Bank: 4CJ2), anticalin molecule (Protein Data Bank: 4GH7), atrimer molecule (Protein Data Bank: 1TN3), fynomer (Protein Data Bank: 1M27), armadillo repeat protein (Protein Data Bank: 4DB9), Kunitz domain inhibitor (Protein Data Bank: 1ZR0), knottin molecule (Protein Data Bank: 2IT7), designed ankyrin repeat protein (Protein Data Bank: 2Q4J); Protein Databank (PDB) version as of 20 Mar. 2019. Further suitable drugs/active agents are disclosed e.g. in WO 2017/

220569 A1, WO 2017/087589 A2, U.S. Pat. No. 82,100,547 and EP 1697421 A2 (in particular SEQ ID NO: 1 thereof). As above, the peptide used for the inventive compound (e.g. peptide P or $P_a$ or $P_b$) may comprise an epitope or epitope part (e.g. at least two, preferably at least three, more preferably at least four, even more preferably at least five, yet even more preferably at least six, especially at least seven or even at least eight amino acids) of the amino acid sequences of any one of the drugs/active agents disclosed in the aforementioned sources.

It is also highly preferred that the peptides used for the inventive compound do not bind to any HLA Class I or HLA Class II molecule (i.e. of the individual to be treated, e.g. human), in order to prevent presentation and stimulation via a T-cell receptor in vivo and thereby induce an immune reaction. It is generally not desired to involve any suppressive (or stimulatory) T-cell reaction in contrast to antigen-specific immunologic tolerization approaches. Therefore, to avoid T-cell epitope activity as much as possible, the peptides of the compound of the present invention (e.g. peptide P or $P_a$ or $P_b$ or $P_1$ or $P_2$) preferably fulfil one or more of the following characteristics:

- To reduce the probability for a peptide used in the compound of the present invention to bind to an HLA Class II or Class I molecule, the peptide (e.g. peptide P or $P_a$ or $P_b$ or $P_1$ or $P_2$) has a preferred length of 4-8 amino acids, although somewhat shorter or longer lengths are still acceptable.
- To further reduce the probability that such a peptide binds to an HLA Class II or Class I molecule, it is preferred to test the candidate peptide sequence by HLA binding prediction algorithms such as NetMHCII-2.3 (reviewed by Jensen et al 2018). Preferably, a peptide (e.g. peptide P or $P_a$ or $P_b$ or $P_1$ or $P_2$) used in the compound of the present invention has (predicted) HLA binding (IC50) of at least 500 nM. More preferably, HLA binding (IC50) is more than 1000 nM, especially more than 2000 nM (cf. e.g. Peters et al 2006). In order to decrease the likelihood of HLA Class I binding, NetMHCpan 4.0 may also be applied for prediction (Jurtz et al 2017).
- To further reduce the probability that such a peptide binds to an HLA Class I molecule, the NetMHCpan Rank percentile threshhold can be set to a background level of 10% according to Koşaloğlu-Yalçin et al 2018 (PMID: 30377561). Preferably, a peptide (e.g. peptide P or $P_a$ or $P_b$ or $P_1$ or $P_2$) used in the compound of the present invention therefore has a % Rank value of more than 3, preferably more than 5, more preferably more than 10 according to the NetMHCpan algorithm.
- To further reduce the probability that such a peptide binds to an HLA Class II molecule, it is beneficial to perform in vitro HLA-binding assays commonly used in the art such as for example refolding assays, iTopia, peptide rescuing assays or array-based peptide binding assays. Alternatively, or in addition thereto, LC-MS based analytics can be used, as e.g. reviewed by Gfeller et al 2016.

For stronger reduction of the titre of the undesired antibodies, it is preferred that the peptides used in the present invention are circularized (see also Example 4). Accordingly, in a preferred embodiment, at least one occurrence of P is a circularized peptide. Preferably at least 10% of all occurrences of P are circularized peptides, more preferably at least 25% of all occurrences of P are circularized peptides, yet more preferably at least 50% of all occurrences of P are circularized peptides, even more preferably at least 75% of all occurrences of P are circularized peptides, yet even more preferably at least 90% of all occurrences of P are circularized peptides or even at least 95% of all occurrences of P are circularized peptides, especially all of the occurrences of P are circularized peptides. Several common techniques are available for circularization of peptides, see e.g. Ong et al 2017. It goes without saying that "circularized peptide" as used herein shall be understood as the peptide itself being circularized, as e.g. disclosed in Ong et al. (and not e.g. grafted on a circular scaffold with a sequence length that is longer than 13 amino acids). Such peptides may also be referred to as cyclopeptides herein.

Further, for stronger reduction of the titre of the undesired antibodies relative to the amount of scaffold used, in a preferred embodiment of the compound of the present invention, independently for each of the peptide n-mers, n is at least 2, more preferably at least 3, especially at least 4. Usually, in order to avoid complexities in the manufacturing process, independently for each of the peptide n-mers, n is less than 10, preferably less than 9, more preferably less than 8, even more preferably less than 7, yet even more preferably less than 6, especially less than 5. To benefit from higher avidity through divalent binding of the undesired antibody, it is highly preferred that, for each of the peptide n-mers, n is 2.

For multivalent binding of the undesired antibodies, it is advantageous that the peptide dimers or n-mers are spaced by a hydrophilic, structurally flexible, immunologically inert, non-toxic and clinically approved spacer such as (hetero-)bifunctional and -trifunctional Polyethylene glycol (PEG) spacers (e.g. NHS-PEG-Maleimide)—a wide range of PEG chains is available and PEG is approved by the FDA. Alternatives to PEG linkers such as immunologically inert and non-toxic synthetic polymers or glycans are also suitable. Accordingly, in the context of the present invention, the spacer (e.g. spacer S) is preferably selected from PEG molecules or glycans. For instance, the spacer such as PEG can be introduced during peptide synthesis. Such spacers (e.g. PEG spacers) may have a molecular weight of e.g. 10000 Dalton. Evidently, within the context of the present invention, the covalent binding of the peptide n-mers to the biopolymer scaffold via a linker each may for example also be achieved by binding of the linker directly to a spacer of the peptide n-mer (instead of, e.g., to a peptide of the peptide n-mer).

Preferably, each of the peptide n-mers is covalently bound to the biopolymer scaffold, preferably via a linker each.

As used herein, the linker may e.g. be selected from disulphide bridges and PEG molecules.

According to a further preferred embodiment of the inventive compound, independently for each occurrence, P is $P_a$ or $P_b$.

Furthermore, it is preferred when in the first peptide n-mer, each occurrence of P is $P_a$ and, in the second peptide n-mer, each occurrence of P is $P_b$. Alternatively, or in addition thereto, $P_a$ and/or $P_b$ is circularized.

Divalent binding is particularly suitable to reduce antibody titres. According, in a preferred embodiment,

- the first peptide n-mer is $P_a$—S—$P_a$ and the second peptide n-mer is $P_a$—S—$P_a$;
- the first peptide n-mer is $P_a$—S—$P_a$ and the second peptide n-mer is $P_b$—S—$P_b$;
- the first peptide n-mer is $P_b$—S—$P_b$ and the second peptide n-mer is $P_b$—S—$P_b$;
- the first peptide n-mer is $P_a$—S—$P_b$ and the second peptide n-mer is $P_a$—S—$P_b$;

the first peptide n-mer is $P_a$—S—$P_b$ and the second peptide n-mer is $P_a$—S—$P_a$; or the first peptide n-mer is $P_a$—S—$P_b$ and the second peptide n-mer is $P_b$—S—$P_b$.

For increasing effectivity, in particular in autoimmune disease (which is usually based on polyclonal antibodies, see above), in a preferred embodiment the first peptide n-mer is different from the second peptide n-mer. For similar reasons, preferably, the peptide $P_a$ is different from the peptide $P_b$, preferably wherein the peptide $P_a$ and the peptide $P_b$ are two different epitopes of the same antigen or two different epitope parts of the same epitope.

Especially for better targeting of polyclonal antibodies, it is advantageous when the peptide $P_a$ and the peptide $P_b$ comprise the same amino-acid sequence fragment, wherein the amino-acid sequence fragment has a length of at least 2 amino acids, preferably at least 3 amino acids, more preferably at least 4 amino acids, yet more preferably at least 5 amino acids, even more preferably at least 6 amino acids, yet even more preferably at least 7 amino acids, especially at least 8 amino acids or even at least 9 amino acids.

Further, for stronger reduction of the titre of the undesired antibodies relative to the amount of scaffold used, the compound comprises a plurality of said first peptide n-mer (e.g. up to 10 or 20 or 30) and/or a plurality of said second peptide n-mer (e.g. up to 10 or 20 or 30).

For stronger reduction of the titre of the undesired antibodies relative to the amount of scaffold used, the compound may also comprise at least a third peptide n-mer of the general formula:

$P(—S—P)_{(n-1)}$, wherein, independently for each occurrence, P is a peptide with a sequence length of 2-13 amino acids, preferably 3-11 amino acids, more preferably 4-9 amino acids, especially 5-8 amino acids, and S is a non-peptide spacer, preferably wherein each occurrence of P is $P_c$, wherein $P_c$ is a peptide with a sequence length of 2-13 amino acids, preferably 3-11 amino acids, more preferably 4-9 amino acids, especially 5-8 amino acids, more preferably wherein $P_c$ is circularized;

a fourth peptide n-mer of the general formula:

$P(—S—P)_{(n-1)}$, wherein, independently for each occurrence, P is a peptide with a sequence length of 2-13 amino acids, preferably 3-11 amino acids, more preferably 4-9 amino acids, especially 5-8 amino acids, and S is a non-peptide spacer, preferably wherein each occurrence of P is $P_d$, wherein $P_d$ is a peptide with a sequence length of 2-13 amino acids, preferably 3-11 amino acids, more preferably 4-9 amino acids, especially 5-8 amino acids, more preferably wherein $P_d$ is circularized;

a fifth peptide n-mer of the general formula:

$P(—S—P)_{(n-1)}$, wherein, independently for each occurrence, P is a peptide with a sequence length of 2-13 amino acids, preferably 3-11 amino acids, more preferably 4-9 amino acids, especially 5-8 amino acids, and S is a non-peptide spacer, preferably wherein each occurrence of P is $P_e$, wherein $P_e$ is a peptide with a sequence length of 2-13 amino acids, preferably 3-11 amino acids, more preferably 4-9 amino acids, especially 5-8 amino acids, more preferably wherein $P_e$ is circularized;

a sixth peptide n-mer of the general formula:

$P(—S—P)_{(n-1)}$, wherein, independently for each occurrence, P is a peptide with a sequence length of 2-13 amino acids, preferably 3-11 amino acids, more preferably 4-9 amino acids, especially 5-8 amino acids, and S is a non-peptide spacer, preferably wherein each occurrence of P is $P_f$, wherein $P_f$ is a peptide with a sequence length of 2-13 amino acids, preferably 3-11 amino acids, more preferably 4-9 amino acids, especially 5-8 amino acids, more preferably wherein $P_f$ is circularized;

a seventh peptide n-mer of the general formula:

$P(—S—P)_{(n-1)}$, wherein, independently for each occurrence, P is a peptide with a sequence length of 2-13 amino acids, preferably 3-11 amino acids, more preferably 4-9 amino acids, especially 5-8 amino acids, and S is a non-peptide spacer, preferably wherein each occurrence of P is $P_g$, wherein $P_g$ is a peptide with a sequence length of 2-13 amino acids, preferably 3-11 amino acids, more preferably 4-9 amino acids, especially 5-8 amino acids, more preferably wherein $P_g$ is circularized;

a eighth peptide n-mer of the general formula:

$P(—S—P)_{(n-1)}$, wherein, independently for each occurrence, P is a peptide with a sequence length of 2-13 amino acids, preferably 3-11 amino acids, more preferably 4-9 amino acids, especially 5-8 amino acids, and S is a non-peptide spacer, preferably wherein each occurrence of P is $P_h$, wherein $P_h$ is a peptide with a sequence length of 2-13 amino acids, preferably 3-11 amino acids, more preferably 4-9 amino acids, especially 5-8 amino acids, more preferably wherein $P_h$ is circularized;

a ninth peptide n-mer of the general formula:

$P(—S—P)_{(n-1)}$, wherein, independently for each occurrence, P is a peptide with a sequence length of 2-13 amino acids, preferably 3-11 amino acids, more preferably 4-9 amino acids, especially 5-8 amino acids, and S is a non-peptide spacer, preferably wherein each occurrence of P is $P_i$, wherein $P_i$ is a peptide with a sequence length of 2-13 amino acids, preferably 3-11 amino acids, more preferably 4-9 amino acids, especially 5-8 amino acids, more preferably wherein $P_i$ is circularized;

a tenth peptide n-mer of the general formula:

$P(—S—P)_{(n-1)}$, wherein, independently for each occurrence, P is a peptide with a sequence length of 2-13 amino acids, preferably 3-11 amino acids, more preferably 4-9 amino acids, especially 5-8 amino acids, and S is a non-peptide spacer, preferably wherein each occurrence of P is $P_j$, wherein $P_j$ is a peptide with a sequence length of 2-13 amino acids, preferably 3-11 amino acids, more preferably 4-9 amino acids, especially 5-8 amino acids, more preferably wherein $P_j$ is circularized.

Peptides $P_c$-$P_j$ may have one or more of same features (e.g. sequence) as disclosed herein for peptides $P_a$ and $P_b$.

As also illustrated above, it is highly preferred when the compound of the present invention is non-immunogenic in a mammal, preferably in a human, in a non-human primate, in a sheep, in a pig, in a dog or in a rodent.

In the context of the present invention, a non-immunogenic compound preferably is a compound wherein the biopolymer scaffold (if it is a protein) and/or the peptides (of the peptide n-mers) have an IC50 higher than 100 nM, preferably higher than 500 nM, even more preferably higher than 1000 nM, especially higher than 2000 nM, against HLA-DRB1_0101 as predicted by the NetMHCII-2.3 algorithm. The NetMHCII-2.3 algorithm is described in detail in Jensen et al, which is incorporated herein by reference. The algorithm is publicly available under http://www.cbs.dtu.dk/services/NetMHCII-2.3/. Even more preferably, a non-immunogenic compound (or pharmaceutical composition) does not bind to any HLA and/or MHC molecule (e.g. in a mammal, preferably in a human, in a non-human primate, in a sheep, in a pig, in a dog or in a rodent; or of the individual to be treated) in vivo.

According to a further preference, the compound is for intracorporeal sequestration (or intracorporeal depletion) of at least one antibody in an individual, preferably in the bloodstream of the individual and/or for reduction of the titre of at least one antibody in the individual, preferably in the bloodstream of the individual.

In another preferred embodiment, the entire sequence, optionally with the exception of an N-terminal and/or C-terminal cysteine, of at least one occurrence of P, preferably of at least 10% of all occurrences of P, more preferably of at least 25% of all occurrences of P, yet more preferably of at least 50% of all occurrences of P, even more preferably of at least 75% of all occurrences of P, yet even more preferably of at least 90% of all occurrences of P or even of at least 95% of all occurrences of P, especially of all of the occurrences of P, is identical to a sequence fragment of a protein, wherein the protein is identified by one of the UniProt accession codes disclosed herein; optionally wherein the sequence fragment comprises at most five, preferably at most four, more preferably at most three, even more preferably at most two, especially at most one amino acid substitutions (e.g. for the purposes mentioned above, such as creating mimotopes).

In another preferred embodiment, the entire sequence, optionally with the exception of an N-terminal and/or C-terminal cysteine, of peptide $P_a$ is identical to a sequence fragment of a protein, wherein the protein is identified by one of the UniProt accession codes disclosed herein; optionally wherein said sequence fragment comprises at most five, preferably at most four, more preferably at most three, even more preferably at most two, especially at most one amino acid substitutions (e.g. for the purposes mentioned above, such as creating mimotopes).

In another preferred embodiment, the entire sequence, optionally with the exception of an N-terminal and/or C-terminal cysteine, of peptide $P_b$ is identical to a sequence fragment of a protein, wherein the protein is identified by one of the UniProt accession codes disclosed herein; optionally wherein said sequence fragment comprises at most five, preferably at most four, more preferably at most three, even more preferably at most two, especially at most one amino acid substitutions (e.g. for the purposes mentioned above, such as creating mimotopes).

In another preferred embodiment, the entire sequence, optionally with the exception of an N-terminal and/or C-terminal cysteine, of peptide $P_a$ is identical to a sequence fragment of a protein and the entire sequence, optionally with the exception of an N-terminal and/or C-terminal cysteine, of peptide $P_b$ is identical to the same or another, preferably another, sequence fragment of the same protein, wherein the protein is identified by one of the UniProt accession codes listed herein; optionally wherein said sequence fragment and/or said another sequence fragment comprises at most five, preferably at most four, more preferably at most three, even more preferably at most two, especially at most one amino acid substitutions (e.g. for the purposes mentioned above, such as creating mimotopes).

Myasthenia gravis is an autoimmune neuromuscular disorder mediated by autoantibodies that cause a broad spectrum of several clinical symptoms from mild muscle weakness to a life-threatening myasthenic crisis with breathing problems. Around 80% of myasthenic patients develop anti nicotinic acetylcholine receptor (AChR) antibodies that lead to complement-mediated damaging of the postsynaptic membrane (Howard 2018), direct AChR blocking or receptor endocytosis. These disease-causing autoantibodies are mainly directed to defined immunogenic regions AChR or MuSK (Ruff 2018). They represent a good example for functionally well characterized, disease-causing autoantibodies. Although general immunosuppressive or B-cell targeting strategies exist, a strategy is needed whereby only diseases-causing antibodies (rather than all, mostly protective antibodies) are rapidly inactivated or depleted (especially in a myasthenic crisis), since neither of the generally immunosuppressive treatments with corticoids, IVIG, thymectomy or by plasma exchange are satisfactory. So far, no convenient therapeutic intervention exists that can deplete or neutralize disease causing antibodies in myasthenia gravis rapidly and selectively.

Rey et al. concerns the characterization of human antiacetylcholine receptor monoclonal autoantibodies from the peripheral blood of a myasthenia gravis patient using combinatorial libraries.

EP 2698386 A1 relates to a fusion protein which is asserted to specifically suppress autoantibodies such as autoantibodies involved in myasthenia gravis. The fusion protein contains a binding site for the autoantibody and a fragment of the antibody heavy chain constant region which exhibits antibody-dependent cellular cytotoxicity.

Non-selective B-cell targeting or immunotherapeutic approaches are not yet an established therapeutic option for the treatment of myasthenia gravis. Alternatively, few intra- and extracorporeal selective antibody depletion or B-cell suppression strategies targeting disease-causing antibodies in myasthenia gravis were proposed using indirect or direct targeting approaches against disease causing antibodies (see e.g. Homma 2017 and Lazaridis 2017). In addition, an AChR-specific immunosuppressive therapy using an adjuvanted AChR vaccine was proposed (Luo 2015). However, there remains an urgent need for a comparatively effective and safe and rapidly acting selective antibody depletion therapy.

Accordingly, as mentioned in the summary, the present invention also relates to a compound (for use in the prevention or treatment of myasthenia gravis, especially in a myasthenic crisis), preferably for the sequestration (or depletion) of anti human muscle nicotinic acetylcholine receptor (AChR) antibodies, anti human muscle-specific receptor tyrosine kinase antibodies and/or anti human low-density lipoprotein receptor related protein 4 antibodies present in a human individual, the compound comprising a biopolymer scaffold and at least two peptides with a sequence length of 7-13 amino acids, wherein each of the peptides independently comprises a 7-13 amino-acid sequence fragment of the AChR subunit alpha sequence identified by UniProt accession code P02708 (optionally wherein the sequence fragment comprises at most five, preferably at most four, more preferably at most three, even more preferably at most two, especially at most one amino acid substitutions (e.g. such that a mimotope is formed)) or of the muscle-specific receptor tyrosine kinase sequence identified by UniProt accession code 015146 or of the low-density lipoprotein receptor related protein 4 sequence identified by UniProt accession code 075096 (optionally wherein the sequence fragment comprises at most five, preferably at most four, more preferably at most three, even more preferably at most two, especially at most one amino acid substitutions (e.g. such that a mimotope is formed)), wherein the peptides are covalently bound to the biopolymer scaffold, preferably via a linker, wherein the biopolymer scaffold is selected from the group consisting of human globulins and human albumin.

According to a particular preference, in particular for stronger reduction of the titre of the undesired antibodies relative to the amount of scaffold used, the at least two peptides comprise a peptide $P_1$ and a peptide $P_2$, wherein $P_1$ and $P_2$ comprise the same 7-13 amino-acid sequence fragment of AChR subunit alpha (optionally wherein the sequence fragment comprises at most five, preferably at most four, more preferably at most three, even more preferably at most two, especially at most one amino acid substitutions (e.g. such that a mimotope is formed)) or of the muscle-specific receptor tyrosine kinase or of low-density lipoprotein receptor related protein 4 (optionally wherein the sequence fragment comprises at most five, preferably at most four, more preferably at most three, even more preferably at most two, especially at most one amino acid substitutions (e.g. such that a mimotope is formed)), wherein $P_1$ and $P_2$ are present in form of a peptide dimer $P_1$—S—$P_2$, wherein S is a non-peptide spacer, wherein the peptide dimer is covalently bound to the biopolymer scaffold, preferably via a linker.

Preferably, said 7-13 amino-acid sequence fragment of AChR subunit alpha is a fragment of the sequence consisting of amino acids 21-255 of the AChR subunit alpha sequence identified by UniProt accession code P02708 (optionally wherein the sequence fragment comprises at most five, preferably at most four, more preferably at most three, even more preferably at most two, especially at most one amino acid substitutions (e.g. such that a mimotope is formed)).

In a further preferred embodiment, said 7-13 amino-acid sequence fragment of AChR subunit alpha is a fragment of the sequence LKWNPDDYGGVKKIHIPSEK (SEQ ID NO: 1), preferably of the sequence WNPDDYGGVK (SEQ ID NO: 2) or VKKIHIPSEK (SEQ ID NO: 3) (optionally wherein the sequence fragment comprises at most five, preferably at most four, more preferably at most three, even more preferably at most two, especially at most one amino acid substitutions (e.g. such that a mimotope is formed)).

In a further preferred embodiment, the peptides have a sequence length of 8-13 amino acids, preferably 9-12 amino acids, more preferably 10-12 amino acids, especially wherein the peptides consist of the sequence VKKIHIPSEKG (SEQ ID NO: 4) optionally with an N-terminal and/or C-terminal cysteine residue, and/or optionally wherein the sequence fragment comprises at most five, preferably at most four, more preferably at most three, even more preferably at most two, especially at most one amino acid substitutions (e.g. such that a mimotope is formed).

According to a further preferred embodiment, the compound further comprises at least one peptide with a sequence length of 7-13 amino acids, wherein the at least one peptide comprises a 7-13 amino-acid sequence fragment of the muscle-specific receptor tyrosine kinase sequence identified by UniProt accession code 015146 or of the low-density lipoprotein receptor related protein 4 sequence identified by UniProt accession code 075096, wherein the at least one peptide is covalently bound to the biopolymer scaffold, preferably via a linker.

Furthermore, also for use in the prevention or treatment of myasthenia gravis (especially in a myasthenic crisis), in a preferred embodiment of inventive compound, at least one occurrence of P is $P_a$ and at least one occurrence of P is $P_b$, wherein $P_a$ is a peptide with a sequence length of 5-13, preferably 7-13, amino acids, wherein $P_b$ is a peptide with a sequence length of 5-13, preferably 7-13, amino acids, wherein the entire sequence, optionally with the exception of an N-terminal and/or C-terminal cysteine, of peptide $P_a$ is identical to a sequence fragment of a protein, wherein the protein is identified by UniProt accession code P02708, O15146 or 075096, optionally wherein said sequence fragment comprises at most five, preferably at most four, more preferably at most three, even more preferably at most two, especially at most one amino acid substitutions, wherein the entire sequence, optionally with the exception of an N-terminal and/or C-terminal cysteine, of peptide $P_b$ is identical to a sequence fragment of a protein, wherein the protein is identified by UniProt accession code P02708, O15146 or 075096, optionally wherein said sequence fragment comprises at most five, preferably at most four, more preferably at most three, even more preferably at most two, especially at most one amino acid substitutions.

In embodiments, in particular for $P_a$ and/or $P_b$, said sequence fragment of the protein is a fragment of the sequence consisting of amino acids 21-255 of the AChR subunit alpha sequence identified by UniProt accession code P02708 (optionally wherein the sequence fragment comprises at most five, preferably at most four, more preferably at most three, even more preferably at most two, especially at most one amino acid substitutions (e.g. such that a mimotope is formed)). In further embodiments, in particular for Pa and/or Pb, said sequence fragment of the protein is a fragment of the sequence LKWNPDDYGGVKKIHIPSEK (SEQ ID NO: 1), preferably of the sequence WNPDDYGGVK (SEQ ID NO: 2) or VKKIHIPSEK (SEQ ID NO: 3). In particular, peptide Pa and/or peptide Pb consist of the sequence VKKIHIPSEKG (SEQ ID NO: 4) optionally with an N-terminal and/or C-terminal cysteine residue.

Further, for stronger reduction of the titre of the undesired antibodies related to myasthenia gravis, in a preferred embodiment, the first peptide n-mer is $P_a$—S—$P_b$ and the second peptide n-mer is $P_a$—S—$P_b$.

Pre-eclampsia is an exemplary disease of pregnancy that involves not only the placenta, but the entire organism. It occurs in 3-5% of all pregnancies predominantly in pregnant teens and women over 40 and it remains a leading cause of neonatal morbidity and mortality, typically later in pregnancy. An onset of hypertension in women that had no history of high blood pressure, elevated liver enzymes proteinuria, renal failure, low platelets (HELLP syndrome) and cerebral edema with seizures are hallmark of this condition. No specific cures are known, and the exact causes for preeclampsia appear to be complex. In general, therapeutic options are very limited.

Pathogenesis of preeclampsia involves abnormal placental implantation, placental hypoxia combined with the release of circulating factors, alterations of endothelial cell function and involvement of angiogenic factors and inflammatory cytokines. Moreover, the renin angiotensin aldosterone system (RAAS) plays an important role in preeclampsia which has been corroborated by the finding that autoantibodies against the angiotensin II type 1-receptor (AT1-AA) contribute to the underlying pathomechanism (Wallukat 1999).

The repertoire of preeclampsia-associated autoantibody specificities was recently extended e.g. to anti-alpha1-adrenoreceptors, prothrombin, anti-cardiolipin and more recently to GRP50 (Elliott 2016). Elliott and colleagues found an antigenic mimicry mechanism: Preeclampsia patients showed antibody titers against a peptide epitope within the Epstein-Barr virus nuclear antigen 1 (EBNA-1) that cross reacted with the placental GPR50 membrane protein that is expressed in placental tissue. Antibodies to the EBNA-1 antigen are also associated with several other autoimmune diseases such as Systemic Lupus Erythematosus, Multiple Sclerosis and myalgic encephalitis/chronic fatigue syndrome.

Accordingly, as mentioned in the summary, the present invention also relates to a compound, preferably for the sequestration (or depletion) of anti-Epstein-Barr virus nuclear antigen 1 (EBNA-1) antibodies, anti human melatonin-related receptor (GPR50) antibodies and/or anti human type-1 angiotensin II receptor (AT1AR) antibodies present in a human individual, the compound comprising a biopolymer scaffold and at least two peptides with a sequence length of 7-13 amino acids,
  wherein each of the peptides independently comprises a 7-13 amino-acid sequence fragment of the EBNA1 sequence identified by UniProt accession code Q1HVF7 or P03211 or of the GPR50 sequence identified by UniProt accession code Q13585 or of the type-1 angiotensin II receptor (AT1AR) sequence identified by UniProt accession code P30556, wherein the peptides are covalently bound to the biopolymer scaffold,
  wherein the biopolymer scaffold is selected from the group consisting of human globulins, preferably from the group consisting of human immunoglobulins and human haptoglobin, and human albumin.

The compound can selectively reduce the levels of undesired antibodies that crossreact with a viral antigen (such as EBNA-1) and an endogenous membrane receptor protein (such as GRP50).

According to a particular preference, in particular for stronger reduction of the titre of the undesired antibodies relative to the amount of scaffold used, the at least two peptides comprise a peptide $P_1$ and a peptide $P_2$, wherein $P_1$ and $P_2$ comprise the same 7-13 amino-acid sequence fragment of said EBNA1 sequence or said GPR50 sequence or said AT1AR sequence, wherein $P_1$ and $P_2$ are present in form of a peptide dimer $P_1$—S—$P_2$, wherein S is a non-peptide spacer, wherein the peptide dimer is covalently bound to the biopolymer scaffold, preferably via a linker.

Preferably, said 7-13 amino-acid sequence fragment is a fragment of the sequence RPQKRPSCIGCKGTH (SEQ ID NO: 5) or RPQKRPSCIGCKGAH (SEQ ID NO: 6), preferably of the sequence KRPSCIGCK (SEQ ID NO: 7).

In a further preferred embodiment, said 7-13 amino-acid sequence fragment is a fragment of any one of the sequences MILNSSTEDGIKRIQDDCPKAGRHNYI (SEQ ID NO: 8), TAMEYRWPFGNYLCK (SEQ ID NO: 9), AIIHRNVFFIENTNITVCAFHYESQNSTLP (SEQ ID NO: 10), DVLIQLGIIRDCR (SEQ ID NO: 11), more preferably of the sequence AFHYESQ (SEQ ID NO: 12).

In a further preferred embodiment, the peptides have a sequence length of 8-13 amino acids, preferably 9-12 amino acids, more preferably 10-12 amino acids, especially wherein at least one of the at least two, preferably each of the peptides consist of the sequence GRPQKRPSCIG (SEQ ID NO: 13) optionally with an N-terminal and/or C-terminal cysteine residue.

According to a further preferred embodiment, the compound further comprises at least one peptide with a sequence length of 7-13 amino acids, wherein the at least one peptide comprises a 7-13 amino-acid sequence fragment of the type-1 angiotensin II receptor (AT1AR) sequence identified by UniProt accession code P30556, preferably of any one of the sequences MILNSSTEDGIKRIQDDCPKAGRHNYI (SEQ ID NO: 8), TAMEYRWPFGNYLCK (SEQ ID NO: 9), AIIHRNVFFIENTNITVCAFHYESQNSTLP (SEQ ID NO: 10), DVLIQLGIIRDCR (SEQ ID NO: 11), more preferably of the sequence AFHYESQ (SEQ ID NO: 12); wherein the at least one peptide is covalently bound to the biopolymer scaffold, preferably via a linker.

Furthermore, also for use in the prevention or treatment of pre-eclampsia, in a preferred embodiment of inventive compound, at least one occurrence of P is $P_a$ and at least one occurrence of P is $P_b$,
  wherein $P_a$ is a peptide with a sequence length of 5-13, preferably 7-13, amino acids,
  wherein $P_b$ is a peptide with a sequence length of 5-13, preferably 7-13, amino acids,
  wherein the entire sequence, optionally with the exception of an N-terminal and/or C-terminal cysteine, of peptide $P_a$ is identical to a sequence fragment of a protein, wherein the protein is identified by UniProt accession code Q1HVF7, P03211, Q13585 or P30556, optionally wherein said sequence fragment comprises at most five, preferably at most four, more preferably at most three, even more preferably at most two, especially at most one amino acid substitutions,
  wherein the entire sequence, optionally with the exception of an N-terminal and/or C-terminal cysteine, of peptide $P_b$ is identical to a sequence fragment of a protein, wherein the protein is identified by UniProt accession code Q1HVF7, P03211, Q13585 or P30556, optionally wherein said sequence fragment comprises at most five, preferably at most four, more preferably at most three, even more preferably at most two, especially at most one amino acid substitutions.

In embodiments, in particular for $P_a$ and/or $P_b$, said sequence fragment of the protein is a fragment of the sequence RPQKRPSCIGCKGTH (SEQ ID NO: 5) or RPQKRPSCIGCKGAH (SEQ ID NO: 6), preferably of the sequence KRPSCIGCK (SEQ ID NO: 7). In further embodiments, in particular for $P_a$ and/or $P_b$, said sequence fragment of the protein is a fragment of any one of the sequences MILNSSTEDGIKRIQDDCPKAGRHNYI (SEQ ID NO: 8), TAMEYRWPFGNYLCK (SEQ ID NO: 9), AIIHRNVFFIENTNITVCAFHYESQNSTLP (SEQ ID NO: 10), DVLIQLGIIRDCR (SEQ ID NO: 11), more preferably of the sequence AFHYESQ (SEQ ID NO: 12). In particular, peptide $P_a$ and/or peptide $P_b$ consist of the sequence GRPQKRPSCIG (SEQ ID NO: 13) optionally with an N-terminal and/or C-terminal cysteine residue.

Further, for stronger reduction of the titre of the undesired antibodies related to pre-eclampsia, in a preferred embodiment, the first peptide n-mer is $P_a$—S—$P_b$ and the second peptide n-mer is $P_a$—S—$P_b$.

Especially in the context of depleting undesired anti-drug antibodies, in yet another preferred embodiment of the present invention, the entire sequence, optionally with the exception of an N-terminal and/or C-terminal cysteine, of at least one occurrence of P, preferably of at least 10% of all occurrences of P, more preferably of at least 25% of all occurrences of P, yet more preferably of at least 50% of all occurrences of P, even more preferably of at least 75% of all occurrences of P, yet even more preferably of at least 90% of all occurrences of P or even of at least 95% of all occurrences of P, especially of all of the occurrences of P, is identical to a sequence fragment of an amino-acid sequence of Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab; optionally wherein said sequence fragment comprises at most five, preferably at most four, more preferably at most three, even more preferably at most two, especially at most one amino acid substitutions.

Especially in the same context, in another preferred embodiment, the entire sequence, optionally with the exception of an N-terminal and/or C-terminal cysteine, of peptide $P_a$ and/or $P_b$ is identical to a sequence fragment of an amino-acid sequence of Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab; optionally wherein said sequence fragment comprises at most five, preferably at most four, more preferably at most three, even more preferably at most two, especially at most one amino acid substitutions.

Especially in the same context of anti-drug antibodies, in another preferred embodiment, the entire sequence, the entire sequence, optionally with the exception of an N-terminal and/or C-terminal cysteine, of peptide $P_a$ is identical to a sequence fragment of an amino-acid sequence and the entire sequence, optionally with the exception of an N-terminal and/or C-terminal cysteine, of peptide $P_b$ is identical to the same or another, preferably another, sequence fragment of the same amino-acid sequence, wherein the amino-acid sequence is an amino-acid sequence of Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab; optionally wherein said sequence fragment and/or said another sequence fragment comprises at most five, preferably at most four, more preferably at most three, even more preferably at most two, especially at most one amino acid substitutions.

In an aspect, the present invention relates to a pharmaceutical composition comprising the inventive and at least one pharmaceutically acceptable excipient.

In embodiments, the composition is prepared for intraperitoneal, subcutaneous, intramuscular and/or intravenous administration. In particular, the composition is for repeated administration (since it is typically non-immunogenic).

In a preference, the molar ratio of peptide P or $P_a$ or $P_b$ to biopolymer scaffold in the composition is from 2:1 to 100:1, preferably from 3:1 to 90:1, more preferably from 4:1 to 80:1, even more preferably from 5:1 to 70:1, yet even more preferably from 6:1 to 60:1, especially from 7:1 to 50:1 or even from 8:10 to 40:1.

In another aspect, the compound of the present invention is for use in therapy.

Preferably, the compound is for use in prevention or treatment of an autoimmune disease in an individual having the autoimmune disease or being at risk of developing the autoimmune disease. These autoimmune diseases include neuromyelitis optica, seropositive neuromyelitis optica spectrum disorders, autoimmune-encephalitis, multiple sclerosis, amyotrophic lateral sclerosis, systemic lupus erythematosus dementia, myasthenia gravis, in particular transient neonatal myasthenia gravis, dilatative Cardiomyopathy, pulmonary hypertension, Sjögren's Syndrome, celiac Disease, Graves Disease, Goodpasture Disease, preeclampsia, Behcet's Disease, systemic sclerosis, hypertension, type I diabetes, type II diabetes, systemic lupus erythematosus, anti N-methyl-D-aspartate receptor (NMDAR) encephalitis, antiphospholipid syndrome, membranous nephropathy, primary biliary cholangitis, amyotrophic lateral sclerosis, Chagas disease cardiomyopathy, immune thrombocytopenic purpura, pemphigus vulgaris, bullous pemphigoid, epidermolysis bullosa acquisita and bullous systemic lupus erythematosus.

The compound of the present invention is also useful for prevention or treatment of transplant rejection in an individual having a transplant or eligible for a transplantation.

In another embodiment, the compound is for use in prevention or treatment of adverse reactions based on anti-drug antibodies or anti-gene-delivery vector antibodies, in particular anti-AAV antibodies, in an individual undergoing therapy with the drug or eligible for therapy with the drug, or in an individual undergoing gene therapy or eligible for gene therapy, Preferably wherein the drug is a peptide or protein, especially selected from the group of enzymes, enzyme inhibitors, antibodies, antibody fragments, antibody mimetics, antibody-drug conjugates, hormones, growth factors, clotting factors and cytokines, preferably wherein the entire sequence, optionally with the exception of an N-terminal and/or C-terminal cysteine, of at least one occurrence of peptide P, or of peptide $P_a$ and/or of peptide $P_b$ is identical to a sequence fragment of an amino-acid sequence of the peptide or protein, optionally wherein said sequence fragment comprises at most five, preferably at most four, more preferably at most three, even more preferably at most two, especially at most one amino acid substitutions. The drug may be e.g. any one of the drugs disclosed herein.

In embodiments, one or more antibodies are present in the individual which are specific for at least one occurrence of peptide P, or for peptide $P_a$ and/or peptide $P_b$, preferably wherein said antibodies are related to said disease.

It is highly preferred that the composition is non-immunogenic in the individual (e.g. it does not comprise an adjuvant or an immunostimulatory substance that stimulates the innate or the adaptive immune system, e.g. such as an adjuvant or a T-cell epitope).

The composition of the present invention may be administered at a dose of 1-1000 mg, preferably 2-500 mg, more preferably 3-250 mg, even more preferably 4-100 mg, especially 5-50 mg, compound per kg body weight of the individual, preferably wherein the composition is administered repeatedly. Such administration may be intraperitoneally, subcutaneously, intramuscularly or intravenously.

In an aspect, the present invention relates to a method of sequestering (or depleting) one or more antibodies present in an individual, comprising
obtaining a pharmaceutical composition as defined herein, wherein the composition is non-immunogenic in the individual and wherein the one or more antibodies present in the individual are specific for at least one occurrence of P, or for peptide $P_a$ and/or peptide $P_b$; and
administering (in particular repeatedly administering, e.g. at least two times, preferably at least three times, more preferably at least five times) the pharmaceutical composition to the individual.

In the context of the present invention, the individual (to be treated) may be a non-human animal, preferably a non-human primate, a sheep, a pig, a dog or a rodent, in particular a mouse.

Preferably, the biopolymer scaffold is autologous with respect to the individual, preferably wherein the biopolymer scaffold is an autologous protein (i.e. murine albumin is used when the individual is a mouse).

In embodiments, the individual is administered a heterologous protein, preferably a heterologous antibody such as a nanobody, and wherein the one or more antibodies present in the individual are specific for said heterologous protein, preferably wherein said administering of the heterologous protein is prior to, concurrent with and/or subsequent to said administering of the pharmaceutical composition.

The heterologous protein (in particular a human or humanized antibody) may for instance be for therapy (in particular immunotherapy) of a malignancy or a cancer. In embodiments, the individual may have the malignancy or the cancer and may e.g. be treated or eligible to be treated or designated to be treated with the heterologous protein such as the antibody.

In a preference, the individual is a non-human animal and the heterologous protein is human or humanized such as a human or humanized antibody (e.g. for preclinical testing of a human or humanized biological such as a monoclonal antibody).

In a further preference, the individual is administered a drug and wherein the one or more antibodies present in the individual are specific for said drug, preferably wherein said administering of the drug is prior to, concurrent with and/or subsequent to said administering of the pharmaceutical composition.

The drug may be any drug as disclosed herein.

In embodiments, the individual is healthy.

In another aspect, the present invention relates to a pharmaceutical composition, comprising the compound of the present invention and further comprising an active agent such as a protein or a peptide and optionally at least one pharmaceutically acceptable excipient, wherein the active agent comprises a peptide fragment with a sequence length of 2-13 amino acids, preferably 3-11 amino acids, more preferably 4-9 amino acids, especially 5-8 amino acids, and wherein the sequence of at least one occurrence of peptide P, or peptide $P_a$ and/or peptide $P_b$, of the compound is at least 70% identical, preferably at least 75% identical, more preferably at least 80% identical, yet more preferably at least 85% identical, even more preferably at least 90% identical, yet even more preferably at least 95% identical, especially completely identical to the sequence of said peptide fragment.

The active agent may be an enzyme, preferably a human enzyme, an antibody, preferably a human or humanized antibody, a hormone, a growth factor, a clotting factor, a cytokine or a gene delivery vector (such as AAV), in particular as disclosed herein.

This composition is preferably for use in inhibition of an immune reaction, preferably an antibody-mediated immune reaction, against the active agent.

This composition is furthermore preferably non-immunogenic in the individual.

In yet another aspect, the present invention relates to a method of inhibiting an immune reaction to a treatment with an active agent in an individual in need of treatment with the active agent, comprising obtaining a pharmaceutical composition as defined above; wherein the compound of the pharmaceutical composition is non-immunogenic in the individual, and administering (preferably repeatedly administering) the pharmaceutical composition to the individual.

In yet even another aspect, the present invention relates to a method of providing the compound of the invention, comprising the steps of identifying at least one individual having an undesired antibody against an antigen, screening a peptide library to identify a peptide mimotope for which the undesired antibody is specific, and providing the compound, wherein at least one occurrence of P of the compound comprises the entire sequence of the peptide mimotope. In this aspect, the compound can be regarded as mimotope-based compound. Mimotopes are described hereinabove. See also Example 4. In general, screening for peptide mimotopes per se is known in the art, see for instance Shanmugam et al.

Mimotope-based compounds of the invention have the following two advantages over compounds based on wild-type epitopes: First, the undesired antibodies, as a rule, have even higher affinities for mimotopes found by screening a peptide library, leading to higher clearance efficiency of the mimotope-based compound. Second, mimotopes further enable avoiding T-cell epitope activity as much as possible (as described hereinabove) in case the wild-type epitope sequence induces such T-cell epitope activity.

In a preference, at least 10% of all occurrences of P of the compound comprise the entire sequence of the peptide mimotope, more preferably wherein at least 25% of all occurrences of P comprise the entire sequence of the peptide mimotope, yet more preferably wherein at least 50% of all occurrences of P comprise the entire sequence of the peptide mimotope, even more preferably wherein at least 75% of all occurrences of P comprise the entire sequence of the peptide mimotope, yet even more preferably wherein at least 90% of all occurrences of P comprise the entire sequence of the peptide mimotope or even wherein at least 95% of all occurrences of P comprise the entire sequence of the peptide mimotope, especially wherein all of the occurrences of P comprise the entire sequence of the peptide mimotope.

In embodiments, the antigen may be a peptide or protein, wherein the sequence of the peptide or protein does not comprise the entire sequence of the peptide mimotope. In other words, the sequence of the peptide mimotope and the wildtype epitope (as found on the peptide or protein) differs in at least one amino acid.

In an especially preferred embodiment, the peptide library comprises circular peptides, as they typically have an even higher affinity to the undesired antibody (see Example 4). The peptide library may e.g. be a phage display library, a peptide microarray library or a soluble peptide library.

In a further preferred embodiment, the screening of the peptide library is performed with a serum obtained from the at least one individual, wherein the serum comprises the undesired antibody. See for instance Gazarian et al. or Leung et al. on how to perform a serum-based screen for mimotopes.

In embodiments, the compound preferably is non-immunogenic in the at least one individual.

In further embodiments, the at least one individual is a non-human animal, preferably a non-human primate, a sheep, a pig, a dog or a rodent, in particular a mouse. The at least one individual may also be human.

In yet another preferred embodiment, the biopolymer scaffold is autologous with respect to the at least one individual, preferably wherein the biopolymer scaffold is an autologous protein.

In embodiments, the at least one individual has been administered a heterologous protein, preferably a heterologous antibody such as a nanobody, and wherein the antigen is said heterologous protein.

In another embodiment, the at least one individual is a non-human animal and the heterologous protein is human or humanized, such as for instance during the development of human or humanized antibodies.

In a further preference, the individual has been administered a drug and the drug is the antigen. The drug may be an enzyme, preferably a human enzyme, an antibody, preferably a human or humanized antibody, a hormone, a growth factor, a clotting factor, a cytokine or a gene delivery vector such as AAV, e.g. as defined herein. For instance, the drug may be Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab.

In embodiments, the individual may be healthy.

According to a further preferred embodiment, the undesired antibody may be an autoantibody of the at least one individual.

In the context of the present invention, for improved bioavailability, it is preferred that the inventive compound has a solubility in water at 25° C. of at least 0.1 µg/ml, preferably at least 1 µg/ml, more preferably at least 10 µg/ml, even more preferably at least 100 µg/ml, especially at least 1000 µg/ml.

The term "preventing" or "prevention" as used herein means to stop a disease state or condition from occurring in a patient or subject completely or almost completely or at least to a (preferably significant) extent, especially when the patient or subject or individual is predisposed to such a risk of contracting a disease state or condition.

The pharmaceutical composition of the present invention is preferably provided as a (typically aqueous) solution, (typically aqueous) suspension or (typically aqueous) emulsion. Excipients suitable for the pharmaceutical composition of the present invention are known to the person skilled in the art, upon having read the present specification, for example water (especially water for injection), saline, Ringer's solution, dextrose solution, buffers, Hank solution, vesicle forming compounds (e.g. lipids), fixed oils, ethyl oleate, 5% dextrose in saline, substances that enhance isotonicity and chemical stability, buffers and preservatives. Other suitable excipients include any compound that does not itself induce the production of antibodies in the patient (or individual) that are harmful for the patient (or individual). Examples are well tolerable proteins, polysaccharides, polylactic acids, polyglycolic acid, polymeric amino acids and amino acid copolymers. This pharmaceutical composition can (as a drug) be administered via appropriate procedures known to the skilled person (upon having read the present specification) to a patient or individual in need thereof (i.e. a patient or individual having or having the risk of developing the diseases or conditions mentioned herein). The preferred route of administration of said pharmaceutical composition is parenteral administration, in particular through intraperitoneal, subcutaneous, intramuscular and/or intravenous administration. For parenteral administration, the pharmaceutical composition of the present invention is preferably provided in injectable dosage unit form, e.g. as a solution (typically as an aqueous solution), suspension or emulsion, formulated in conjunction with the above-defined pharmaceutically acceptable excipients. The dosage and method of administration, however, depends on the individual patient or individual to be treated. Said pharmaceutical composition can be administered in any suitable dosage known from other biological dosage regimens or specifically evaluated and optimised for a given individual. For example, the active agent may be present in the pharmaceutical composition in an amount from 1 mg to 10 g, preferably 50 mg to 2 g, in particular 100 mg to 1 g. Usual dosages can also be determined on the basis of kg body weight of the patient, for example preferred dosages are in the range of 0.1 mg to 100 mg/kg body weight, especially 1 to 10 mg/kg body weight (per administration session). The administration may occur e.g. once daily, once every other day, once per week or once every two weeks. As the preferred mode of administration of the inventive pharmaceutical composition is parenteral administration, the pharmaceutical composition according to the present invention is preferably liquid or ready to be dissolved in liquid such sterile, de-ionised or distilled water or sterile isotonic phosphate-buffered saline (PBS). Preferably, 1000 µg (dry-weight) of such a composition comprises or consists of 0.1-990 µg, preferably 1-900 µg, more preferably 10-200 µg compound, and option-ally 1-500 µg, preferably 1-100 µg, more preferably 5-15 µg (buffer) salts (preferably to yield an isotonic buffer in the final volume), and optionally 0.1-999.9 µg, preferably 100-999.9 µg, more preferably 200-999 µg other excipients. Preferably, 100 mg of such a dry composition is dissolved in sterile, de-ionised/distilled water or sterile isotonic phosphate-buffered saline (PBS) to yield a final volume of 0.1-100 ml, preferably 0.5-20 ml, more preferably 1-10 ml.

It is evident to the skilled person that active agents and drugs described herein can also be administered in salt-form (i.e. as a pharmaceutically acceptable salt of the active agent). Accordingly, any mention of an active agent herein shall also include any pharmaceutically acceptable salt forms thereof.

Methods for chemical synthesis of peptides used for the compound of the present invention are well-known in the art. Of course, it is also possible to produce the peptides using recombinant methods. The peptides can be produced in microorganisms such as bacteria, yeast or fungi, in eukaryotic cells such as mammalian or insect cells, or in a recombinant virus vector such as adenovirus, poxvirus, herpesvirus, Simliki forest virus, baculovirus, bacteriophage, sindbis virus or sendai virus. Suitable bacteria for producing the peptides include *E. coli, B. subtilis* or any other bacterium that is capable of expressing such peptides. Suitable yeast cells for expressing the peptides of the present invention include *Saccharomyces cerevisiae, Schizosaccharomyces pombe, Candida*, Pichiapastoris or any other yeast capable of expressing peptides. Corresponding means and methods are well known in the art. Also, methods for isolating and purifying recombinantly produced peptides are well known in the art and include e.g. gel filtration, affinity chromatography, ion exchange chromatography etc.

Beneficially, cysteine residues are added to the peptides at the N- and/or C-terminus to facilitate coupling to the biopolymer scaffold, especially.

To facilitate isolation of said peptides, fusion polypeptides may be made wherein the peptides are translationally fused (covalently linked) to a heterologous polypeptide which enables isolation by affinity chromatography. Typical heterologous polypeptides are His-Tag (e.g. His6; 6 histidine residues), GST-Tag (Glutathione-S-transferase) etc. The fusion polypeptide facilitates not only the purification of the peptides but can also prevent the degradation of the peptides during the purification steps. If it is desired to remove the heterologous polypeptide after purification, the fusion polypeptide may comprise a cleavage site at the junction between the peptide and the heterologous polypeptide. The cleavage site may consist of an amino acid sequence that is cleaved with an enzyme specific for the amino acid sequence at the site (e.g. proteases).

The coupling/conjugation chemistry used to link the peptides/peptide n-mers to the biopolymer scaffold (e.g. via heterobifunctional compounds such as GMBS and of course also others as described in "Bioconjugate Techniques", Greg T. Hermanson) or used to conjugate the spacer to the peptides in the context of the present invention can also be selected from reactions known to the skilled in the art. The biopolymer scaffold itself may be recombinantly produced or obtained from natural sources.

Herein, the term "specific for"—as in "molecule A specific for molecule B"—means that molecule A has a binding preference for molecule B compared to other molecules in an individual's body. Typically, this entails that molecule A (such as an antibody) has a dissociation constant (also called "affinity") in regard to molecule B (such as the antigen, specifically the binding epitope thereof) that is lower than (i.e. "stronger than") 1000 nM, preferably lower than 100 nM, more preferably lower than 50 nM, even more preferably lower than 10 nM, especially lower than 5 nM.

Herein, "UniProt" refers to the Universal Protein Resource. UniProt is a comprehensive resource for protein sequence and annotation data. UniProt is a collaboration between the European Bioinformatics Institute (EMBL-EBI), the SIB Swiss Institute of Bioinformatics and the Protein Information Resource (PIR). Across the three institutes more than 100 people are involved through different tasks such as database curation, software development and support. Website: http://www.uniprot.org/

Entries in the UniProt databases are identified by their accession codes (referred to herein e.g. as "UniProt accession code" or briefly as "UniProt" followed by the accession code), usually a code of six alphanumeric letters (e.g. "Q1HVF7"). If not specified otherwise, the accession codes used herein refer to entries in the Protein Knowledgebase (UniProtKB) of UniProt. If not stated otherwise, the UniProt database state for all entries referenced herein is of 13 Feb. 2019 (UniProt/UniProtKB Release 2019_02).

In the context of the present application, sequence variants (designated as "natural variant" in UniProt) are expressly included when referring to a UniProt database entry.

"Percent (%) amino acid sequence identity" or "X % identical" (such as "70% identical") with respect to a reference polypeptide or protein sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2, Megalign (DNASTAR) or the "needle" pairwise sequence alignment application of the EMBOSS software package. Those skilled in the art can determine appropriate parameters for aligning sequences, including any algorithms needed to achieve maximal alignment over the full length of the sequences being compared. For purposes herein, however, % amino acid sequence identity values are calculated using the sequence alignment of the computer programme "needle" of the EMBOSS software package (publicly available from European Molecular Biology Laboratory; Rice et al., EMBOSS: the European Molecular Biology Open Software Suite, Trends Genet. 2000 June; 16(6):276-7, PMID: 10827456).

The needle programme can be accessed under the web site http://www.ebi.ac.uk/Tools/psa/emboss_needle/or downloaded for local installation as part of the EMBOSS package from http://emboss.sourceforge.net/. It runs on many widely-used UNIX operating systems, such as Linux.

To align two protein sequences, the needle programme is preferably run with the following parameters:

Commandline: needle-auto-stdout-asequence SEQUENCE_FILE A—bsequence SEQUENCE_FILE B—datafile EBLOSUM62—gapopen 10.0—gapextend 0.5—endopen 10.0—endextend 0.5—aformat3 pair—sprotein1—sprotein2 (Align_format: pair Report file: stdout)

The % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program needle in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. In cases where "the sequence of A is more than N % identical to the entire sequence of B", Y is the entire sequence length of B (i.e. the entire number of amino acid residues in B). Unless specifically stated otherwise, all % amino acid sequence identity values used herein are obtained as described in the immediately preceding paragraph using the needle computer program.

The present invention further relates to the following embodiments:

Embodiment 1. A compound comprising
  a biopolymer scaffold and at least
  a first peptide n-mer of the general formula:

P(—S—P)$_{(n-1)}$ and a second peptide n-mer of the general formula: P(—S—P)$_{(n-1)}$;
  wherein, independently for each occurrence, P is a peptide with a sequence length of 2-13 amino acids, preferably 3-11 amino acids, more preferably 4-9 amino acids, especially 5-8 amino acids, and S is a non-peptide spacer,
  wherein, independently for each of the peptide n-mers, n is an integer of at least 1, preferably of at least 2, more preferably of at least 3, especially of at least 4,
  wherein each of the peptide n-mers is bound to the biopolymer scaffold, preferably via a linker each.

Embodiment 2. The compound of embodiment 1, wherein at least one occurrence of P is a circularized peptide, preferably wherein at least 10% of all occurrences of P are circularized peptides, more preferably wherein at least 25% of all occurrences of P are circularized peptides, yet more preferably wherein at least 50% of all occurrences of P are circularized peptides, even more preferably wherein at least 75% of all occurrences of P are circularized peptides, yet even more preferably wherein at least 90% of all occurrences of P are circularized peptides or even wherein at least 95% of all occurrences of P are circularized peptides, especially wherein all of the occurrences of P are circularized peptides.

Embodiment 3. The compound of embodiment 1 or 2, wherein, independently for each of the peptide n-mers, n is at least 2, more preferably at least 3, especially at least 4.

Embodiment 4. The compound of any one of embodiments 1 to 3, wherein, independently for each of the peptide n-mers, n is less than 10, preferably less than 9, more preferably less than 8, even more preferably less than 7, yet even more preferably less than 6, especially less than 5.

Embodiment 5. The compound of any one of embodiments 1 to 4, wherein, for each of the peptide n-mers, n is 2.

Embodiment 6. The compound of any one of embodiments 1 to 5, wherein at least one occurrence of P is $P_a$ and/or at least one occurrence of P is $P_b$,
wherein $P_a$ is a peptide with a sequence length of 2-13 amino acids, preferably 3-11 amino acids, more preferably 4-9 amino acids, especially 5-8 amino acids,
wherein $P_b$ is a peptide with a sequence length of 2-13 amino acids, preferably 3-11 amino acids, more preferably 4-9 amino acids, especially 5-8 amino acids.

Embodiment 7. The compound of any one of embodiments 1 to 6, wherein, independently for each occurrence, P is $P_a$ or $P_b$.

Embodiment 8. The compound of any one of embodiments 1 to 7, wherein, in the first peptide n-mer, each occurrence of P is $P_a$ and, in the second peptide n-mer, each occurrence of P is $P_b$.

Embodiment 9. The compound of any one of embodiments 1 to 8, wherein
the first peptide n-mer is $P_a$—S—$P_a$ and the second peptide n-mer is $P_a$—S—$P_a$; or
the first peptide n-mer is $P_a$—S—$P_a$ and the second peptide n-mer is $P_b$—S—$P_b$;
the first peptide n-mer is $P_b$—S—$P_b$ and the second peptide n-mer is $P_b$—S—$P_b$;
the first peptide n-mer is $P_a$—S—$P_b$ and the second peptide n-mer is $P_a$—S—$P_b$;
the first peptide n-mer is $P_a$—S—$P_b$ and the second peptide n-mer is $P_a$—S—$P_a$; or
the first peptide n-mer is $P_a$—S—$P_b$ and the second peptide n-mer is $P_b$—S—$P_b$.

Embodiment 10. A compound comprising
a biopolymer scaffold and at least
a first peptide n-mer which is a peptide dimer of the formula $P_a$—S—$P_a$ or $P_a$—S—$P_b$,
wherein $P_a$ is a peptide with a sequence length of 2-13 amino acids, preferably 3-11 amino acids, more preferably 4-9 amino acids, especially 5-8 amino acids, $P_b$ is a peptide with a sequence length of 2-13 amino acids, preferably 3-11 amino acids, more preferably 4-9 amino acids, especially 5-8 amino acids, and S is a non-peptide spacer,
wherein the first peptide n-mer is bound to the biopolymer scaffold, preferably via a linker.

Embodiment 11. The compound of embodiment 10, further comprising a second peptide n-mer which is a peptide dimer of the formula $P_b$—S—$P_b$ or $P_a$—S—$P_b$, wherein the second peptide n-mer is bound to the biopolymer scaffold, preferably via a linker.

Embodiment 12. The compound of any one of embodiments 1 to 9 and 11, wherein the first peptide n-mer is different from the second peptide n-mer.

Embodiment 13. The compound of any one of embodiments 6 to 12, wherein the peptide $P_a$ is different from the peptide $P_b$, preferably wherein the peptide $P_a$ and the peptide $P_b$ are two different epitopes of the same antigen or two different epitope parts of the same epitope.

Embodiment 14. The compound of any one of embodiments 6 to 13, wherein the peptide $P_a$ and the peptide $P_b$ comprise the same amino-acid sequence fragment, wherein the amino-acid sequence fragment has a length of at least 2 amino acids, preferably at least 3 amino acids, more preferably at least 4 amino acids, yet more preferably at least 5 amino acids, even more preferably at least 6 amino acids, yet even more preferably at least 7 amino acids, especially at least 8 amino acids or even at least 9 amino acids.

Embodiment 15. The compound of any one of embodiments 6 to 14, wherein $P_a$ and/or $P_b$ is circularized.

Embodiment 16. The compound of any one of embodiments 1 to 15, wherein the compound comprises a plurality of said first peptide n-mer and/or a plurality of said second peptide n-mer.

Embodiment 17. The compound of any one of embodiments 1 to 16, wherein the biopolymer scaffold is a protein, preferably a mammalian protein such as a human protein, a non-human primate protein, a sheep protein, a pig protein, a dog protein or a rodent protein.

Embodiment 18. The compound of embodiment 17, wherein the biopolymer scaffold is a globulin.

Embodiment 19. The compound of embodiment 18, wherein the biopolymer scaffold is selected from the group consisting of immunoglobulins, alpha1-globulins, alpha2-globulins and beta-globulins.

Embodiment 20. The compound of embodiment 19, wherein the biopolymer scaffold is selected from the group consisting of immunoglobulin G, haptoglobin and transferrin.

Embodiment 21. The compound of embodiment 20, wherein the biopolymer scaffold is haptoglobin.

Embodiment 22. The compound of embodiment 17, wherein the biopolymer scaffold is an albumin.

Embodiment 23. The compound of any one of embodiments 1 to 22, wherein the compound is non-immunogenic in a mammal, preferably in a human, in a non-human primate, in a sheep, in a pig, in a dog or in a rodent.

Embodiment 24. The compound of any one of embodiments 1 to 23, wherein the compound is for intracorporeal sequestration (or intracorporeal depletion) of at least one antibody in an individual, preferably in the bloodstream of the individual and/or for reduction of the titre of at least one antibody in the individual, preferably in the bloodstream of the individual.

Embodiment 25. The compound of any one embodiments 1 to 24, wherein the compound further comprises at least
a third peptide n-mer of the general formula:

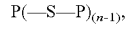

$$P(-S-P)_{(n-1)},$$

wherein, independently for each occurrence, P is a peptide with a sequence length of 2-13 amino acids, preferably 3-11 amino acids, more preferably 4-9 amino acids, especially 5-8 amino acids, and S is a non-peptide spacer,
preferably wherein each occurrence of P is $P_c$, wherein $P_c$ is a peptide with a sequence length of 2-13 amino acids, preferably 3-11 amino acids, more preferably 4-9 amino acids, especially 5-8 amino acids,
more preferably wherein $P_c$ is circularized;
a fourth peptide n-mer of the general formula:

$$P(\text{—}S\text{—}P)_{(n-1)},$$

wherein, independently for each occurrence, P is a peptide with a sequence length of 2-13 amino acids, preferably 3-11 amino acids, more preferably 4-9 amino acids, especially 5-8 amino acids, and S is a non-peptide spacer,
preferably wherein each occurrence of P is $P_d$, wherein $P_d$ is a peptide with a sequence length of 2-13 amino acids, preferably 3-11 amino acids, more preferably 4-9 amino acids, especially 5-8 amino acids,
more preferably wherein $P_d$ is circularized;
a fifth peptide n-mer of the general formula:

$$P(\text{—}S\text{—}P)_{(n-1)},$$

wherein, independently for each occurrence, P is a peptide with a sequence length of 2-13 amino acids, preferably 3-11 amino acids, more preferably 4-9 amino acids, especially 5-8 amino acids, and S is a non-peptide spacer,
preferably wherein each occurrence of P is $P_e$, wherein $P_e$ is a peptide with a sequence length of 2-13 amino acids, preferably 3-11 amino acids, more preferably 4-9 amino acids, especially 5-8 amino acids,
more preferably wherein $P_e$ is circularized;
a sixth peptide n-mer of the general formula:

$$P(\text{—}S\text{—}P)_{(n-1)},$$

wherein, independently for each occurrence, P is a peptide with a sequence length of 2-13 amino acids, preferably 3-11 amino acids, more preferably 4-9 amino acids, especially 5-8 amino acids, and S is a non-peptide spacer,
preferably wherein each occurrence of P is $P_f$, wherein $P_f$ is a peptide with a sequence length of 2-13 amino acids, preferably 3-11 amino acids, more preferably 4-9 amino acids, especially 5-8 amino acids,
more preferably wherein $P_f$ is circularized;
a seventh peptide n-mer of the general formula:

$$P(\text{—}S\text{—}P)_{(n-1)},$$

wherein, independently for each occurrence, P is a peptide with a sequence length of 2-13 amino acids, preferably 3-11 amino acids, more preferably 4-9 amino acids, especially 5-8 amino acids, and S is a non-peptide spacer,
preferably wherein each occurrence of P is $P_g$, wherein $P_g$ is a peptide with a sequence length of 2-13 amino acids, preferably 3-11 amino acids, more preferably 4-9 amino acids, especially 5-8 amino acids,
more preferably wherein $P_g$ is circularized;
a eighth peptide n-mer of the general formula:

$$P(\text{—}S\text{—}P)_{(n-1)},$$

wherein, independently for each occurrence, P is a peptide with a sequence length of 2-13 amino acids, preferably 3-11 amino acids, more preferably 4-9 amino acids, especially 5-8 amino acids, and S is a non-peptide spacer,
preferably wherein each occurrence of P is $P_h$, wherein $P_h$ is a peptide with a sequence length of 2-13 amino acids, preferably 3-11 amino acids, more preferably 4-9 amino acids, especially 5-8 amino acids,
more preferably wherein $P_h$ is circularized;
a ninth peptide n-mer of the general formula:

$$P(\text{—}S\text{—}P)_{(n-1)},$$

wherein, independently for each occurrence, P is a peptide with a sequence length of 2-13 amino acids, preferably 3-11 amino acids, more preferably 4-9 amino acids, especially 5-8 amino acids, and S is a non-peptide spacer,
preferably wherein each occurrence of P is $P_i$, wherein $P_i$ is a peptide with a sequence length of 2-13 amino acids, preferably 3-11 amino acids, more preferably 4-9 amino acids, especially 5-8 amino acids,
more preferably wherein $P_i$ is circularized;
a tenth peptide n-mer of the general formula:

$$P(\text{—}S\text{—}P)_{(n-1)},$$

wherein, independently for each occurrence, P is a peptide with a sequence length of 2-13 amino acids, preferably 3-11 amino acids, more preferably 4-9 amino acids, especially 5-8 amino acids, and S is a non-peptide spacer,
preferably wherein each occurrence of P is $P_j$, wherein $P_j$ is a peptide with a sequence length of 2-13 amino acids, preferably 3-11 amino acids, more preferably 4-9 amino acids, especially 5-8 amino acids,
more preferably wherein $P_j$ is circularized.

Embodiment 26. The compound of any one of embodiments 1 to 25, wherein the entire sequence, optionally with the exception of an N-terminal and/or C-terminal cysteine, of at least one occurrence of P, preferably of at least 10% of all occurrences of P, more preferably of at least 25% of all occurrences of P, yet more preferably of at least 50% of all occurrences of P, even more preferably of at least 75% of all occurrences of P, yet even more preferably of at least 90% of all occurrences of P or even of at least 95% of all occurrences of P, especially of all of the occurrences of P, is identical to a sequence fragment of a protein, wherein the protein is identified by one of the following UniProt accession codes:

P01023, A8K2U0, P49588, Q5JTZ9, O95477, Q8IZY2, P08183, P33527, O15438, Q961U4, P00519, P42684, Q9BYF1, P22303, Q99798, P68133, P60709, P63261, P12814, O43707, P61158, Q13705, P37023, O75077, Q9UKQ2, Q76LX8, Q6ZMM2, P35611, P07327, P00325, P35348, P25100, P08588, P07550, P25098, P35626, P30566, P43652, P02771, Q5U5Z8, Q15109, P35573, Q9UL18, Q9UKV8, O00468, P01019, P30556, Q09666, P02765, O43918, Q9Y6K8, Q02952, P14550, P15121, O95154, P02768, P00352, P49189, Q9UM73, P09923, P05187, P03971, P49418, P03950, Q9BY76, Q15327, P15144, P04083, P50995, P07355, Q3ZCQ2, P12429, P09525, P08758, P08133, O76027, Q13367, P27695, Q9BZZ5, P02647, P04114, P02749, P05067, P29972, P55087, Q8N726, P05089, Q9UNA1, P52566, Q99819, Q15052, P07306, P04424, P08243, Q9BXN1, P15336, P13637, P05026, P98194, P20648, P51164, P06576, P48047, P54252, Q8WXX7, P01185, P25311, Q9H6S1, P61769, Q13072, O75531, Q99728, P10415, P41182, P11274, O14503, Q93088, O00499, O15392, P35226, P12643, P18075, Q8N8U9, Q13873, P17213, Q9NP55, Q96DR5, Q8TDL5, P15056, Q7Z569, P38398, P51587, Q58F21, Q8IWQ3, Q8NE79, Q9Y224, Q13901, P02745, P01024, P00915, P00918, P07451, O00555, Q00975, Q9NY47, Q9Y698, Q8TC20, Q05682, P27482, P27797, P27824,

P04632, P52907, P42574, Q14790, P31415, P41180, P20810, O15446, P04040, Q9NTU7, Q5M9N0, Q3V6T2, P10147, P13501, P20248, P14635, P24385, Q8ND76, P51681, P49368, P48643, P50990, Q9NZQ7, P28906, P16671, P04234, P15529, P08174, P13987, P01732, P21926, P30305, P12830, P55291, P22223, P55283, P06493, P42771, P51861, Q01850, Q9H211, P13688, P06731, Q9UNI1, P49450, P07199, Q03188, Q02224, P49454, Q9H3R5, Q92674, Q6IPU0, Q7L2Z9, A8MT69, Q5JTW2, P00751, P08603, Q03591, P36980, Q02985, Q9P2M7, O95992, Q14839, P10645, P36222, Q15782, Q9UKJ5, Q9Y259, P11229, P08172, P20309, P08173, P08912, P02708, Q9UGM1, P11230, Q8NCH0, Q99828, O75339, Q14011, Q07065, P12277, Q96MX0, P06732, A8K714, O95832, O75508, P30622, Q96KN2, Q12860, Q02246, Q8IWV2, O94779, Q9UQ52, P78357, Q9UHC6, Q7Z7A1, P38432, Q5TAT6, Q9UMD9, P02452, Q01955, P29400, Q14031, P12111, Q02388, Q9Y215, P49747, Q14019, P00450, P16870, Q8TCG5, P17927, Q9NS37, Q9UJA2, P02741, P02511, P53674, O95825, O75390, Q9Y600, P04141, P09919, P0DML2, Q14406, Q6UVK1, Q01459, Q9GZU7, P16410, P35222, P53634, P07339, P08311, Q14247, O60494, Q14999, Q86UP6, P61073, P05108, P05093, P04798, P05177, P08686, P11509, P20813, P33261, P11712, P10635, P05181, P08684, Q8N907, P09172, P43146, P07585, P20711, Q16832, Q9NR30, O00571, Q86XP3, Q9NY93, O75398, P35659, P17661, Q96SL1, O94907, P10515, P09622, P36957, P24855, Q8NFT8, O00429, Q8N608, P27487, P42658, Q14195, Q9BPU6, P21728, P14416, Q08554, Q02487, Q14574, Q02413, Q14126, P32926, Q86SJ6, P15924, Q03001, Q9NRD8, Q05923, O75923, O95905, Q9NTX5, Q16610, O43854, P25101, Q15075, P68104, O00418, O95967, P01133, P00533, P20042, P38919, Q04637, P08246, Q12926, Q14576, P26378, P15502, P19622, P06733, P09104, P22413, O43768, P11171, P16422, P07099, P34913, P01588, P11678, P58107, P04626, Q96RT1, Q8IUD2, Q14264, P10768, P03372, Q9Y603, Q92817, Q9Y3B2, Q01780, Q13868, Q9NQT5, Q9NPD3, Q9NQT4, Q5RKV6, Q15024, Q96B26, Q06265, P15311, P00488, P08709, P00451, P00740, P15090, Q14320, P48023, P49327, Q8TES7, P22087, P35555, Q75N90, P09467, P12319, O75015, O75636, Q7L513, P02675, P11362, P62942, Q9UIM3, P20930, Q14315, O75955, Q14254, O43155, P35916, P02751, Q04609, P01225, Q12841, O95954, P02794, P02792, P09958, P35637, P51114, Q9UM11, P35575, O95166, P60520, Q9UBS5, O75899, Q99259, Q05329, Q13065, P22466, Q14376, P04406, P41250, P01350, P15976, P50440, P02774, P01275, Q8N6F7, P23434, P55107, P50395, P56159, Q9UJY5, P01241, P01286, Q9UBU3, P09681, O14908, P29033, Q9NS71, Q6ZMI3, P23415, P15104, Q61B77, P49915, Q13823, P01148, P30968, Q92805, Q08379, Q08378, Q13439, A6NI86, A8MQT2, Q14789, P07359, P55259, P40197, Q9HCN6, P14770, Q9NQX3, P06744, Q13098, P24298, P18283, P42261, P42262, P42263, P48058, O43424, P39086, Q13002, Q16478, Q05586, Q12879, Q13224, Q4V328, Q13255, P41594, P28799, P07492, P08263, P21266, P78417, P09211, Q00403, P35269, P25092, P08236, P02724, P07305, P16104, O75367, P84243, P12081, Q96D42, P68871, Q13547, Q92769, O15379, P56524, Q9UQL6, P19113, Q9UBI9, P51858, Q00341, Q9NRV9, O00291, O75146, P54198, P16402, P58876, P62805, P19367, P09429, P26583, P04035, Q01581, P54868, P05114, P05204, Q14541, P09651, P22626, Q99729, Q14103, P52597, P31943, P31942, P61978, P14866, Q8WVV9, Q9NSC5, Q99714, Q7Z5P4, P14060, P08238, P14625, P0DMV8, P0DMV9, P34932, P11021, P11142, P04792, Q12988, P10809, Q92598, P08908, Q13639, Q9Y4L1, P10997, Q05084, Q9UMF0, O75874, Q5TF58, Q16666, Q9BYX4, P01563, P01574, P01579, Q9NWB7, P05019, P08069, P01344, Q9NZI8, Q9Y6M1, O00425, P11717, P18065, P17936, P01876, P01877, P01854, P01857, P01859, P01860, P01861, A6NGN9, Q8N6C5, P22301, Q13651, Q08334, Q14005, Q16552, Q96PD4, Q14116, P01583, P01584, P14778, P60568, Q9GZX6, P08700, P05112, P05231, P40189, Q96LU5, Q9NV31, P29218, O14732, P12268, Q9NQS7, P01308, Q96T92, P06213, P46940, Q14653, Q13568, P35568, P17301, P08514, P23229, P20701, P11215, P05107, P05106, P16144, Q14643, Q9Y6Y0, O60674, P17275, Q15046, P16389, P22459, Q9UK17, Q9NZI2, Q9NS61, P78508, P48050, P51787, O43525, Q8N513, Q6PI47, P35968, Q9Y4F3, Q96Q89, P43626, P43628, Q5JT82, Q53G59, Q8IXQ5, Q9UKR3, P03952, P26715, P26717, Q13241, P13645, P02533, P19012, P08779, Q04695, P05783, P08727, P12035, Q8N1N4, P05787, Q9NSB2, O15230, P11047, P13473, Q14739, P31025, P13796, P07195, P01130, Q9Y2U8, P09382, P05162, P17931, Q08380, Q3ZCW2, O95970, Q5TDP6, P22888, P49917, P07098, P02545, P20700, Q03252, P61968, P29536, P08519, Q07954, P98164, O75096, Q8TF66, Q32MZ4, Q8ND56, Q9Y4ZO, P02788, Q17RY6, P20645, Q8NHW3, P20916, P43358, O15479, O60732, Q9H0U3, P46821, P11137, Q16584, O43318, P45984, Q16644, P21941, O00339, P56270, P02144, Q9UIS9, P11226, P02686, Q01726, P32245, Q8IVS2, Q99705, Q969V1, Q8TDD5, Q8NE86, P40925, Q00987, O00255, P50579, P46013, Q16655, P03956, P45452, P08253, P09237, P14780, Q13201, Q13875, Q16653, Q13724, Q14149, Q9UBU8, O00566, Q99547, P40238, P05164, Q00013, Q9NZW5, P25189, P22897, Q9Y605, P82909, P43246, P52701, Q13421, P26038, Q9UJ68, P26927, Q13043, Q04912, Q9NZJ7, Q86UE4, P15941, Q8WX17, O15146, Q9UIF7, P10242, P01106, Q99417, P12524, Q8N699, P12882, P35580, P35749, Q9UKX3, Q7Z406, Q9Y2K3, Q9UKX2, P11055, Q9Y623, P13533, P12883, A7E2Y1, P13535, P35579, B0I1T2, P54296, Q14CX7, E9PAV3, Q13765, Q8WY41, Q96159, Q9UBB6, Q9UHB4, Q00604, P28331, P20929, P07196, P07197, Q8NG66, Q8TD19, O60524, O94856, P01138, Q8N4C6, P30414, P59047, Q8N427, Q13253, Q15155, P29475, P51513, Q9UNW9, P55786, O60500, P06748, P01160, P17342, P01303, Q9Y5X4, Q8IXM6, Q9ULB1, Q9HDB5, Q9Y4CO, Q9NXX6, P04629, Q16620, Q16288, Q02818, P80303, Q14980, P49790, Q8TEM1, O15504, Q14990, Q5BJF6, Q9ULJ1, Q6UX06, P78380, P41143, P35372, Q9P0S3, Q92791, Q9UQ80, Q13310, Q9UM07, Q7Z2X7, Q5JRK9, Q96GU1, Q13177, Q99497, P09874, P40424, Q15154, P12004, P29120, Q8WUM4, O95263, O76083, P16234, P09619, O00330, P30101, Q8N165, O00151, Q5T2W1, P16284, P02776, P10720, P35080, P18669, P00558, O95394, P35232, Q99623, Q9BVI0, Q92576, O43175, P11309, O75364, Q9Y446, P04054, Q13018, P16885, Q15149, Q9H7P9, P40967, P29590, Q01453,

Q9NR77, P54277, P16233, P54317, Q8ND90, Q9UL42, P00491, Q9H9Y6, O14802, Q99575, P16435, Q15063, Q01851, Q12837, Q15181, P62937, O60437, P35813, P01298, Q9HAZ2, P32119, Q13162, P30041, P13727, Q92954, P17612, P17252, Q01236, P04553, P04554, O60678, P04070, Q9UNN8, P54821, Q99811, P07477, P24158, Q9BXM0, O43653, O75475, P20618, P40306, P49721, P28074, P28062, P28065, P61289, Q6PGN9, P26599, Q8WV60, P01270, P06454, Q06124, Q9Y2R2, P08575, Q12913, Q16849, Q92932, Q86Y79, Q9UHX1, P20472, Q9BRP8, P51153, Q9UI14, Q15276, P63244, Q92878, Q06609, P04049, Q15311, Q9UKM9, Q14498, P38159, P10745, Q06330, P53805, O95199, Q9P258, P35243, P46063, P05451, Q8IX06, P57771, P08100, P12271, O60930, O00584, Q9ULK6, Q99942, Q9UBF6, P13489, O75116, Q01973, P15927, Q9Y2JO, Q9UNE2, Q02878, P05388, P05386, P05387, Q9BUL9, P78346, P78345, P62277, P60866, O75676, O43159, Q15404, O00442, Q92541, Q9NQC3, Q9Y265, Q9Y230, P48443, P21817, Q92736, P31151, P04271, P0DJI8, P0DJI9, P10523, P49591, O43290, Q99590, Q8WTV0, Q14108, P13521, P05408, Q14524, Q9BWW7, P34741, Q86SQ7, Q9UDX4, Q13228, P16109, P04279, Q9HC62, P49908, Q9HD40, P01009, P05543, P30740, P29508, P48594, P35237, P05121, P07093, P05155, Q9BYW2, Q7Z333, Q8N474, Q9BWM7, Q99961, O15266, O60902, Q9NYZ4, Q9Y336, Q9H0K1, Q14190, Q13239, Q14493, Q9H0C2, P12235, P05141, Q9H2B4, O43511, P11168, Q8IWU4, O00400, P08195, Q8IWA5, P48751, Q9Y6R1, Q9BRV3, Q92911, P37840, O76070, P08621, P09012, P14678, P09234, P62314, P62316, P62318, P62304, P62306, P62308, P63162, O14512, P00441, P04179, Q9BQB4, O00570, P56693, P35716, O15370, O60248, Q9UN79, O95416, Q9H6I2, P35713, P48431, Q9Y651, P41225, O94993, Q06945, P35711, P35712, Q9BT81, P57073, P48436, P08047, P23497, Q13342, Q9H930, Q15506, Q8N0X2, P00995, P16150, O43791, P10451, Q8TCT8, Q8TCT7, Q8TCT6, Q13813, Q13501, P10124, P61011, O76094, Q05066, P05455, O43805, P61278, Q13586, Q9P246, P31948, P49842, P16949, Q7Z7C7, Q13033, O75558, P61266, Q13190, Q8IWZ8, Q9Y2ZO, Q8IWU6, P63165, P61956, P17600, P08247, P21579, P37837, Q15633, Q13148, P26639, Q9NYW0, P20226, O60806, P24557, P17987, O60522, O14746, P02787, P05549, Q92734, P10646, P02786, P01266, P01137, P21980, Q08188, P49221, P07204, P40225, P10827, P10828, Q9UPZ6, P31483, P29401, Q9Y490, O60602, Q8TDI7, P17152, P42167, P42166, P01375, O00300, P43489, P19237, P48788, P19429, P13805, P45379, P45378, P09430, Q8NDV7, P11387, Q969P6, P11388, Q13472, O95985, P04637, Q9H3D4, O15350, P60174, P09493, P07202, P12270, P56180, O43280, Q92519, Q96RU7, P19474, O15164, Q9UPN9, Q6AZZ1, P10155, P48995, Q13507, Q7Z4N2, Q7Z2W7, Q9HBA0, Q9BZW7, P01222, P16473, Q9H2G4, Q14166, Q8WZ42, P02766, P07437, O00294, Q15672, Q9P2K2, Q86VQ3, Q6A555, P14679, Q9BZF9, Q13404, Q14139, O95155, P11441, Q9UMX0, P17480, P09936, P15374, Q9Y3C8, P19224, P16662, P07911, Q8TCY9, Q9Y6N9, Q13107, P63027, Q15836, P18206, P55072, P21796, P08670, P04275, O75083, Q14191, P98170, Q13426, P13010, P12956, P67809, Q9Y2T7, O43829, Q13105, Q15915, O95409, Q8N9L1, Q9UDV7, Q9Y3S2, Q9UL40, Q14966, Q9H0M5, Q9Y5V0, Q96C28, Q9H5H4, A9RAI0, B5SUY7, O41855, O56137, O56139, P03135, P04133, P04882, P08362, P10269, P12538, P69353, Q5Y9B2, Q5Y9B4, Q65311, Q6JC40, Q6VGT5, Q8JQF8, Q8JQG0, Q98654, Q9WBP8, Q9YIJ1, Q1HVF7, P03211, Q13585, P04233, O15523, O14602, Q30201, P01891, P01892, P04439, P05534, P10314, P10316, P13746, P16188, P16189, P16190, P18462, P30443, P30447, P30450, P30453, P30455, P30456, P30457, P30459, P30512, Q09160, P01889, P03989, P10319, P18463, P18464, P18465, P30460, P30461, P30462, P30464, P30466, P30475, P30479, P30480, P30481, P30483, P30484, P30485, P30486, P30487, P30488, P30490, P30491, P30492, P30493, P30495, P30498, P30685, Q04826, Q29718, Q29836, Q29940, Q31610, Q31612, Q95365, P04222, P10321, P30499, P30501, P30504, P30505, P30508, P30510, Q07000, Q29865, Q29960, Q29963, Q95604, Q9TNN7, P28067, P28068, P06340, P13765, P20036, P04440, P01909, P01906, P01920, P05538, P01903, P01911, P01912, P04229, P13760, P13761, P20039, Q29974, Q30134, Q30167, Q5Y7A7, Q951E3, Q9GIY3, Q9TQE0, P79483, P13762, Q30154, P13747, P30511, P17693, Q9BY66, Q29983, Q29980, P22090, Q03519, O14607, P08048;

in particular wherein the sequence fragment comprises or consists of the AAV-8 capsid protein sequence LQQQNT (SEQ ID NO: 18), TTTGQNNNS (SEQ ID NO: 19) or GTANTQ (SEQ ID NO: 20);

optionally wherein the sequence fragment comprises at most five, preferably at most four, more preferably at most three, even more preferably at most two, especially at most one amino acid substitutions.

Embodiment 27. The compound of any one of embodiments 1 to 26, wherein the entire sequence, optionally with the exception of an N-terminal and/or C-terminal cysteine, of peptide $P_a$ is identical to a sequence fragment of a protein, wherein the protein is identified by one of the UniProt accession codes listed in embodiment 26;

optionally wherein said sequence fragment comprises at most five, preferably at most four, more preferably at most three, even more preferably at most two, especially at most one amino acid substitutions.

Embodiment 28. The compound of any one of embodiments 1 to 27, wherein the entire sequence, optionally with the exception of an N-terminal and/or C-terminal cysteine, of peptide $P_b$ is identical to a sequence fragment of a protein, wherein the protein is identified by one of the UniProt accession codes listed in embodiment 26;

optionally wherein said sequence fragment comprises at most five, preferably at most four, more preferably at most three, even more preferably at most two, especially at most one amino acid substitutions.

Embodiment 29. The compound of any one of embodiments 1 to 28, wherein the entire sequence, optionally with the exception of an N-terminal and/or C-terminal cysteine, of peptide $P_a$ is identical to a sequence fragment of a protein and the entire sequence, optionally with the exception of an N-terminal and/or C-terminal cysteine, of peptide $P_b$ is identical to the same or another, preferably another, sequence fragment of the same protein, wherein the protein is identified by one of the UniProt accession codes listed in embodiment 26;

optionally wherein said sequence fragment and/or said another sequence fragment comprises at most five, preferably at most four, more preferably at most three, even more preferably at most two, especially at most one amino acid substitutions.

Embodiment 30. The compound of any one of embodiments 1 to 29, wherein the entire sequence, optionally with the exception of an N-terminal and/or C-terminal cysteine, of at least one occurrence of P, preferably of at least 10% of all occurrences of P, more preferably of at least 25% of all occurrences of P, yet more preferably of at least 50% of all occurrences of P, even more preferably of at least 75% of all occurrences of P, yet even more preferably of at least 90% of all occurrences of P or even of at least 95% of all occurrences of P, especially of all of the occurrences of P, is identical to a sequence fragment of an amino-acid sequence of Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab;
optionally wherein said sequence fragment comprises at most five, preferably at most four, more preferably at most three, even more preferably at most two, especially at most one amino acid substitutions.

Embodiment 31. The compound of any one of embodiments 1 to 30, wherein the entire sequence, optionally with the exception of an N-terminal and/or C-terminal cysteine, of peptide $P_a$ is identical to a sequence fragment of an amino-acid sequence of Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab;
optionally wherein said sequence fragment comprises at most five, preferably at most four, more preferably at most three, even more preferably at most two, especially at most one amino acid substitutions.

Embodiment 32. The compound of any one of embodiments 1 to 31, wherein the entire sequence, optionally with the exception of an N-terminal and/or C-terminal cysteine, of peptide $P_b$ is identical to a sequence fragment of an amino-acid sequence of Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab;

optionally wherein said sequence fragment comprises at most five, preferably at most four, more preferably at most three, even more preferably at most two, especially at most one amino acid substitutions.

Embodiment 33. The compound of any one of embodiments 1 to 32, wherein the entire sequence, optionally with the exception of an N-terminal and/or C-terminal cysteine, of peptide $P_a$ is identical to a sequence fragment of an amino-acid sequence and the entire sequence, optionally with the exception of an N-terminal and/or C-terminal cysteine, of peptide $P_b$ is identical to the same or another, preferably another, sequence fragment of the same amino-acid sequence, wherein the amino-acid sequence is an amino-acid sequence of Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab;

optionally wherein said sequence fragment and/or said another sequence fragment comprises at most five, preferably at most four, more preferably at most three, even more preferably at most two, especially at most one amino acid substitutions.

Embodiment 34. The compound of any one of embodiments 1 to 33, wherein each of the peptide n-mers is covalently bound to the biopolymer scaffold, preferably via a linker each.

Embodiment 35. The compound of any one of embodiments 1 to 34, wherein at least one of said linkers is selected from disulphide bridges and PEG molecules.

Embodiment 36. The compound of any one of embodiments 1 to 35, wherein at least one of the spacers S is selected from PEG molecules or glycans.

Embodiment 37. The compound of any one of embodiments 1 to 36, wherein at least one occurrence of P is $P_a$ and at least one occurrence of P is $P_b$,
wherein $P_a$ is a peptide with a sequence length of 5-13, preferably 7-13, amino acids,
wherein $P_b$ is a peptide with a sequence length of 5-13, preferably 7-13, amino acids,
wherein the entire sequence, optionally with the exception of an N-terminal and/or C-terminal cysteine, of peptide $P_a$ is identical to a sequence fragment of a protein, wherein the protein is identified by UniProt accession code P02708, O15146 or O75096, optionally wherein said sequence fragment comprises at most five, preferably at most four, more preferably at most three, even more preferably at most two, especially at most one amino acid substitutions,
wherein the entire sequence, optionally with the exception of an N-terminal and/or C-terminal cysteine, of peptide $P_b$ is identical to a sequence fragment of a protein, wherein the protein is identified by UniProt accession code P02708, O15146 or O75096, optionally wherein said sequence fragment comprises at most five, preferably at most four, more preferably at most three, even more preferably at most two, especially at most one amino acid substitutions.

Embodiment 38. The compound of any one of embodiments 14 to 37, wherein, in particular for $P_a$ and/or $P_b$, said sequence fragment of the protein is a fragment of the sequence consisting of amino acids 21-255 of the AChR subunit alpha sequence identified by UniProt accession code P02708 (optionally wherein the sequence fragment comprises at most five, preferably at most four, more preferably at most three, even more preferably at most two, especially at most one amino acid substitutions (e.g. such that a mimotope is formed)).

Embodiment 39. The compound of any one of embodiments 14 to 38, wherein, in particular for $P_a$ and/or $P_b$, said sequence fragment of the protein is a fragment of the sequence LKWNPDDYGGVKKIHIPSEK (SEQ ID NO: 1), preferably of the sequence WNPDDYGGVK (SEQ ID NO: 2) or VKKIHIPSEK (SEQ ID NO: 3).

Embodiment 40. The compound of any one of embodiments 6 to 39, wherein peptide $P_a$ and/or peptide $P_b$ consist of the sequence VKKIHIPSEKG (SEQ ID NO: 4) optionally with an N-terminal and/or C-terminal cysteine residue.

Embodiment 41. The compound of any one of embodiments 6 to 40, wherein the first peptide n-mer is $P_a$—S—$P_b$ and the second peptide n-mer is $P_a$—S—$P_b$.

Embodiment 42. The compound of any one of embodiments 6 to 40, wherein the peptide $P_a$ and the peptide $P_b$ comprise the same amino-acid sequence fragment, wherein the amino-acid sequence fragment has a length of at least 5 amino acids, even more preferably at least 6 amino acids, yet even more preferably at least 7 amino acids, especially at least 8 amino acids or even at least 9 amino acids.

Embodiment 43. The compound of any one of embodiments 1 to 36, wherein at least one occurrence of P is $P_a$ and at least one occurrence of P is $P_b$,
wherein $P_a$ is a peptide with a sequence length of 5-13, preferably 7-13, amino acids,
wherein $P_b$ is a peptide with a sequence length of 5-13, preferably 7-13, amino acids,
wherein the entire sequence, optionally with the exception of an N-terminal and/or C-terminal cysteine, of peptide $P_a$ is identical to a sequence fragment of a protein, wherein the protein is identified by UniProt accession code Q1HVF7, P03211, Q13585 or P30556, optionally wherein said sequence fragment comprises at most five, preferably at most four, more preferably at most three, even more preferably at most two, especially at most one amino acid substitutions,
wherein the entire sequence, optionally with the exception of an N-terminal and/or C-terminal cysteine, of peptide $P_b$ is identical to a sequence fragment of a protein, wherein the protein is identified by UniProt accession code Q1HVF7, P03211, Q13585 or P30556, optionally wherein said sequence fragment comprises at most five, preferably at most four, more preferably at most three, even more preferably at most two, especially at most one amino acid substitutions.

Embodiment 44. The compound of any one of embodiments 14 to 36 and 43, wherein, in particular for $P_a$ and/or $P_b$, said sequence fragment of the protein is a fragment of the sequence RPQKRPSCIGCKGTH (SEQ ID NO: 5) or RPQKRPSCIGCKGAH (SEQ ID NO: 6), preferably of the sequence KRPSCIGCK (SEQ ID NO: 7).

Embodiment 45. The compound of any one of embodiments 14 to 36 and 43 to 44, wherein, in particular for $P_a$ and/or $P_b$, said sequence fragment of the protein is a fragment of any one of the sequences MILNSSTEDGIKRIQDDCPKAGRHNYI (SEQ ID NO: 8), TAMEYRWPFGNYLCK (SEQ ID NO: 9), AIIHRNVFFIENTNITVCAFHYESQNSTLP (SEQ ID NO: 10), DVLIQLGIIRDCR (SEQ ID NO: 11), more preferably AFHYESQ (SEQ ID NO: 12).

Embodiment 46. The compound of any one of embodiments 6 to 36 and 43 to 45, wherein peptide $P_a$ and/or peptide $P_b$ consist of the sequence GRPQKRPSCIG (SEQ ID NO: 13) optionally with an N-terminal and/or C-terminal cysteine residue.

Embodiment 47. The compound of embodiments 6 to 36 and 43 to 46, wherein the first peptide n-mer is $P_a$—S—$P_b$ and the second peptide n-mer is $P_a$—S—$P_b$.

Embodiment 48. The compound of embodiments 6 to 36 and 43 to 47, wherein the peptide $P_a$ and the peptide $P_b$ comprise the same amino-acid sequence fragment, wherein the amino-acid sequence fragment has a length of at least 5 amino acids, even more preferably at least 6 amino acids, yet even more preferably at least 7 amino acids, especially at least 8 amino acids or even at least 9 amino acids.

Embodiment 49. A compound, preferably for the sequestration (or depletion) of anti human muscle nicotinic acetylcholine receptor (AChR) antibodies, anti human muscle-specific receptor tyrosine kinase antibodies and/or anti human low-density lipoprotein receptor related protein 4 antibodies present in a human individual, the compound comprising a biopolymer scaffold and at least two peptides with a sequence length of 7-13 amino acids, wherein each of the peptides independently comprises a 7-13 amino-acid sequence fragment of the AChR subunit alpha sequence identified by UniProt accession code P02708 (optionally wherein the sequence fragment comprises at most five, preferably at most four, more preferably at most three, even more preferably at most two, especially at most one amino acid substitutions (e.g. such that a mimotope is formed)) or of the muscle-specific receptor tyrosine kinase sequence identified by UniProt accession code O15146 (optionally wherein the sequence fragment comprises at most five, preferably at most four, more preferably at most three, even more preferably at most two, especially at most one amino acid substitutions (e.g. such that a mimotope is formed)) or of the low-density lipoprotein receptor related protein 4 sequence identified by UniProt accession code O75096 (optionally wherein the sequence fragment comprises at most five, preferably at most four, more preferably at most three, even more preferably at most two, especially at most one amino acid substitutions (e.g. such that a mimotope is formed)),
wherein the peptides are covalently bound to the biopolymer scaffold,
wherein the biopolymer scaffold is selected from the group consisting of human globulins and human albumin.

Embodiment 50. The compound of embodiment 49, wherein the at least two peptides comprise a peptide $P_1$ and a peptide $P_2$, wherein $P_1$ and $P_2$ comprise the same 7-13 amino-acid sequence fragment of AChR subunit alpha, wherein $P_1$ and $P_2$ are present in form of a peptide dimer $P_1$—S—$P_2$, wherein S is a non-peptide spacer, wherein the peptide dimer is covalently bound to the biopolymer scaffold, preferably via a linker.

Embodiment 51. The compound of 49 or 50, wherein said 7-13 amino-acid sequence fragment of AChR subunit alpha is a fragment of the sequence consisting of amino acids 21-255 of the AChR subunit alpha sequence identified by UniProt accession code P02708 (optionally wherein the sequence fragment comprises at most five, preferably at most four, more preferably at most three, even more preferably at most two, especially at most one amino acid substitutions (e.g. such that a mimotope is formed)).

Embodiment 52. The compound of any one of embodiments 49 to 51, wherein said 7-13 amino-acid sequence fragment of AChR subunit alpha is a fragment of the sequence LKWNPDDYGGVKKIHIPSEK (SEQ ID NO: 1), preferably of the sequence WNPDDYGGVK (SEQ ID NO: 2) or VKKIHIPSEK (SEQ ID NO: 3); optionally wherein the sequence fragment comprises at most five, preferably at most four, more preferably at most three, even more preferably at most two, especially at most one amino acid substitutions (e.g. such that a mimotope is formed).

Embodiment 53. The compound of any one of embodiments 49 to 52, wherein the peptides have a sequence length of 8-13 amino acids, preferably 9-12 amino acids, more preferably 10-12 amino acids, especially wherein the peptides consist of the sequence VKKI- HIPSEKG (SEQ ID NO: 4) optionally with an N-terminal and/or C-terminal cysteine residue.

Embodiment 54. The compound of any one of embodiments 1 to 53, wherein the compound further comprises at least one peptide with a sequence length of 7-13 amino acids, wherein the at least one peptide comprises a 7-13 amino-acid sequence fragment of the muscle-specific receptor tyrosine kinase sequence identified by UniProt accession code O15146 or of the low-density lipoprotein receptor related protein 4 sequence identified by UniProt accession code O75096, wherein the at least one peptide is covalently bound to the biopolymer scaffold, preferably via a linker.

Embodiment 55. A compound, preferably for the sequestration (or depletion) of anti-Epstein-Barr virus nuclear antigen 1 (EBNA-1) antibodies, anti human melatonin-related receptor (GPR50) antibodies and/or anti human type-1 angiotensin II receptor (AT1AR) antibodies present in a human individual, the compound comprising a biopolymer scaffold and at least two peptides with a sequence length of 7-13 amino acids,
wherein each of the peptides independently comprises a 7-13 amino-acid sequence fragment of the EBNA1 sequence identified by UniProt accession code Q1HVF7 or P03211 or of the GPR50 sequence identified by UniProt accession code Q13585 or of the type-1 angiotensin II receptor (AT1AR) sequence identified by UniProt accession code P30556, wherein the peptides are covalently bound to the biopolymer scaffold,
wherein the biopolymer scaffold is selected from the group consisting of human globulins, preferably from the group consisting of human immunoglobulins and human haptoglobin, and human albumin.

Embodiment 56. The compound of embodiment 55, wherein the at least two peptides comprise a peptide $P_1$ and a peptide $P_2$, wherein $P_1$ and $P_2$ comprise the same 7-13 amino-acid sequence fragment of said EBNA1 sequence or said GPR50 sequence, wherein $P_1$ and $P_2$ are present in form of a peptide dimer $P_1$—S—$P_2$, wherein S is a non-peptide spacer, wherein the peptide dimer is covalently bound to the biopolymer scaffold, preferably via a linker.

Embodiment 57. The compound of embodiment 55 or 56, wherein said 7-13 amino-acid sequence fragment is a fragment of the sequence RPQKRPSCIGCKGTH (SEQ ID NO: 5) or RPQKRPSCIGCKGAH (SEQ ID NO: 6), preferably of the sequence KRPSCIGCK (SEQ ID NO: 7); and/or wherein the peptides have a sequence length of 8-13 amino acids, preferably 9-12 amino acids, more preferably 10-12 amino acids, especially wherein at least one of the at least two, preferably each of the peptides consist of the sequence GRPQKRPSCIG (SEQ ID NO: 13) optionally with an N-terminal and/or C-terminal cysteine residue.

Embodiment 58. The compound of any one of embodiments 55 to 57, wherein said 7-13 amino-acid sequence fragment is a fragment of any one of the sequences MILNSSTEDGIKRIQDDCPKAGRHNYI (SEQ ID NO: 8), TAMEYRWPFGNYLCK (SEQ ID NO: 9), AIIHRNVFFIENTNITVCAFHYESQNSTLP (SEQ ID NO: 10), DVLIQLGIIRDCR (SEQ ID NO: 11), more preferably of the sequence AFHYESQ (SEQ ID NO: 12).

Embodiment 59. The compound of any one of embodiments 1 to 58, wherein the compound further comprises at least one peptide with a sequence length of 7-13 amino acids, wherein the at least one peptide comprises a 7-13 amino-acid sequence fragment of the type-1 angiotensin II receptor (AT1AR) sequence identified by UniProt accession code P30556, preferably of any one of the sequences MILNSSTEDGIKRIQDDCPKAGRHNYI (SEQ ID NO: 8), TAMEYRWPFGNYLCK (SEQ ID NO: 9), AIIHRNVFFIENTNITVCAFHYESQNSTLP (SEQ ID NO: 10), DVLIQLGIIRDCR (SEQ ID NO: 11), more preferably of the sequence AFHYESQ (SEQ ID NO: 12); wherein the at least one peptide is covalently bound to the biopolymer scaffold, preferably via a linker.

Embodiment 60. The compound of any one of embodiments 1 to 59, wherein each of the peptides is covalently bound to the scaffold via a linker.

Embodiment 61. The compound of any one embodiments 1 to 60, wherein the biopolymer scaffold is selected from human immunoglobulins and human haptoglobins.

Embodiment 62. The compound of embodiment any one of embodiments 1 to 61, wherein the biopolymer scaffold is human haptoglobin.

Embodiment 63. The compound of any one of embodiments 49 to 62, wherein at least one of the at least two peptides is circularized.

Embodiment 64. The compound of any one of embodiments 1 to 63, wherein the compound is non-immunogenic in humans.

Embodiment 65. A pharmaceutical composition comprising the compound of any one of embodiments 1 to 64 and at least one pharmaceutically acceptable excipient.

Embodiment 66. The pharmaceutical composition of embodiment 65, wherein the composition is prepared for intraperitoneal, subcutaneous, intramuscular and/or intravenous administration and/or wherein the composition is for repeated administration.

Embodiment 67. The pharmaceutical composition of any one of embodiments 1 to 66, wherein the molar ratio of peptide P to biopolymer scaffold in the composition is from 2:1 to 100:1, preferably from 3:1 to 90:1, more preferably from 4:1 to 80:1, even more preferably from 5:1 to 70:1, yet even more preferably from 6:1 to 60:1, especially from 7:1 to 50:1 or even from 8:10 to 40:1.

Embodiment 68. The pharmaceutical composition of any one of embodiments 6 to 67, wherein the molar ratio of peptide $P_a$ to biopolymer scaffold in the composition is from 2:1 to 100:1, preferably from 3:1 to 90:1, more preferably from 4:1 to 80:1, even more preferably from 5:1 to 70:1, yet even more preferably from 6:1 to 60:1, especially from 7:1 to 50:1 or even from 8:10 to 40:1.

Embodiment 69. The pharmaceutical composition of any one of embodiments 6 to 68, wherein the molar ratio of peptide $P_b$ to biopolymer scaffold in the composition is from 2:1 to 100:1, preferably from 3:1 to 90:1, more preferably from 4:1 to 80:1, even more preferably from 5:1 to 70:1, yet even more preferably from 6:1 to 60:1, especially from 7:1 to 50:1 or even from 8:10 to 40:1.

Embodiment 70. The pharmaceutical composition of any one of embodiments 65 to 69 for use in therapy.

Embodiment 71. The pharmaceutical composition for use according to embodiment 70, for use in prevention or treatment of an autoimmune disease in an individual having the autoimmune disease or being at risk of developing the autoimmune disease.

Embodiment 72. The pharmaceutical composition for use according to embodiment 71, wherein the autoimmune disease is selected from the group consisting of neuromyelitis optica, seropositive neuromyelitis optica spectrum disorders, autoimmune-encephalitis, multiple sclerosis, amyotrophic lateral sclerosis, systemic lupus erythematosus dementia, myasthenia gravis, in particular transient neonatal myasthenia gravis, dilatative Cardiomyopathy, pulmonary hypertension, Sjögren's Syndrome, celiac Disease, Graves Disease, Goodpasture Disease, preeclampsia, Behcet's Disease, systemic sclerosis, hypertension, type I diabetes, type II diabetes, systemic lupus erythematosus, anti N-methyl-D-aspartate receptor (NMDAR) encephalitis, antiphospholipid syndrome, membranous nephropathy, primary biliary cholangitis, amyotrophic lateral sclerosis, Chagas disease cardiomyopathy, immune thrombocytopenic purpura, pemphigus vulgaris, bullous pemphigoid, epidermolysis bullosa acquisita and bullous systemic lupus erythematosus.

Embodiment 73. The pharmaceutical composition for use according to embodiment 70, for use in prevention or treatment of transplant rejection in an individual having a transplant or eligible for a transplantation.

Embodiment 74. The pharmaceutical composition for use according to embodiment 70, for use in prevention or treatment of adverse reactions based on anti-drug antibodies or anti-gene-delivery vector antibodies, such as anti-AAV antibodies, in an individual undergoing therapy with the drug or eligible for therapy with the drug, or in an individual undergoing gene therapy or eligible for gene therapy,
preferably wherein the drug is a peptide or protein, especially selected from the group of enzymes, enzyme inhibitors, antibodies, antibody fragments, antibody mimetics, antibody-drug conjugates, hormones, growth factors, clotting factors and cytokines, preferably wherein the entire sequence, optionally with the exception of an N-terminal and/or C-terminal cysteine, of at least one occurrence of peptide P, or of peptide $P_a$ and/or of peptide $P_b$ is identical to a sequence fragment of an amino-acid sequence of the peptide or protein, optionally wherein said sequence fragment comprises at most five, preferably at most four, more preferably at most three, even more preferably at most two, especially at most one amino acid substitutions.

Embodiment 75. The pharmaceutical composition for use according to embodiment 74, wherein the drug is Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab,
preferably wherein the entire sequence, optionally with the exception of an N-terminal and/or C-terminal cysteine, of at least one occurrence of peptide P, or of peptide $P_a$ and/or of peptide $P_b$ is identical to a sequence fragment of an amino-acid sequence of the drug, optionally wherein said sequence fragment comprises at most five, preferably at most four, more preferably at most three, even more preferably at most two, especially at most one amino acid substitutions.

Embodiment 76. The pharmaceutical composition for use according to any one of embodiments 70 to 75, wherein one or more antibodies are present in the individual which are specific for at least one occurrence of peptide P, or for peptide $P_a$ and/or peptide $P_b$, preferably wherein said antibodies are related to said disease.

Embodiment 77. The pharmaceutical composition for use according to any one of embodiments 70 to 76, wherein the composition is non-immunogenic in the individual.

Embodiment 78. The pharmaceutical composition for use according to any one of embodiments 70 to 77, wherein the composition is administered at a dose of 1-1000 mg, preferably 2-500 mg, more preferably 3-250 mg, even more preferably 4-100 mg, especially 5-50 mg, compound per kg body weight of the individual.

Embodiment 79. The pharmaceutical composition for use according to any one of embodiments 70 to 78, wherein the composition is administered intraperitoneally, subcutaneously, intramuscularly or intravenously.

Embodiment 80. A method of sequestering (or depleting) one or more antibodies present in an individual, comprising
obtaining a pharmaceutical composition as defined in any one of embodiments 65 to 69, wherein the composition is non-immunogenic in the individual and wherein the one or more antibodies present in the individual are specific for at least one occurrence of P, or for peptide $P_a$ and/or peptide $P_b$; and
administering the pharmaceutical composition to the individual.

Embodiment 81. The method of embodiment 80, wherein the individual is a non-human animal, preferably a non-human primate, a sheep, a pig, a dog or a rodent, in particular a mouse.

Embodiment 82. The method of embodiments 80 or 81, wherein the biopolymer scaffold is autologous with respect to the individual, preferably wherein the biopolymer scaffold is an autologous protein.

Embodiment 83. The method of any one of embodiments 80 to 82, wherein the individual is administered a heterologous protein, preferably a heterologous antibody such as a nanobody, and wherein the one or more antibodies present in the individual are specific for said heterologous protein, preferably wherein said administering of the heterologous protein is prior to, concurrent with and/or subsequent to said administering of the pharmaceutical composition.

Embodiment 84. The method of any one of embodiments 80 to 83, wherein the individual is a non-human animal and the heterologous protein is human or humanized.

Embodiment 85. The method of any one of embodiments 80 to 82, wherein the individual is administered a drug and wherein the one or more antibodies present in the individual are specific for said drug, preferably wherein said administering of the drug is prior to, concurrent with and/or subsequent to said administering of the pharmaceutical composition.

Embodiment 86. The method of embodiment 85, wherein the drug is Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab.

Embodiment 87. The method of any one of embodiments 80 to 86, wherein the individual is healthy.

Embodiment 88. The method of any one of embodiments 80 to 87, wherein the composition is administered intraperitoneally, subcutaneously, intramuscularly or intravenously.

Embodiment 89. A pharmaceutical composition, comprising the compound of any one of embodiments 1 to 64 and further comprising an active agent such as a protein or a peptide and optionally at least one pharmaceutically acceptable excipient,
wherein the active agent comprises a peptide fragment with a sequence length of 2-13 amino acids, preferably 3-11 amino acids, more preferably 4-9 amino acids, especially 5-8 amino acids, and
wherein the sequence of at least one occurrence of peptide P, or peptide $P_a$ and/or peptide $P_b$, of the compound is at least 70% identical, preferably at least 75% identical, more preferably at least 80% identical, yet more preferably at least 85% identical, even more preferably at least 90% identical, yet even more preferably at least 95% identical, especially completely identical to the sequence of said peptide fragment.

Embodiment 90. The pharmaceutical composition of embodiment 89, wherein the active agent is an enzyme, preferably a human enzyme, an antibody, preferably a human or humanized antibody, a hormone, a growth factor, a clotting factor, a cytokine or a gene delivery vector, such as AAV.

Embodiment 91. The pharmaceutical composition of embodiment 89 or 90, wherein the active agent is Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab.

Embodiment 92. The pharmaceutical composition of any one of embodiments 89 to 91, wherein the composition is prepared for intravenous administration.

Embodiment 93. The pharmaceutical composition of any one of embodiments 89 to 92, wherein the composition is an aqueous solution.

Embodiment 94. The pharmaceutical composition of any one of embodiments 89 to 93 for use in inhibition of an immune reaction, preferably an antibody-mediated immune reaction, against the active agent.

Embodiment 95. The pharmaceutical composition for use according to embodiment 94, wherein the composition is non-immunogenic in the individual.

Embodiment 96. A method of inhibiting an immune reaction to a treatment with an active agent in an individual in need of treatment with the active agent, comprising obtaining a pharmaceutical composition as defined in any one of embodiments 89 to 95; wherein the compound of the pharmaceutical composition is non-immunogenic in the individual, and administering the pharmaceutical composition to the individual.

Embodiment 97. The method of embodiment 96, wherein the individual is human.

Embodiment 98. The method of embodiment 96 or 97, wherein the biopolymer scaffold is autologous with respect to the individual, preferably wherein the biopolymer scaffold is an autologous protein.

Embodiment 99. The method of any one of embodiments 96 to 98, wherein the composition is administered intraperitoneally, subcutaneously, intramuscularly or intravenously.

Embodiment 100. A method of providing a compound according to any one of embodiments 1 to 64, comprising the steps of identifying at least one individual having an undesired antibody against an antigen, screening a peptide library to identify a peptide mimotope for which the undesired antibody is specific, and providing the compound, wherein at least one occurrence of P of the compound comprises the entire sequence of the peptide mimotope.

Embodiment 101. The method of embodiment 100, wherein the antigen is a peptide or protein, wherein the sequence of the peptide or protein does not comprise the entire sequence of the peptide mimotope.

Embodiment 102. The method of embodiment 100 or 101, wherein at least 10% of all occurrences of P comprise the entire sequence of the peptide mimotope, more preferably wherein at least 25% of all occurrences of P comprise the entire sequence of the peptide mimotope, yet more preferably wherein at least 50% of all occurrences of P comprise the entire sequence of the peptide mimotope, even more preferably wherein at least 75% of all occurrences of P comprise the entire sequence of the peptide mimotope, yet even more preferably wherein at least 90% of all occurrences of P comprise the entire sequence of the peptide mimotope or even wherein at least 95% of all occurrences of P comprise the entire sequence of the peptide mimotope, especially wherein all of the occurrences of P comprise the entire sequence of the peptide mimotope.

Embodiment 103. The method of any one of embodiments 100 to 102, wherein the peptide library comprises circular peptides.

Embodiment 104. The method of any one of embodiments 100 to 103, wherein the peptide library is a phage display library, a peptide microarray library or a soluble peptide library.

Embodiment 105. The method of any one of embodiments 100 to 104, wherein the screening of the peptide library is performed with a serum obtained from the at least one individual, wherein the serum comprises the undesired antibody.

Embodiment 106. The method of any one of embodiments 100 to 105, wherein the compound is non-immunogenic in the at least one individual.

Embodiment 107. The method of any one of embodiments 100 to 106, wherein the at least one individual is a non-human animal, preferably a non-human primate, a sheep, a pig, a dog or a rodent, in particular a mouse.

Embodiment 108. The method of any one of embodiments 100 to 106, wherein the at least one individual is human.

Embodiment 109. The method of any one of embodiments 100 to 108, wherein the biopolymer scaffold is autologous with respect to the at least one individual, preferably wherein the biopolymer scaffold is an autologous protein.

Embodiment 110. The method of any one of embodiments 100 to 109, wherein the at least one individual has been administered a heterologous protein, preferably a heterologous antibody such as a nanobody, and wherein the antigen is said heterologous protein.

Embodiment 111. The method of any one of embodiments 100 to 110, wherein the at least one individual is a non-human animal and the heterologous protein is human or humanized.

Embodiment 112. The method of any one of embodiments 100 to 111, wherein the individual has been administered a drug and wherein the drug is the antigen.

Embodiment 113. The method of embodiment 112, wherein the drug is an enzyme, preferably a human enzyme, an antibody, preferably a human or humanized antibody, a hormone, a growth factor, a clotting factor, a cytokine or a gene delivery vector, such as AAV.

Embodiment 114. The method of embodiment 112, wherein the drug is Alpha-1-proteinase inhibitor, Alglucerase, Taliglucerase alfa, Pegademase, Agalsidase beta, Alglucosidase alfa, Laronidase, Idursulfase, Elosulfase alfa, Galsulfase, Sebelipase alfa, Cerliponase alfa, Sebelipase alfa, Asfotase Alfa, Elapegademase, Olipudase alpha, Velmanase alpha, N(4)-(beta-N-acetylglucosaminyl)-L-asparaginase, Rasburicase, Pegloticase, Human Antithrombin III, Plasma protease C1 inhibitor, Turoctocog alfa, Drotrecogin alfa, Emicizumab, Coagulation factor VIIa Recombinant Human, Antihemophilic factor human recombinant, Von Willebrand Factor Human, Susoctocog alfa, Antihemophilic factor human recombinant, Antihemophilic factor, human recombinant, Oprelvekin, Aldesleukin, Rilonacept, Anakinra, Denileukin diftitox, Erythropoietin, Interferon beta-la, Interferon alfa, interferon alfa-2b, interferon alfacon-1, interferon gamma-1b, interferon alfa-2b recombinant, growth hormone (UniProt P01241), insulin (UniProt P01308), IGF1 (UniProt P05019), PTH (UniProt P01270), Thyrotropin alfa, Choriogonadotropin alfa, Follitropin, Lutropin alfa, Somatotropin, Albiglutide, Metreleptin, Corifollitropin alfa, Filgrastim, FGF2 (UniProt P09038), NGF (UniProt P01138), GDNF (UniProt P39905), BDNF (UniProt P23560), Mecasermin, Palifermin, GCSF (UniProt P09919), IGF2 (UniProt P01344), Becaplermin, Palifermin, Tasonermin, Aflibercept, Rilonacept, Romiplostim, Tagraxofusp, Efmoroctocog alfa, Eftrenonacog alfa, Rilonacept, Belatacept, Atacicept, Albutrepenonacog alfa, Dulaglutide, Etanercept, Asfotase Alfa, Natalizumab, Rituximab, Adalimumab, Ipilimumab, Trastuzumab, Bevacizumab, Evolocumab, Ixekizumab, Omalizumab, Teprotumumab, Idarucizumab, Cetuximab, Oportuzumab monatox, Ibritumomab tiuxetan, Abciximab, Rituximab, Ofatumumab, Erenumab, Emicizumab or Atezolizumab.

Embodiment 115. The method of any one of embodiments 100 to 114, wherein the individual is healthy.

Embodiment 116. The method of any one of embodiments 100 to 115, wherein the undesired antibody is an autoantibody of the at least one individual.

The present invention is further illustrated by the following figures and examples, without being restricted thereto.

In the context of the following figures and examples the compound of the present invention is also referred to as "Selective Antibody Depletion Compound" (SADC).

Figure 1:
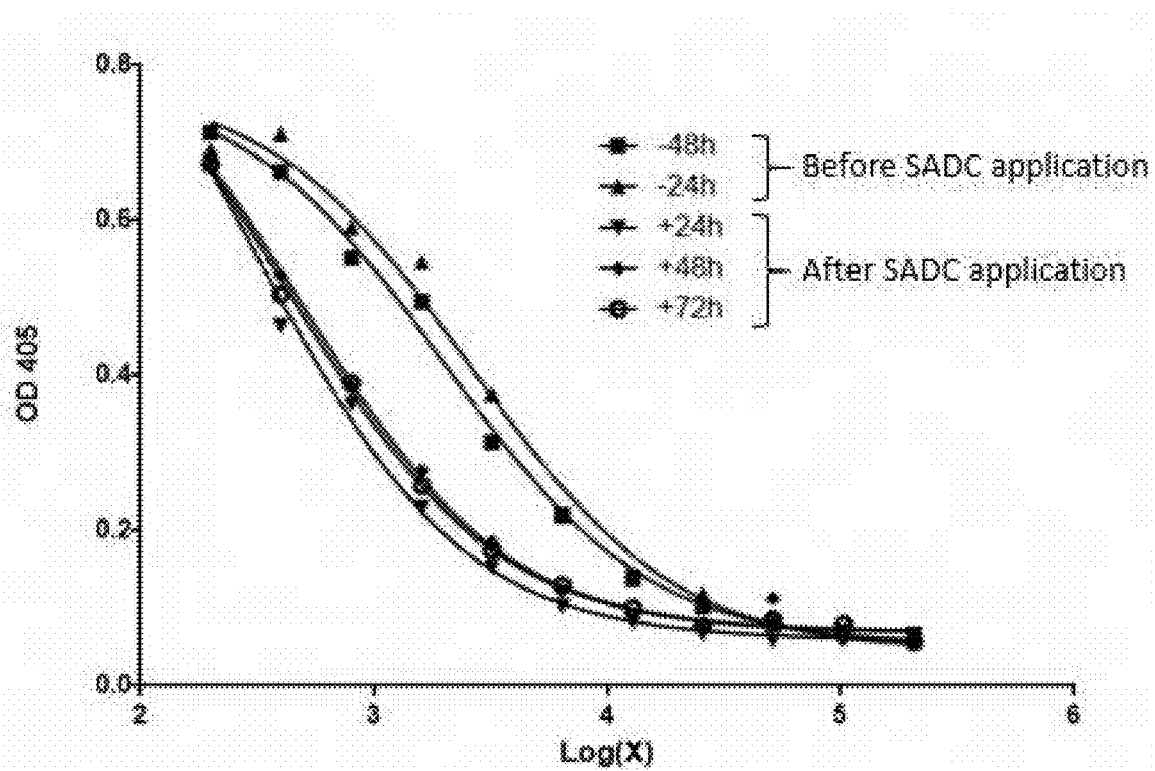
FIG. 1: The compound of the present invention successfully reduces the titre of undesired antibodies. Each compound of the invention was applied at time point 0 by i.p. injection into Balb/c mice pre-immunized by peptide immunization against a defined antigen. Each top panel shows anti-peptide titers (0.5× dilution steps; X-axis shows log(X) dilutions) against OD values (y-axis) according to a standard ELISA detecting the corresponding antibody. Each bottom panel shows titers Log IC50 (y-axis) before injection of each compound of the invention (i.e. titers at −48 h and −24 h) and after application of each compound of the invention (i.e. titers+24 h, +48 h and +72 h after injection; indicated on the x-axis). (A) Compound with albumin as the biopolymer scaffold that binds to antibodies directed against EBNA1 (associated with pre-eclampsia). The mice were pre-immunized with a peptide vaccine carrying the EBNA-1 model epitope. (B) Compound with albumin as the biopolymer scaffold that binds to antibodies directed against a peptide derived from the human AChR protein MIR (associated with myasthenia gravis). The mice were pre-immunized with a peptide vaccine carrying the AChR MIR model epitope. (C) Compound with immunoglobulin as the biopolymer scaffold that binds to antibodies directed against EBNA1 (associated with pre-eclampsia). The mice were pre-immunized with a peptide vaccine carrying the EBNA-1 model epitope. (D) Compound with haptoglobin as the biopolymer scaffold that binds to antibodies directed against EBNA1 (associated with pre-eclampsia). The mice were pre-immunized with a peptide vaccine carrying the EBNA-1 model epitope. (E) Demonstration of selectivity using the same immunoglobulin-based compound of the invention binding to antibodies directed against EBNA1 that was used in the experiment shown in panel C. The mice were pre-immunized with an unrelated amino acid sequence. No titre reduction occurred, demonstrating selectivity of the compound.
Figure 1:
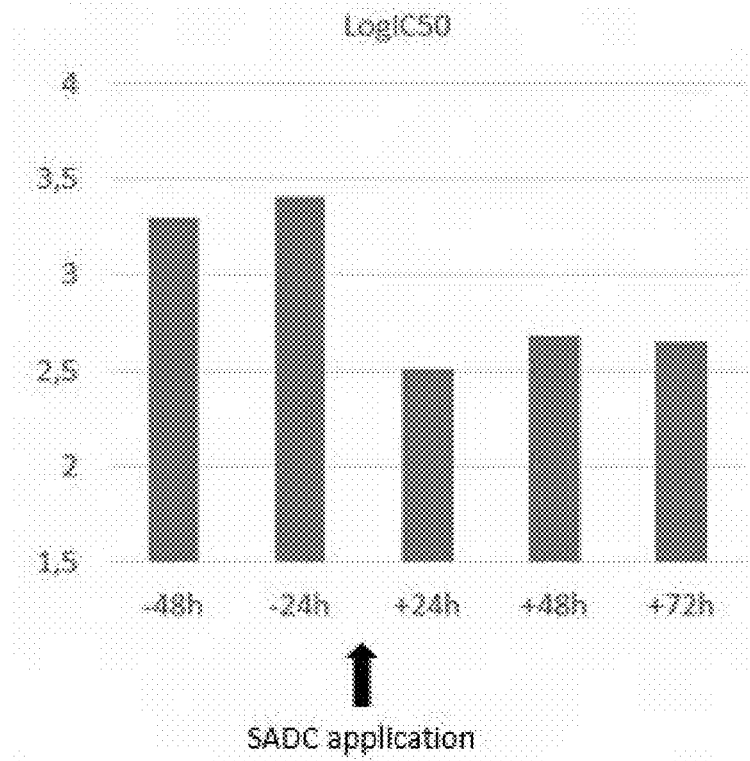

FIG. 4: Rapid, selective antibody depletion in mice using various SADC biopolymer scaffolds. Treated groups exhibited rapid and pronounced antibody reduction already at 24 hrs (in particular SADC-TF) when compared to the mock treated control group SADC-CTL (containing an unrelated peptide). SADC with albumin scaffold—SADC-ALB, SADC with immunoglobulin scaffold—SADC-IG, SADC with haptoglobin scaffold-SADC-HP, and SADC with transferrin scaffold-SADC-TF.

FIG. 5: Detection of SADCs in plasma via their peptide moieties 24 hrs after SADC injection. Both haptoglobin-scaffold-based SADCs (SADC-HP and SADC-CTL) exhibited a relatively shorter plasma half life which represents an advantage over SADCs with other biopolymer scaffolds such as SADC-ALB, SADC-IG oder SADC-TF. SADC with albumin scaffold-SADC-ALB, SADC with immunoglobulin scaffold-SADC-IG, SADC with haptoglobin scaffold-SADC-HP, and SADC with transferrin scaffold-SADC-TF.

FIG. 6: Detection of SADC-IgG complexes in plasma 24 hrs after SADC injection. Haptoglobin based SADCs were subject to accelerated clearance when compared to SADCs with other biopolymer scaffolds. SADC with albumin scaffold-SADC-ALB, SADC with immunoglobulin scaffold-SADC-IG, SADC with haptoglobin scaffold—SADC-HP, and SADC with transferrin scaffold—SADC-TF.

FIG. 7: In vitro analysis of SADC-IgG complex formation. Animals SADC-TF and -ALB showed pronounced immunocomplex formation and binding to Clq as reflected by the strong signals and by sharp signal lowering in case 1000 ng/ml SADC-TF due to the transition from antigen-antibody equilibrium to antigen excess. In contrast, in vitro immunocomplex formation with SADC-HP or SADC-IG were much less efficient when measured in the present assay. These findings corroborate the finding that haptoglobin scaffolds are advantageous over other SADC biopolymer scaffolds because of the reduced propensity to activate the complement system. SADC with albumin scaffold—SADC-ALB, SADC with immunoglobulin scaffold—SADC-IG, SADC with haptoglobin scaffold—SADC-HP, and SADC with transferrin scaffold—SADC-TF.

FIG. 8: Determination of IgG capturing by SADCs in vitro. SADC-HP showed markedly less antibody binding capacity in vitro when compared to SADC-TF or SADC-ALB. SADC with albumin scaffold—SADC-ALB, SADC with immunoglobulin scaffold—SADC-IG, SADC with haptoglobin scaffold—SADC-HP, and SADC with transferrin scaffold—SADC-TF.

EXAMPLES

Example 1: The Compound of the Present Invention Effectively Reduces the Titre of Undesired Antibodies Animal models: In order to provide in vivo models with measurable titers of prototypic undesired antibodies in human indications, BALB/c mice were immunized using standard experimental vaccination with KLH-conjugated peptide vaccines derived from established human autoantigens or anti-drug antibodies. After titer evaluation by standard peptide ELISA, immunized animals were treated with the corresponding test SADCs to demonstrate selective antibody lowering by SADC treatment. All experiments were performed in compliance with the guidelines by the corresponding animal ethics authorities.

Immunization of mice with model antigens: Female BALB/c mice (aged 8-10 weeks) were supplied by Janvier (France), maintained under a 12 h light/12 h dark cycle and given free access to food and water. Immunizations were performed by s.c. application of KLH carrier-conjugated peptide vaccines injected 3 times in biweekly intervals. KLH conjugates were generated with peptide T3-2 (SEQ ID NO. 14: CGRPQKRPSCIGCKG), which represents an example for molecular mimicry between a viral antigen (EBNA-1) and an endogenous human receptor antigen, namely the placental GPR50 protein, that was shown to be relevant to preeclampsia (Elliott et al.). In order to confirm the generality of this approach, a larger antigenic peptide derived from the autoimmune condition myasthenia gravis was used for immunization of mice with a human autoepitope. In analogy to peptide T3-2, animals were immunized with peptide T1-1 (SEQ ID NO. 15: LKWNPD-DYGGVKKIHIPSEKGC), derived from the MIR (main immunogenic region) of the human AChR protein which plays a fundamental role in pathogenesis of the disease (Luo et al.). The T1-1 peptide was used for immunizing mice with a surrogate partial model epitope of the human AChR autoantigen. The peptide T8-1 (SEQ ID NO. 16: DHT-LYTPYHTHPG) was used to immunize control mice to provide a control titer for proof of selectivity of the system. For vaccine conjugate preparation, KLH carrier (Sigma) was activated with sulfo-GMBS (Cat. Nr. 22324 Thermo), according to the manufacturer's instructions, followed by addition of either N- or C-terminally cysteinylated peptides T3-2 and T1-1 and final addition of Alhydrogel® before injection into the flank of the animals. The doses for vaccines T3-2 and T1-1 were 15 µg of conjugate in a volume of 100 ul per injection containing Alhydrogel® (InvivoGen VAC-Alu-250) at a final concentration of 1% per dose.

Generation of prototypic SADCs: For testing selective antibody lowering activity by SADCs of T3-2 and T1-1 immunized mice, SADCs were prepared with mouse serum albumin (MSA) or mouse immunoglobulin (mouse-Ig) as biopolymer scaffold in order to provide an autologous biopolymer scaffold, that will not induce any immune reaction in mice, or non-autologuous human haptoglobin as biopolymer scaffold (that did not induce an allogenic reaction after one-time injection within 72 hours). N-terminally cysteinylated SADC peptide E049 (SEQ ID NO. 13: GRPQKRPSCIG) and/or C-terminally cysteinylated SADC peptide E006 (SEQ ID NO. 4: VKKIHIPSEKG) were linked to the scaffold using sulfo-GMBS (Cat. Nr. 22324 Thermo)-activated MSA (Sigma; Cat. Nr. A3559) or -mouse-Ig (Sigma, 15381) or -human haptoglobin (Sigma H0138) according to the instructions of the manufacturer, thereby providing MSA-, Ig- and haptoglobin-based SADCs with the corresponding cysteinylated peptides, that were covalently attached to the lysines of the corresponding biopolymer scaffold. Beside conjugation of the cysteinylated peptides to the lysines via a bifunctional amine-to-sulfhydryl crosslinker, a portion of the added cysteinylated SADC peptides directly reacted with sulfhydryl groups of cysteines of the albumin scaffold protein, which can be detected by treating the conjugates with DTT followed by subsequent detection of free peptides using mass spectrometry or any other analytical method that detects free peptide. Finally, these SADC conjugates were dialysed against water using Pur-A-Lyzer™ (Sigma) and subsequently lyophilized. The lyophilized material was resuspended in PBS before injection into animals.

In vivo functional testing of SADCs: Prototypic SADCs, SADC-E049 and SADC-E006 were injected intraperitoneally (i.p.; as a surrogate for an intended intravenous application in humans and larger animals) into the mice that had previously been immunized with peptide vaccine T3-2 (carrying the EBNA-1 model epitope) and peptide vaccine T1-1 (carrying the AChR MIR model epitope). The applied dose was 30 µg SADC conjugate in a volume of 50 µl PBS. Blood takes were performed by submandibular vein puncture, before (−48 h, −24 h) and after (+24 h, +48 h, +72 h, etc.) i.p. SADC injections, respectively, using capillary microhematocrit tubes. Using ELISA analysis (see below), it was found that both prototypic SADCs were able to clearly reduce the titers over a period of at least 72 hrs in the present animal model. It could therefore be concluded that SADCs can be used to effectively reduce titers in vivo.

Titer analysis: Peptide ELISAs were performed according to standard procedures using 96-well plates (Nunc Medisorp plates; Thermofisher, Cat Nr 467320) coated for 1 h at RT with BSA-coupled peptides (30 nM, dissolved in PBS) and incubated with the appropriate buffers while shaking (blocking buffer, 1% BSA, 1x PBS; washing buffer, 1×PBS/0.1% Tween; dilution buffer, 1×PBS/0.1% BSA/0.1% Tween). After serum incubation (dilutions starting at 1:50 in PBS; typically in 1:3 or 1:2 titration steps), bound antibodies were detected using Horseradish Peroxidase-conjugated goat anti-mouse IgG (Fc) from Jackson immunoresearch (115-035-008). After stopping the reaction, plates were measured at 450 nm for 20 min using TMB. EC50 were calculated from readout values using curve fitting with a 4-parameter logistic regression model (GraphPad Prism) according to the procedures recommended by the manufacturer. Constraining parameters for ceiling and floor values were set accordingly, providing curve fitting quality levels of $R^2>0.98$.

FIG. 1A shows an in vivo proof of concept in a mouse model for in vivo selective plasma-lowering activity of a prototypic albumin-based SADC candidate that binds to antibodies directed against EBNA1, as a model for autoantibodies and mimicry in preeclampsia (Elliott et al.). For these mouse experiments, mouse albumin was used, in order to avoid any reactivity against a protein from a foreign species. Antibody titers were induced in 6 months old Balb/c mice by standard peptide vaccination. The bottom panel demonstrates that titers Log IC50 (y-axis) before SADC injection (i.e. titers at −48 h and −24 h) were higher than titers Log IC50 after SADC application (i.e. titers+24 h, +48 h and +72 h after injection; indicated on the x-axis).

A similar example is shown in FIG. 1B, using an alternative example of a peptidic antibody binding moiety for a different disease indication. Antibody lowering activity of an albumin-based SADC in a mouse model that was pre-immunized with a different peptide derived from the human AChR protein MIR region (Luo et al.) in order to mimic the situation in myasthenia gravis. The induced antibody titers against the AChR-MIR region were used as surrogate for anti-AChR-MIR autoantibodies known to play a causative role in myasthenia gravis (reviewed by Vincent et al.). A clear titer reduction was seen after SADC application.

FIGS. 1C and 1D demonstrate the functionality of SADC variants comprising alternative biopolymer scaffolds. Specifically, FIG. 1C shows that an immunoglobulin scaffold can be successfully used whereas FIG. 1D demonstrates the use of a haptoglobin-scaffold for constructing an SADC. Both examples show an in vivo proof of concept for selective antibody lowering by an SADC, carrying covalently bound example peptide E049.

The haptoglobin-based SADC was generated using human Haptoglobin as a surrogate although the autologuous scaffold protein would be preferred. In order to avoid formation of anti-human-haptoglobin antibodies, only one single SADC injection per mouse of the non-autologuous scaffold haptoglobin was used for the present experimental conditions. As expected, under the present experimental conditions (i.e. one-time application), no antibody reactivity was observed against the present surrogate haptoglobin homologue.

FIG. 1E demonstrates the selectivity of the SADC system. The immunoglobulin-based SADC carrying the peptide E049 (i.e. the same as in FIG. 1C) cannot reduce the Ig-titer that was induced by a peptide vaccine with an unrelated, irrelevant aminoacid sequence, designated peptide T8-1 (SEQ ID NO. 16: DHTLYTPYHTHPG). The example shows an in vivo proof of concept for the selectivity of the system. The top panel shows anti-peptide T8-1 titers (0.5× dilution steps starting from 1:50 to 1:102400; X-axis shows log(X) dilutions) against OD values (y-axis) according to a standard ELISA. T8-1-titers are unaffected by administration of SADC-Ig-E049 after application. The bottom panel demonstrates that the initial titers Log IC50 (y-axis) before SADC injection (i.e. titers at −48 h and −24 h) are unaffected by administration of SADC-Ig-E049 (arrow) when compared to the titers Log IC50 after SADC application (i.e. titers+24 h, +48 h and +72 h; as indicated on the x-axis), thereby demonstrating the selectivity of the system.

Example 2: Immunogenicity of SADCs

In order to exclude immunogenicity of SADCs, prototypic candidate SADCs were tested for their propensity to induce antibodies upon repeated injection. Peptides T3-1 and T9-1 were used for this test. T3-1 is a 10-amino acid peptide derived from a reference epitope of the Angiotensin receptor, against which agonistic autoantibodies are formed in a pre-eclampsia animal model (Zhou et al.); T9-1 is a 12-amino acid peptide derived from a reference anti-drug antibody epitope of human IFN gamma (Lin et al.). These control SADC conjugates were injected 8× every two weeks i.p. into naïve, non-immunized female BALB/c mice starting at an age of 8-10 weeks.

Figure 2:
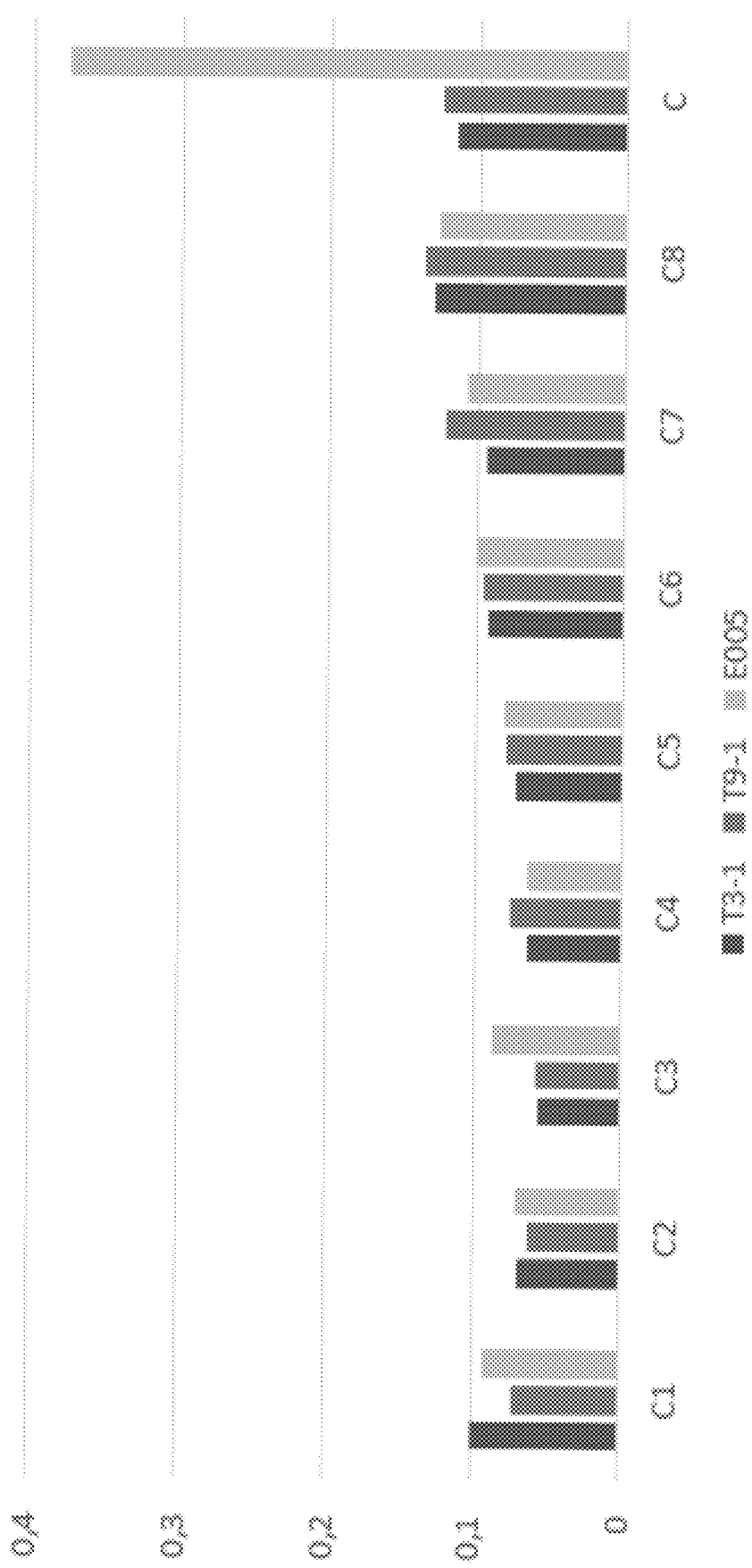
FIG. 2: The compound of the invention is non-immunogenic and does not induce antibody formation after repeated injection into mice. Animals C1-C4 as well as animals C5-C8 were treated i.p. with two different compounds of the invention. Control animal C was vaccinated with a KLH-peptide derived from the human AChR protein MIR. Using BSA-conjugated peptide probes T3-1, T9-1 and E005 (grey bars, as indicated in the graph), respectively, for antibody titer detection by standard ELISA at a dilution of 1:100, it could be demonstrated that antibody induction was absent in animals treated with a compound of the invention, when compared to the vaccine-treated control animal C (y-axis, OD450 nm).

Animals C1-C4 were treated i.p. (as described in example 1) with SADC T3-1. Animals C5-C8 were treated i.p. with an SADC carrying the peptide T9-1. As a reference signal for ELISA analysis, plasma from a control animal that was vaccinated 3 times with KLH-peptide T1-1 (derived from the AChR-MIR, explained in Example 1) was used. Using BSA-conjugated peptide probes T3-1, T9-1 and E005 (SEQ ID NO: 17: GGVKKIHIPSEK), respectively, for antibody titer detection by standard ELISA at a dilution of 1:100, it could be demonstrated that antibody induction was absent in SADC-treated animals, when compared to the vaccine-treated control animal C (see FIG. 2). The plasmas were obtained by submandibular blood collection, 1 week after the 3rd vaccine injection (control animal C) and after the last of 8 consecutive SADC injections in 2-weeks intervals (animals C1-C8), respectively. Thus it was demonstrated that SADCs are non-immunogenic and do not induce antibody formation after repeated injection into mice.

Example 3: Successful In Vitro Depletion of Antibodies Using SADCs Carrying Multiple Copies of Monovalent or Divalent Peptides Plasma of E006-KLH (VKKIHIPSEKG (SEQ ID NO: 4) with C-terminal cysteine, conjugated to KLH) vaccinated mice was diluted 1:3200 in dilution buffer (PBS+0.1% w/v BSA+0.1% Tween20) and incubated (100 µl, room temperature) sequentially (10 min/well) four times on single wells of a microtiter plate that was coated with 2.5 µg/ml (250 ng/well) of SADC or 5 µg/ml (500 ng/well) albumin as negative control.

In order to determine the amount of free, unbound antibody present before and after incubation on SADC coated wells, 50 µl of the diluted serum were taken before and after the depletion and quantified by standard ELISA using E006-BSA coated plates (10 nM peptide) and detection by goat anti mouse IgG bio (Southern Biotech, diluted 1:2000). Subsequently, the biotinylated antibody was detected with Streptavidin-HRP (Thermo Scientific, diluted 1:5000) using TMB as substrate. Development of the signal was stopped with 0.5 M sulfuric acid.

Figure 3:
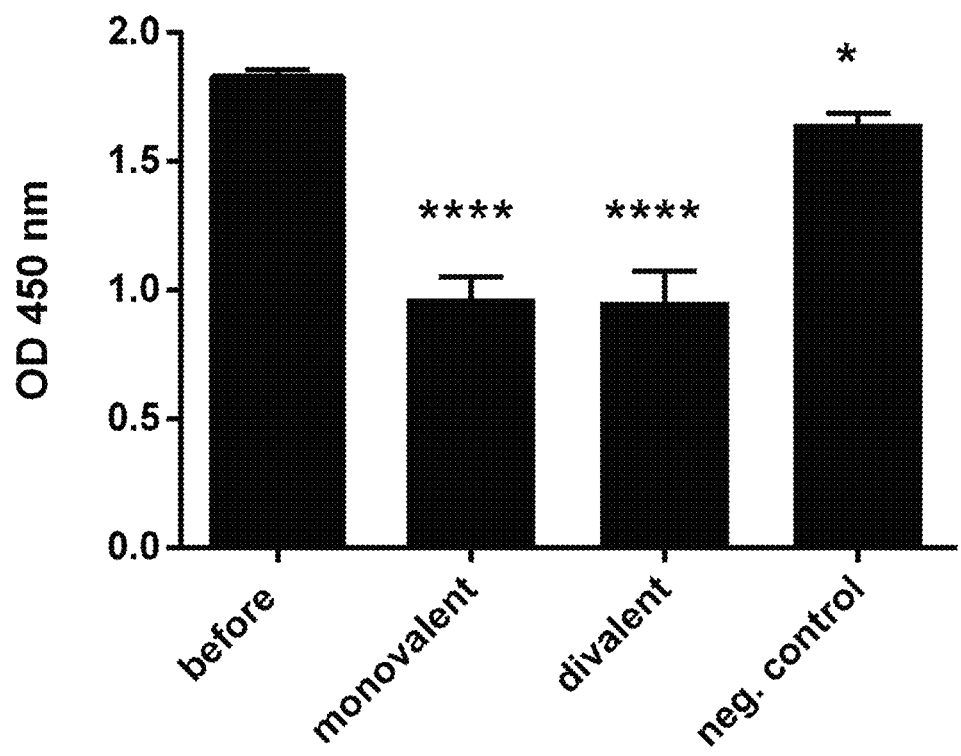
FIG. 3: Successful in vitro depletion of antibodies using SADCs carrying multiple copies of monovalent or divalent peptides. SADCs with mono- or divalent peptides were very suitable to adsorb antibodies and thereby deplete them. "Monovalent" means that peptide monomers are bound to the biopolymer scaffold (i.e. n=1) whereas "divalent" means that peptide dimers are bound to the biopolymer scaffold (i.e. n=2). In the present case, the divalent peptides were "homo-divalent", i.e. the peptide n-mer of the SADC is E006—spacer—E006).

ELISA was measured at OD450 nm (y-axis). As a result, the antibody was efficiently adsorbed by either coated mono- or divalent SADCs containing peptide E006 with C-terminal cysteine (sequence VKKIHIPSEKGC, SEQ ID NO: 4) (before=non-depleted starting material; mono-divalent corresponds to peptides displayed on the SADC surface; neg. control was albumin; indicated on the x-axis). See FIG. 3. ("Monovalent" means that peptide monomers are bound to the biopolymer scaffold (i.e. n=1) whereas "divalent" means that peptide dimers are bound to the biopolymer scaffold (i.e. n=2). In the present case, the divalent peptides were "homo-divalent", i.e. the peptide n-mer of the SADC is E006-S-E006.)

This demonstrates that SADCs with mono- or divalent peptides are very suitable to adsorb antibodies and thereby deplete them.

Example 4: Generation of Mimotope-Based SADCs

Linear and circular peptides derived from wild-type or modified peptide amino acid sequences can be used for the construction of specific SADCs for the selective removal of harmful, disease-causing or otherwise unwanted antibodies directed against a particular epitope. In case of a particular epitope, linear peptides or constrained peptides such as cyclopeptides containing portions of an epitope or variants thereof, where for example, one or several amino acids have been substituted or chemically modified in order to improve affinity to an antibody (mimotopes), can be used for constructing SADCs. A peptide screen can be performed with the aim of identifying peptides with optimized affinity to a disease-inducing autoantibody. The flexibility of structural or chemical peptide modification provided a solution to minimize the risk of immunogenicity, in particular of binding of the peptide to HLA and thus the risk of unwanted immune stimulation.

Therefore, wild-type as well as modified linear and circular peptide sequences were derived from a known epitope associated with an autoimmune disease. Peptides of various length and positions were systematically permutated by amino acid substitutions and synthesized on the PEPperCHIP® peptide array Platform (PEPperPRINT GmbH, Germany). This allowed screening of 60000 circular and linear wild-type and mimotope peptides derived from these sequences. The peptide arrays were incubated with an autoantibody known to be involved in the autoimmune disease. This autoantibody was therefore used to screen the 60000 peptides and 100 circular and 100 linear peptide hits were selected based on their relative binding strength to the autoantibody. Of these 200 peptides, 51 sequences were identical between the circular and the linear peptide group. All of the best peptides identified had at least one amino acid substitution when aligned to the original sequences, respectively and are therefore regarded as mimotopes. It also turned out that higher binding strengths can be achieved with circularized peptides.

These newly identified peptides, preferentially those with high relative binding values, are used to generate SADCs that are able to remove autoantibodies directed against this particular epitope or to develop further mimotopes and derivatives based on their sequences.

Example 5: Rapid, Selective Antibody Depletion in Mice Using Various SADC Biopolymer Scaffolds 10 µg of model undesired antibody mAB anti V5 (Thermo Scientific) was injected i.p. into female Balb/c mice (5 animals per treatment group; aged 9-11 weeks) followed by intravenous injection of 50 µg SADC (different biopolymer scaffolds with tagged V5 peptides bound, see below) 48 hrs after the initial antibody administration. Blood was collected at 24 hrs intervals from the submandibular vein. Blood samples for time point 0 hrs were taken just before SADC administration.

Figure 4:
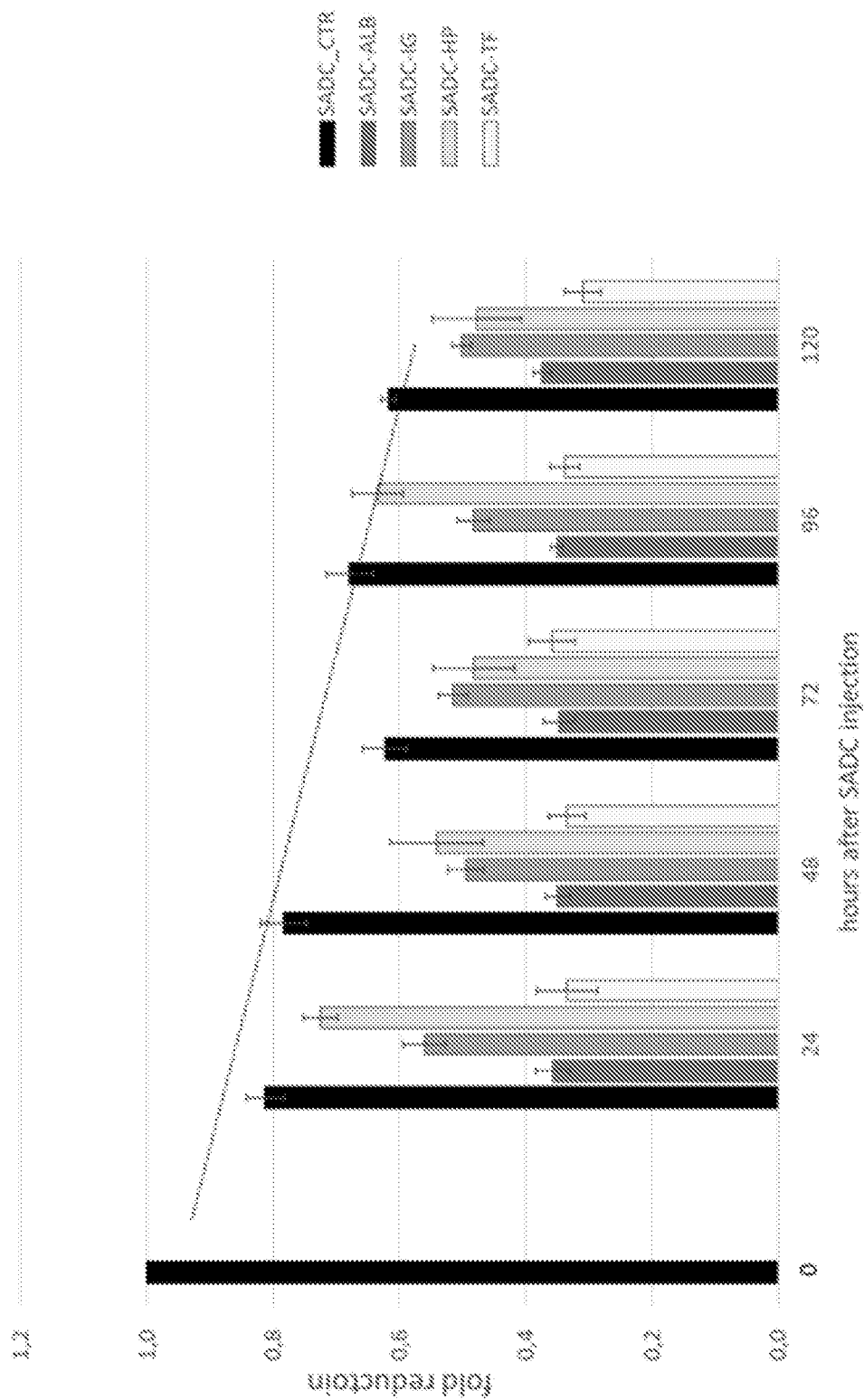
Figure 5:
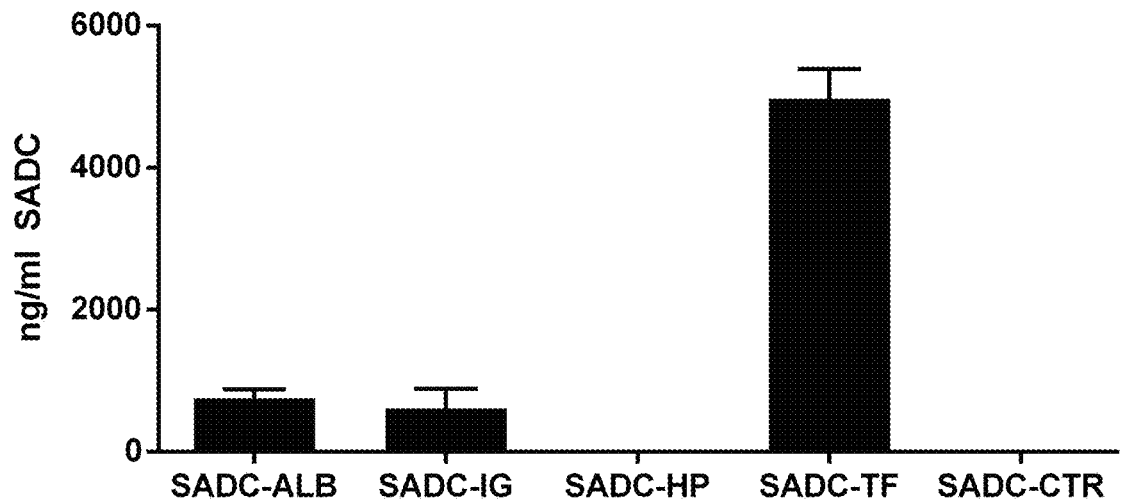

Blood was collected every 24 hrs until time point 120 hrs after the SADC administration (x-axis). The decay and reduction of plasma anti-V5 IgG levels after SADC administration was determined by anti V5 titer readout using standard ELISA procedures in combination with coated V5-peptide-BSA (peptide sequence IPNPLLGLDC-SEQ ID NO: 21) and detection by goat anti mouse IgG bio (Southern Biotech, diluted 1:2000) as shown in FIG. 4. In addition, SADC levels (see Example 6) and immunocomplex formation (see Example 7) were analyzed.

EC50[OD450] values were determined using 4 parameter logistic curve fitting and relative signal decay between the initial level (set to 1 at time point 0) and the following time points (x-axis) was calculated as ratio of the EC50 values (y-axis, fold signal reduction EC50). All SADC peptides contained tags for direct detection of SADC and immunocomplexes from plasma samples; peptide sequences used for SADCs were: IPNPLLGLDGGSGDYKDDDDKGK(SEQ ID NO: 22)-(BiotinAca)GC (SADC with albumin scaffold—SADC-ALB, SADC with immunoglobulin scaffold—SADC-IG, SADC with haptoglobin scaffold—SADC-HP, and SADC with transferrin scaffold—SADC-TF) and unrelated peptide VKKIHIPSEKGGSGDYKDDDDKGK(SEQ ID NO: 23)-(BiotinAca)GC as negative control SADC (SADC-CTR).

The SADC scaffolds for the different treatment groups of 5 animals are displayed in black/grey shades (see inset of FIG. 4).

Treated groups exhibited rapid and pronounced antibody reduction already at 24 hrs (in particular SADC-TF) when compared to the mock treated control group SADC-CTL. SADC-CTR was used as reference for a normal antibody decay since it has no antibody lowering activity because its peptide sequence is not recognized by the administered anti V5 antibody. The decay of SADC-CTR is thus marked with a trend line, emphasizing the antibody level differences between treated and mock treated animals.

In order to determine the effectivity of selective antibody lowering under these experimental conditions, a two-way ANOVA test was performed using a Dunnett's multiple comparison test. 48 hrs after SADC administration, the antibody EC50 was highly significantly reduced in all SADC groups ($p<0.0001$) compared to the SADC-CTR reference group (trend line). At 120 hrs after SADC administration, antibody decrease was highly significant in the SADC-ALB and SADC-TF groups (both $p<0.0001$) and significant in the SADC-HP group ($p=0.0292$), whereas the SADC-IG group showed a trend towards an EC50 reduction ($p=0.0722$) 120 hrs after SADC administration. Of note, selective antibody reduction was highly significant ($p<0.0001$) in the SADC-ALB and SADC-TF groups at all tested time-points after SADC administration.

It is concluded that all SADC biopolymer scaffolds were able to selectively reduce antibody levels. Titer reduction was most pronounced with SADC-ALB and SADC-TF and no rebound or recycling of antibody levels was detected towards the last time points suggesting that undesired antibodies are degraded as intended.

Example 6: Detection of SADCs in Plasma 24 Hrs after SADC Injection

Plasma levels of different SADC variants at 24 hrs after i.v. injection into Balb/c mice. Determination of Plasma levels (y-axis) of SADC-ALB, -IG, -HP, -TF and the negative control SADC-CTR (x-axis), were detected in the plasmas from the animals already described in example 5. Injected plasma SADC levels were detected by standard ELISA whereby SADCs were captured via their biotin moieties of their peptides in combination with streptavidin coated plates (Thermo Scientific). Captured SADCs were detected by mouse anti Flag-HRP antibody (Thermo Scientific, 1:2,000 diluted) detecting the Flag-tagged peptides (see also example 7):

Assuming a theoretical amount in the order of 25 μg/ml in blood after injecting 50 μg SADC i.v., the detectable amount of SADC ranged between 799 and 623 ng/ml for SADC-ALB or SADC-IG and up to approximately 5000 ng/ml for SADC-TF, 24 hrs after SADC injection. However surprisingly and in contrast, SADC-HP and control SADC-CTR (which is also a SADC-HP variant, however carrying the in this case unrelated negative control peptide E006, see previous examples), had completely disappeared from circulation 24 hrs after injection, and were not detectable anymore. See FIG. 5.

This demonstrates that both Haptoglobin scaffold-based SADCs tested in the present example ((namely SADC-HP and SADC-CTR) exhibit a relatively shorter plasma half-life which represents an advantage over SADCs such as SADC-ALB, SADC-IG oder SADC-TF in regard of their potential role in complement-dependent vascular and renal damage due to the in vivo risk of immunocomplex formation. Another advantage of SADC-HP is the accelerated clearance rate of their unwanted target antibody from blood in cases where a rapid therapeutic effect is needed. The present results demonstrate that Haptoglobin-based SADC scaffolds (as represented by SADC-HP and SADC-CTR) are subject to rapid clearance from the blood, regardless of whether SADC-binding antibodies are present in the blood, thereby minimizing undesirable immunocomplex formation and showing rapid and efficient clearance. Haptoglobin-based SADCs such as SADC-HP in the present example thus provide a therapeutically relevant advantage over other SADC biopolymer scaffolds, such as demonstrated by SADC-TF or SADC-ALB, both of which are still detectable 24 hrs after injection under the described conditions, in contrast to SADC-HP or SADC-CTR which both are completely cleared 24 hrs after injection.

Example 7: Detection of SADC-IgG Complexes in Plasma 24 Hrs after SADC Injection In order to determine the amount IgG bound to SADCs in vivo, after i.v. injection of 10 μg anti V5 IgG (Thermo Scientific) followed by injection of SADC-ALB, -HP, -TF and -CTR (50 µg) administered i.v. 48 h after antibody injection, plasma was collected from the submandibular vein, 24 hrs after SADC injection, and incubated on streptavidin plates for capturing SADCs from plasma via their biotinylated SADC-V5-peptide [IPN-PLLGLDGGSGDYKDDDDKGK(SEQ ID NO: 22) (BiotinAca)GC or in case of SADC-CTR the negative control peptide VKKIHIPSEKGGSGDYKDDDDKGK(SEQ ID NO: 23) (BiotinAca)GC]. IgG bound to the streptavidin-captured SADCs was detected by ELISA using a goat anti mouse IgG HRP antibody (Jackson Immuno Research, diluted 1:2,000) for detection of the SADC-antibody complexes present in plasma 24 hrs after SADC injection. OD450 nm values (y-axis) obtained for a negative control serum from untreated animals were subtracted from the OD450 nm values of the test groups (x-axis) for background correction.

Figure 6:
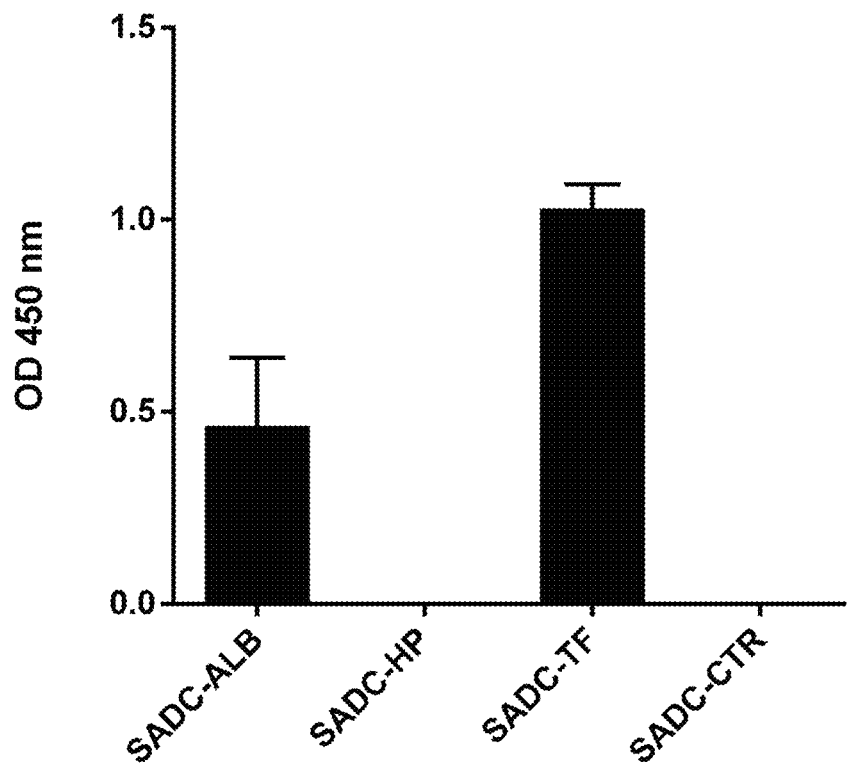

As shown in FIG. 6, pronounced anti-V5 antibody signals were seen in case of SADC-ALB and SADC-TF injected mice (black bars represent background corrected OD values at a dilution of 1:25, mean value of 5 mice; standard deviation error bars), whereas no antibody signal could be detected in plasmas from SADC-HP or control SADC-CTR injected animals (SADC-CTR is a negative control carrying the irrelevant peptide bio-FLG-E006 [VKKI-HIPSEKGGSGDYKDDDDKGK(SEQ ID NO: 23) (BiotinAca)GC] that is not recognized by any anti V5 antibody). This demonstrates the absence of detectable amounts of SADC-HP/IgG complexes in the plasma 24 hrs after i.v. SADC application.

SADC-HP is therefore subject to accelerated clearance in anti V5 pre-injected mice when compared to SADC-ALB or SADC-TF.

Example 8: In Vitro Analysis of SADC-Immunoglobulin Complex Formation

SADC-antibody complex formation was analyzed by pre-incubating 1 µg/ml of human anti V5 antibody (anti V5 epitope tag [SVS—P-K], human IgG3, Absolute Antibody) with increasing concentrations of SADC-ALB, -IG, -HP, -TF and -CTR (displayed on the x-axis) in PBS+0.1% w/v BSA+0.1% v/v Tween20 for 2 hours at room temperature in order to allow for immunocomplex formation in vitro. After complex formation, samples were incubated on ELISA plates that had previously been coated with 10 µg/ml of human C1q (CompTech) for 1 h at room temperature, in order to allow capturing of in vitro formed immunocomplexes. Complexes were subsequently detected by ELISA using anti human IgG (Fab specific)-Peroxidase (Sigma, diluted 1:1,000). Measured signals at OD450 nm (y-axis) reflect Antibody-SADC complex formation in vitro.

Figure 7:
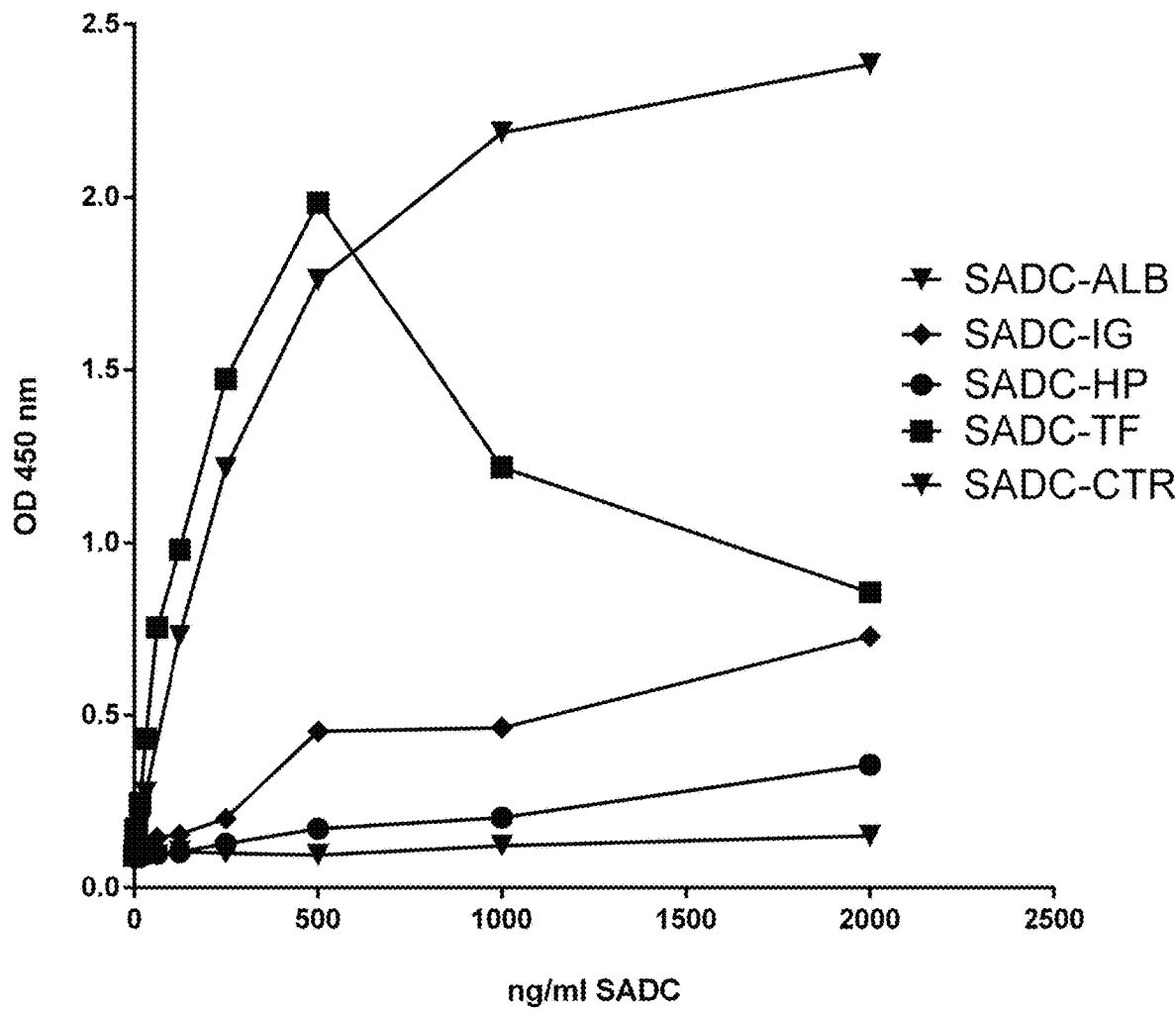

As shown in FIG. 7, SADC-TF and -ALB showed pronounced immunocomplex formation and binding to C1q as reflected by the strong signals and by sharp signal lowering in case 1000 ng/ml SADC-TF due to the transition from antigen-antibody equilibrium to antigen excess. In contrast, in vitro immunocomplex formation with SADC-HP or SADC-IG were much less efficient when measured in the present assay.

Together with the in vivo data (previous examples), these findings corroborate the finding that haptoglobin scaffolds are advantageous over other SADC biopolymer scaffolds because of the reduced propensity to activate the complement system. In contrast, SADC-TF or SADC-ALB show higher complexation, and thereby carry a certain risk of activating the C1 complex with initiation of the classical complement pathway (a risk which may be tolerable in some settings, however).

Example 9: Determination of IgG Capturing by SADCs In Vitro

Immunocomplexes were allowed to form in vitro, similar to the previous example, using 1 µg/ml mouse anti V5 antibody (Thermo Scientific) in combination with increasing amounts of SADCs (displayed on the x-axis). SADC-antibody complexes were captured on a streptavidin coated ELISA plate via the biotinylated SADC-peptides (see previous examples), followed by detection of bound anti-V5 using anti mouse IgG-HRP (Jackson Immuno Research, diluted 1:2,000).

Figure 8:
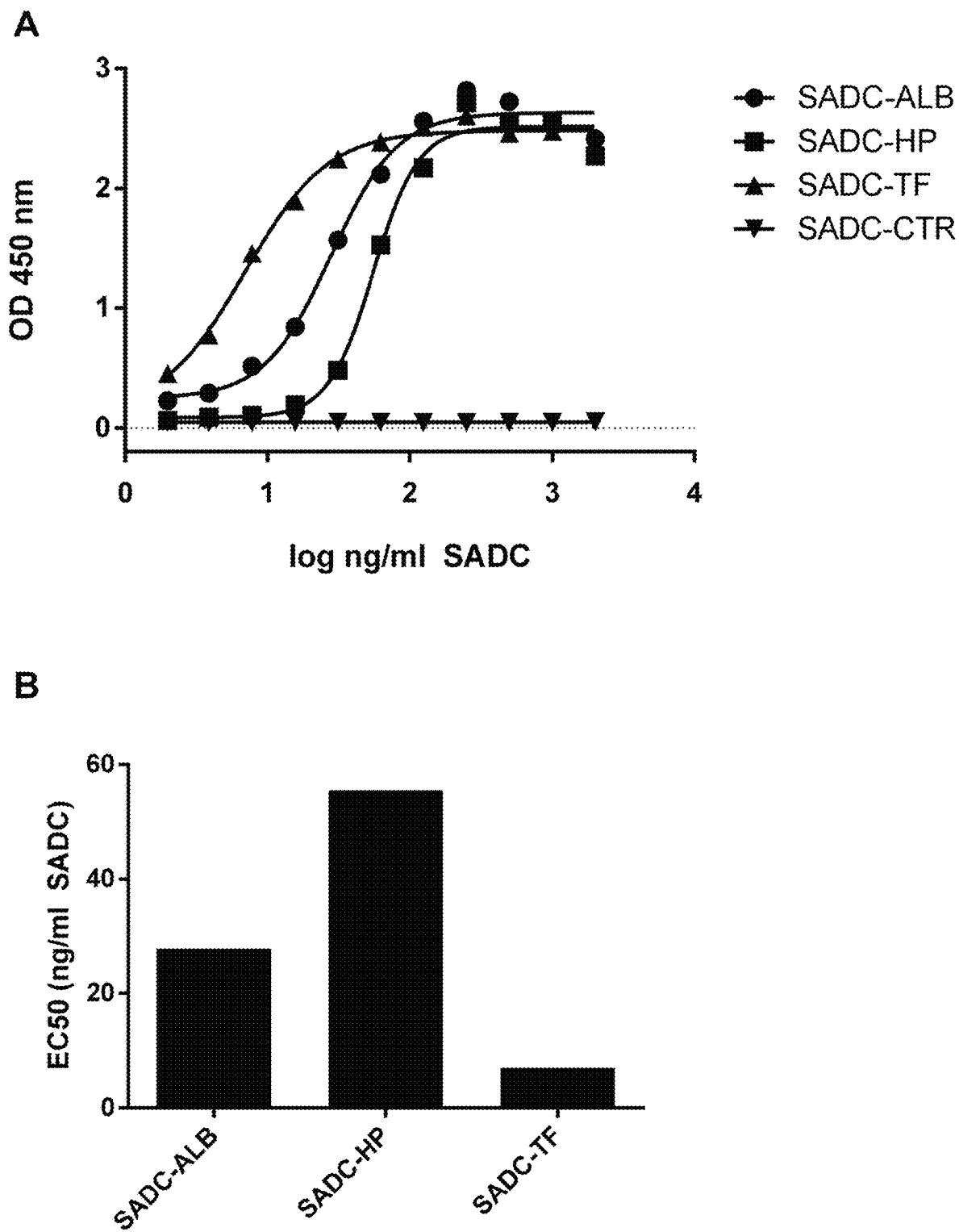

Under these assay conditions, SADC-HP showed markedly less antibody binding capacity in vitro when compared to SADC-TF or SADC-ALB (see FIG. 8, A). The calculated EC50 values for IgG detection on SADCs were 7.0 ng/ml, 27.9 ng/ml and 55.5 ng/ml for SADC-TF, -ALB and -HP, respectively (see FIG. 8, B).

This in vitro finding is consistent with the observation (see previous examples) that SADC-HP has a lower immunocomplex formation capacity when compared to SADC-TF or SADC-ALB which is regarded as a safety advantage with respect to its therapeutic use for the depletion of unwanted antibodies.

Example 10: SADCs to Reduce Undesired Antibodies Against AAV-8

Three SADCs are provided to reduce AAV-8-neutralizing antibodies which hamper gene therapy (see Gurda et al. for the epitopes used; see also AAV-8 capsid protein sequence UniProt Q8JQF8, sequence version 1):
(a) SADC-a with haptoglobin as biopolymer scaffold and at least two peptides with the sequence LQQQNT (SEQ ID NO: 18) covalently bound to the scaffold,
(b) SADC-b with transferrin as biopolymer scaffold and at least two peptides with the sequence TTTGQNNNS (SEQ ID NO: 19) covalently bound to the scaffold, and
(c) SADC-c with albumin as biopolymer scaffold and at least two peptides with the sequence GTANTQ (SEQ ID NO: 20) covalently bound to the scaffold.
These SADCs are administered to an individual who will undergo gene therapy with AAV-8 as vector in order to increase efficiency of the gene therapy.

NON-PATENT REFERENCES

Carter, John Mark, and Larry Loomis-Price. "B cell epitope mapping using synthetic peptides." Current protocols in immunology 60.1 (2004): 9-4.
Elliott, Serra E., et al. "A pre-eclampsia-associated Epstein-Barr virus antibody cross-reacts with placental GPR50." Clinical Immunology 168 (2016): 64-71.
Erlandsson, Ann, et al. "In vivo clearing of idiotypic antibodies with antiidiotypic antibodies and their derivatives." Molecular immunology 43.6 (2006): 599-606.
Garces, Jorge Carlos, et al. "Antibody-mediated rejection: a review." The Ochsner Journal 17.1 (2017): 46.
Gazarian, Karlen, et al. "Mimotope peptides selected from phage display combinatorial library by serum antibodies of pigs experimentally infected with *Taenia solium* as leads to developing diagnostic antigens for human neurocysticercosis." Peptides 38.2 (2012): 381-388.

Gfeller, David, et al. "Current tools for predicting cancer-specific T cell immunity." Oncoimmunology 5.7 (2016): e1177691.

Gurda, Brittney L., et al. "Mapping a neutralizing epitope onto the capsid of adeno-associated virus serotype 8." Journal of virology 86.15 (2012): 7739-7751.

Jansson, Liselotte, et al. "Immunotherapy With Apitopes Blocks the Immune Response to TSH Receptor in HLA-DR Transgenic Mice." Endocrinology 159.9 (2018): 3446-3457.

Jensen, Kamilla Kjaergaard, et al. "Improved methods for predicting peptide binding affinity to MHC class II molecules." Immunology 154.3 (2018): 394-406.

Jurtz, Vanessa, et al. "NetMHCpan-4.0: improved peptide-MHC class I interaction predictions integrating eluted ligand and peptide binding affinity data." The Journal of Immunology 199.9 (2017): 3360-3368.

Koşaloğlu-Yalçin, et al. "Predicting T cell recognition of MHC class I restricted neoepitopes." Oncoimmunology 7.11 (2018): e1492508.

Hansen, Lajla Bruntse, Soren Buus, and Claus Schafer-Nielsen. "Identification and mapping of linear antibody epitopes in human serum albumin using high-density peptide arrays." PLoS One 8.7 (2013): e68902.

Homma, Masayuki, et al. "A Novel Fusion Protein, AChR-Fc, Ameliorates Myasthenia Gravis by Neutralizing Anti-acetylcholine Receptor Antibodies and Suppressing Acetylcholine Receptor-Reactive B Cells." Neurotherapeutics 14.1 (2017): 191-198.

Howard Jr, James F. "Myasthenia gravis: the role of complement at the neuromuscular junction." Annals of the New York Academy of Sciences 1412.1 (2018): 113-128.

Howarth, M., & Brune, K. D. (2018). New routes and opportunities for modular construction of particulate vaccines: stick, click and glue. Frontiers in immunology, 9, 1432.

Lazaridis, Konstantinos, et al. "Specific removal of autoantibodies by extracorporeal immunoadsorption ameliorates experimental autoimmune myasthenia gravis." Journal of neuroimmunology 312 (2017): 24-30.

Leung, Nicki Y H, et al. "Screening and identification of mimotopes of the major shrimp allergen tropomyosin using one-bead-one-compound peptide libraries." Cellular & molecular immunology 14.3 (2017): 308-318.

Lim, Sung In, and Inchan Kwon. "Bioconjugation of therapeutic proteins and enzymes using the expanded set of genetically encoded amino acids." Critical reviews in biotechnology 36.5 (2016): 803-815.

Lin, Chia-Hao, et al. "Identification of a major epitope by anti-interferon-γ autoantibodies in patients with mycobacterial disease." Nature medicine 22.9 (2016): 994.

Lorentz, Kristen M., et al. "Engineered binding to erythrocytes induces immunological tolerance to E. coli asparaginase." Science advances 1.6 (2015): e1500112.

Luo, Jie, et al. "Main immunogenic region structure promotes binding of conformation-dependent myasthenia gravis autoantibodies, nicotinic acetylcholine receptor conformation maturation, and agonist sensitivity." Journal of Neuroscience 29.44 (2009): 13898-13908.

Luo, Jie, and Jon Lindstrom. "AChR-specific immunosuppressive therapy of myasthenia gravis." Biochemical pharmacology 97.4 (2015): 609-619.

Majowicz, Anna, et al. "Seroprevalence of pre-existing NABs against AAV1, 2, 5, 6 and 8 in the South African Hemophilia B patient population." (2019): 3353-3353.

Mazor, Ronit, et al. "Tolerogenic nanoparticles restore the antitumor activity of recombinant immunotoxins by mitigating immunogenicity." Proceedings of the National Academy of Sciences 115.4 (2018): E733-E742.

Meister, Daniel, S. Maryamdokht Taimoory, and John F. Trant. "Unnatural amino acids improve affinity and modulate immunogenicity: Developing peptides to treat MHC type II autoimmune disorders." Peptide Science 111.1 (2019): e24058.

Mingozzi, Federico, et al. "Overcoming preexisting humoral immunity to AAV using capsid decoys." Science translational medicine 5.194 (2013): 194ra92-194ra92.

Mingozzi, Federico, and Katherine A. High. "Overcoming the host immune response to adeno-associated virus gene delivery vectors: the race between clearance, tolerance, neutralization, and escape." Annual review of virology 4 (2017): 511-534.

Morimoto et. al., Bioconjugate Chemistry 25 (8) (2014): 1479-1491

Moussa, Ehab M., et al. "Immunogenicity of therapeutic protein aggregates." Journal of pharmaceutical sciences 105.2 (2016): 417-430.

Müller, Manuel M. "Post-translational modifications of protein backbones: unique functions, mechanisms, and challenges." Biochemistry 57.2 (2017): 177-185.

Siang Ong, Yong, et al. "Recent advances in synthesis and identification of cyclic peptides for bioapplications." Current topics in medicinal chemistry 17.20 (2017): 2302-2318.

Peters, Bjoern, et al. "A community resource benchmarking predictions of peptide binding to MHC-I molecules." PLoS computational biology 2.6 (2006): e65.

Pishesha, Novalia, et al. "Engineered erythrocytes covalently linked to antigenic peptides can protect against autoimmune disease." Proceedings of the National Academy of Sciences (2017): 201701746.

Rey et al., Clinical Immunology 96 (3) (2000): 269-279

Ruff, Robert L., and Robert P. Lisak. "Nature and action of antibodies in myasthenia gravis." Neurologic clinics 36.2 (2018): 275-291.

Rummler, Silke, et al. "Current techniques for ABO-incompatible living donor liver transplantation." World journal of transplantation 6.3 (2016): 548.

Runcie, Karie, et al. "Bi-specific and tri-specific antibodies—the next big thing in solid tumor therapeutics." Molecular Medicine 24.1 (2018): 50.

Ryan, Brent J., Ahuva Nissim, and Paul G. Winyard. "Oxidative post-translational modifications and their involvement in the pathogenesis of autoimmune diseases." Redox biology 2 (2014): 715-724.

Shanmugam, Arulkumaran, et al. "Identification of PSA peptide mimotopes using phage display peptide library." Peptides 32.6 (2011): 1097-1102.

Sorensen, Karen Kristine, et al. "Liver sinusoidal endothelial cells." Comprehensive Physiology 5.4 (2011): 1751-1774.

Spiess, Christoph, Qianting Zhai, and Paul J. Carter. "Alternative molecular formats and therapeutic applications for bispecific antibodies." Molecular immunology 67.2 (2015): 95-106.

Taddeo, Adriano, et al. "Selection and depletion of plasma cells based on the specificity of the secreted antibody." European journal of immunology 45.1 (2015): 317-319.

Teschner, Sven, et al. "AB0-incompatible kidney transplantation using regenerative selective immunoglobulin adsorption." Journal of clinical apheresis 27.2 (2012): 51-60.

Tetala, Kishore K R, et al. "Selective depletion of neuropathy-related antibodies from human serum by monolithic affinity columns containing ganglioside mimics." Journal of medicinal chemistry 54.10 (2011): 3500-3505.

Vincent, Angela, et al. "Serological and experimental studies in different forms of myasthenia gravis." Annals of the New York Academy of Sciences 1413.1 (2018): 143-153.

Wallukat, Gerd, et al. "Patients with preeclampsia develop agonistic autoantibodies against the angiotensin AT 1 receptor." The Journal of clinical investigation 103.7 (1999): 945-952.

Zhou, Cissy C., et al. "Angiotensin receptor agonistic autoantibodies induce pre-eclampsia in pregnant mice." Nature medicine 14.8 (2008): 855.

What is claimed is:

1. A method of rapid, selective depletion of an antibody when the antibody has become undesirable in an individual, the method comprising the following steps:
(i) identifying at least one mimotope for which the antibody is specific;
(ii) administering a first pharmaceutical composition comprising the antibody to a human individual in need thereof; and
(iii) administering a second pharmaceutical composition to said individual, wherein the second pharmaceutical composition comprises at least one pharmaceutically acceptable excipient and a compound comprising
a biopolymer scaffold selected from the group consisting of a human albumin, a human transferrin, a human alpha1-globulin, a human alpha2-globulin, a human beta globulin, and a human haptoglobin, and at least
a first mimotope of said antibody, wherein the first mimotope has a sequence length of 6-13 amino acids and does not bind to any human leukocyte antigen (HLA) class I molecule, and
a second mimotope of said antibody, wherein the second mimotope has a sequence length of 6-13 amino acids and does not bind to any HLA class I molecule;
wherein each of the first and second mimotopes is covalently bound to the biopolymer scaffold; and
wherein the second pharmaceutical composition of step (iii) is non-immunogenic in the individual; and
wherein step (iii) is performed after step (ii), wherein step (iii) is performed when the antibody has become undesirable in the individual.

2. The method of claim 1, wherein the biopolymer scaffold is selected from the group consisting of human albumin, human alpha1-globulin, human alpha2-globulin and human beta-globulin.

3. The method of claim 2, wherein the biopolymer scaffold is a human transferrin.

4. The method of claim 2, wherein the biopolymer scaffold is a human albumin.

5. The method of claim 1, wherein the antibody is a monoclonal antibody.

6. The method of claim 1, wherein the individual has been administered an antibody-drug conjugate or a nanobody.

7. The method of claim 1, wherein the individual has been administered a diagnostic antibody.

8. The method of claim 1, wherein the individual has been administered a therapeutic antibody.

9. The method of claim 1, wherein the individual has a malignancy or a cancer.

10. The method of claim 8, wherein step (iii) is performed in case of an adverse event induced by the antibody.

11. The method of claim 8, wherein step (iii) is performed as an emergency intervention.

12. The method of claim 1, wherein the molar ratio of the first and second mimotopes together to biopolymer scaffold in the composition is from 7:1 to 50:1.

13. The method of claim 1,
wherein the first mimotope and the second mimotope are different.

14. A method of rapid, selective depletion of an antibody when the antibody has become undesirable in an individual, the method comprising the following steps:
(i) identifying at least one mimotope for which the antibody is specific;
(ii) administering a first pharmaceutical composition comprising the antibody to a human individual in need thereof, wherein the individual has a malignancy or a cancer; and
(iii) administering a second pharmaceutical composition to said individual, wherein the pharmaceutical composition comprises at least one pharmaceutically acceptable excipient and a compound comprising
a biopolymer scaffold selected from the group consisting of a human transferrin, a human alpha1-globulin, a human alpha2-globulin, a human beta globulin, and a human haptoglobin, and at least
a first mimotope P of said antibody and
a second mimotope P of said antibody;
wherein, independently for each occurrence, P is a peptide with a sequence length of 7-13 amino acids and does not bind to any HLA class I molecule, and
wherein each of the first and second mimotopes is covalently bound to the biopolymer scaffold;
wherein the molar ratio of the first and second mimotopes P together to biopolymer scaffold in the composition is from 7:1 to 50:1; and
wherein the second pharmaceutical composition is non-immunogenic in the individual; and
wherein step (iii) is performed after step (ii), wherein step (iii) is performed when the antibody has become undesirable in the individual.

15. A method of rapid, selective depletion of an antibody when the antibody has become undesirable in an individual, the method comprising the following steps:
(i) identifying at least one mimotope for which the antibody is specific;

(ii) administering a first pharmaceutic composition comprising the antibody to a human individual in need thereof wherein the individual has a malignancy or a cancer; and
(iii) administering a second pharmaceutical composition to said individual, wherein the pharmaceutical composition comprises at least one pharmaceutically acceptable excipient and a compound comprising
 a biopolymer scaffold, wherein the biopolymer scaffold is human transferrin, and at least
 a first mimotope P of said antibody and
 a second mimotope P of said antibody;
wherein, independently for each occurrence, P is a peptide with a sequence length of 7-13 amino acids and does not bind to any HLA class I molecule,
wherein each of the first mimotope and the second mimotope is covalently bound to the biopolymer scaffold;
wherein the molar ratio of the first and second mimotopes P together to biopolymer scaffold in the composition is from 7:1 to 50:1; and
wherein the second pharmaceutical composition is non-immunogenic in the individual; and
wherein step (iii) is performed after step (ii), wherein step (iii) is performed when the antibody has become undesirable in the individual.

* * * * *

SEQUENCE LISTING

```
<160> NUMBER OF SEQ ID NOS: 23

<210> SEQ ID NO 1
<211> LENGTH: 20
<212> TYPE: PRT
<213> ORGANISM: Artificial Sequence
<220> FEATURE:
<223> OTHER INFORMATION: Synthesized in the laboratory

<400> SEQUENCE: 1

Leu Lys Trp Asn Pro Asp Asp Tyr Gly Gly Val Lys Lys Ile His Ile
1               5                   10                  15

Pro Ser Glu Lys
            20

<210> SEQ ID NO 2
<211> LENGTH: 10
<212> TYPE: PRT
<213> ORGANISM: Artificial Sequence
<220> FEATURE:
<223> OTHER INFORMATION: Synthesized in the laboratory

<400> SEQUENCE: 2

Trp Asn Pro Asp Asp Tyr Gly Gly Val Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthesized in the laboratory

<400> SEQUENCE: 3

Val Lys Lys Ile His Ile Pro Ser Glu Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthesized in the laboratory

<400> SEQUENCE: 4

Val Lys Lys Ile His Ile Pro Ser Glu Lys Gly
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthesized in the laboratory
```

```
<400> SEQUENCE: 5

Arg Pro Gln Lys Arg Pro Ser Cys Ile Gly Cys Lys Gly Thr His
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthesized in the laboratory

<400> SEQUENCE: 6

Arg Pro Gln Lys Arg Pro Ser Cys Ile Gly Cys Lys Gly Ala His
1               5                   10                  15

<210> SEQ ID NO 7
<211> LENGTH: 9
<212> TYPE: PRT
<213> ORGANISM: Artificial Sequence
<220> FEATURE:
<223> OTHER INFORMATION: Synthesized in the laboratory

<400> SEQUENCE: 7

Lys Arg Pro Ser Cys Ile Gly Cys Lys
1               5

<210> SEQ ID NO 8
<211> LENGTH: 27
<212> TYPE: PRT
<213> ORGANISM: Artificial Sequence
<220> FEATURE:
<223> OTHER INFORMATION: Synthesized in the laboratory

<400> SEQUENCE: 8

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile
            20                  25

<210> SEQ ID NO 9
<211> LENGTH: 15
<212> TYPE: PRT
<213> ORGANISM: Artificial Sequence
<220> FEATURE:
<223> OTHER INFORMATION: Synthesized in the laboratory

<400> SEQUENCE: 9

Thr Ala Met Glu Tyr Arg Trp Pro Phe Gly Asn Tyr Leu Cys Lys
1               5                   10                  15

<210> SEQ ID NO 10
<211> LENGTH: 30
<212> TYPE: PRT
<213> ORGANISM: Artificial Sequence
<220> FEATURE:
<223> OTHER INFORMATION: Synthesized in the laboratory

<400> SEQUENCE: 10

Ala Ile Ile His Arg Asn Val Phe Phe Ile Glu Asn Thr Asn Ile Thr
1               5                   10                  15

Val Cys Ala Phe His Tyr Glu Ser Gln Asn Ser Thr Leu Pro
            20                  25                  30

<210> SEQ ID NO 11
<211> LENGTH: 13
```

```
<212> TYPE: PRT
<213> ORGANISM: Artificial Sequence
<220> FEATURE:
<223> OTHER INFORMATION: Synthesized in the laboratory

<400> SEQUENCE: 11

Asp Val Leu Ile Gln Leu Gly Ile Ile Arg Asp Cys Arg
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthesized in the laboratory

<400> SEQUENCE: 12

Ala Phe His Tyr Glu Ser Gln
1               5

<210> SEQ ID NO 13
<211> LENGTH: 11
<212> TYPE: PRT
<213> ORGANISM: Artificial Sequence
<220> FEATURE:
<223> OTHER INFORMATION: Synthesized in the laboratory

<400> SEQUENCE: 13

Gly Arg Pro Gln Lys Arg Pro Ser Cys Ile Gly
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Synthesized in the laboratory

<400> SEQUENCE: 14

Cys Gly Arg Pro Gln Lys Arg Pro Ser Cys Ile Gly Cys Lys Gly
1               5                   10                  15

<210> SEQ ID NO 15
<211> LENGTH: 22
<212> TYPE: PRT
<213> ORGANISM: Artificial Sequence
<220> FEATURE:
<223> OTHER INFORMATION: Synthesized in the laboratory

<400> SEQUENCE: 15

Leu Lys Trp Asn Pro Asp Asp Tyr Gly Gly Val Lys Lys Ile His Ile
1               5                   10                  15

Pro Ser Glu Lys Gly Cys
            20

<210> SEQ ID NO 16
<211> LENGTH: 13
<212> TYPE: PRT
<213> ORGANISM: Artificial Sequence
<220> FEATURE:
<223> OTHER INFORMATION: Synthesized in the laboratory

<400> SEQUENCE: 16

Asp His Thr Leu Tyr Thr Pro Tyr His Thr His Pro Gly
1               5                   10
```

```
<210> SEQ ID NO 17
<211> LENGTH: 12
<212> TYPE: PRT
<213> ORGANISM: Artificial Sequence
<220> FEATURE:
<223> OTHER INFORMATION: Synthesized in the laboratory

<400> SEQUENCE: 17

Gly Gly Val Lys Lys Ile His Ile Pro Ser Glu Lys
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Synthesized in the laboratory

<400> SEQUENCE: 18

Leu Gln Gln Gln Asn Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Synthesized in the laboratory

<400> SEQUENCE: 19

Thr Thr Thr Gly Gln Asn Asn Asn Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Synthesized in the laboratory

<400> SEQUENCE: 20

Gly Thr Ala Asn Thr Gln
1               5

<210> SEQ ID NO 21
<211> LENGTH: 10
<212> TYPE: PRT
<213> ORGANISM: Artificial Sequence
<220> FEATURE:
<223> OTHER INFORMATION: Synthesized in the laboratory

<400> SEQUENCE: 21

Ile Pro Asn Pro Leu Leu Gly Leu Asp Cys
1               5                   10

<210> SEQ ID NO 22
<211> LENGTH: 23
<212> TYPE: PRT
<213> ORGANISM: Artificial Sequence
<220> FEATURE:
<223> OTHER INFORMATION: Synthesized in the laboratory

<400> SEQUENCE: 22

Ile Pro Asn Pro Leu Leu Gly Leu Asp Gly Gly Ser Gly Asp Tyr Lys
1               5                   10                  15

Asp Asp Asp Asp Lys Gly Lys
            20
```

```
<210> SEQ ID NO 23
<211> LENGTH: 24
<212> TYPE: PRT
<213> ORGANISM: Artificial Sequence
<220> FEATURE:
<223> OTHER INFORMATION: Synthesized in the laboratory

<400> SEQUENCE: 23

Val Lys Lys Ile His Ile Pro Ser Glu Lys Gly Gly Ser Gly Asp Tyr
1               5                   10                  15

Lys Asp Asp Asp Lys Gly Lys
            20
```